(12) United States Patent
Stamford et al.

(10) Patent No.: US 8,722,708 B2
(45) Date of Patent: May 13, 2014

(54) SUBSTITUTED ISOINDOLINES AS ASPARTYL PROTEASE INHIBITORS

(75) Inventors: Andrew Stamford, Chatham Township, NJ (US); Guoqing Li, Belle Mead, NJ (US); William Greenlee, Teaneck, NJ (US); Zhaoning Zhu, Plainsboro, NJ (US); Brian McKittrick, New Vernon, NJ (US); Robert Mazzola, Stewartsville, NJ (US); Ying Huang, East Brunswick, NJ (US); Tao Guo, Dayton, NJ (US); Thuy X. H. Le, Monmouth Junction, NJ (US); Gang Qian, Kendall Park, NJ (US); Yuefei Shao, Princeton, NJ (US)

(73) Assignees: Merck Sharp & Dohme Inc., Rahway, NJ (US); Pharmacopeia Drug Discovery, Inc., Princeton, NJ (US)

( * ) Notice: Subject to any disclaimer, the term of this patent is extended or adjusted under 35 U.S.C. 154(b) by 839 days.

(21) Appl. No.: 11/451,065

(22) Filed: Jun. 12, 2006

(65) Prior Publication Data

US 2008/0176868 A1  Jul. 24, 2008

Related U.S. Application Data

(60) Provisional application No. 60/690,541, filed on Jun. 14, 2005.

(51) Int. Cl.
| | |
|---|---|
| C07D 487/04 | (2006.01) |
| A61K 31/519 | (2006.01) |
| A61K 31/4035 | (2006.01) |
| A61K 31/4406 | (2006.01) |
| C07D 487/14 | (2006.01) |
| A61K 31/437 | (2006.01) |
| A61P 25/28 | (2006.01) |
| A61P 9/00 | (2006.01) |
| A61P 31/14 | (2006.01) |

(52) U.S. Cl.
USPC ........ 514/339; 514/416; 514/300; 514/265.1; 514/259.1; 514/267; 546/277.1; 546/112; 548/471; 544/280; 544/281; 544/279

(58) Field of Classification Search
USPC ............... 548/406, 414, 471; 514/63, 81, 469
See application file for complete search history.

(56) References Cited

U.S. PATENT DOCUMENTS

| | | | |
|---|---|---|---|
| 3,632,814 | A | 1/1972 | Richter et al. |
| 4,758,663 | A * | 7/1988 | Scherer et al. ............... 544/284 |
| 6,683,091 | B2 | 1/2004 | Asberom et al. |
| 7,855,213 | B2 | 12/2010 | Arnold et al. |
| 2005/0282825 | A1 | 12/2005 | Malamas et al. |
| 2005/0282826 | A1 | 12/2005 | Malamas et al. |
| 2007/0004730 | A1 | 1/2007 | Zhou et al. |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0099875 | A1 | 5/2007 | Zhu et al. |
| 2007/0203116 | A1 | 8/2007 | Quiaglato et al. |
| 2007/0232642 | A1 | 10/2007 | Baxter et al. |
| 2007/0259898 | A1 | 11/2007 | Baxter et al. |
| 2007/0287692 | A1 | 12/2007 | Wu et al. |
| 2007/0299087 | A1 | 12/2007 | Berg et al. |
| 2008/0051420 | A1 | 2/2008 | Berg et al. |
| 2008/0058349 | A1 | 3/2008 | Berg et al. |
| 2008/0161269 | A1 | 7/2008 | Berg et al. |
| 2008/0214577 | A1 | 9/2008 | Berg et al. |

(Continued)

FOREIGN PATENT DOCUMENTS

| | | | |
|---|---|---|---|
| DE | 2430354 | | 8/1972 |
| DE | 2430354 | * | 1/1976 |

(Continued)

OTHER PUBLICATIONS

Weib et. al. (Monatschefte fuer Chemie, 1924, 45, 105-114).*

(Continued)

*Primary Examiner* — Susanna Moore
(74) *Attorney, Agent, or Firm* — Keith D. MacMillan; John C. Todaro

(57) ABSTRACT

Disclosed are compounds of the formula I

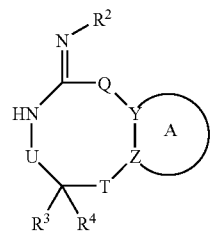

or a stereoisomer, tautomer, or pharmaceutically acceptable salt or solvate thereof, wherein Q is a bond or —N($R^5$)—;
T is a bond, —O—, —C(O)—; S, —N($R^5$)—, or —C($R^6R^7$);
U is a bond or —C($R^6$)($R^7$)—
Y is C or N;
Z is C or N;
ring A, including variables Y and Z, is a three to nine membered cycloalkyl, cycloalkenyl, heterocyclyl, heterocyclenyl, aryl, and heteroaryl ring having 0 to 4, preferably 0 to 2, heteroatoms independently selected from the group consisting of O, S, N and —N(R)—, wherein ring A is unsubstituted or substituted with 1 to 5 independently selected $R^1$ moieties and/or oxo when ring A is cycloalkyl, cycloalkenyl, heterocyclyl or heterocyclenyl;
and R, $R^1$, $R^2$, $R^3$, $R^4$, $R^5$, $R^6$, $R^6$, $R^7$ and $R^7$ are as defined in the specification; pharmaceutical compositions comprising the compounds of formula I and the method of inhibiting aspartyl protease, and in particular, the methods of treating cardiovascular diseases, cognitive and neurodegenerative diseases.

9 Claims, No Drawings

(56) References Cited

U.S. PATENT DOCUMENTS

| | | |
|---|---|---|
| 2008/0287460 A1 | 11/2008 | Burrows et al. |
| 2008/0287462 A1 | 11/2008 | Chessari et al. |
| 2009/0023762 A1 | 1/2009 | Berg et al. |
| 2009/0062282 A1 | 3/2009 | Albert et al. |
| 2009/0209529 A1 | 8/2009 | Andreini et al. |

FOREIGN PATENT DOCUMENTS

| | | | |
|---|---|---|---|
| EP | 742217 | * | 11/1996 |
| JP | 08225753 | * | 9/1996 |
| WO | WO 93/04047 | | 3/1993 |
| WO | WO 96/14844 | | 5/1996 |
| WO | WO 99/11622 | | 3/1999 |
| WO | WO 99/33795 A | | 7/1999 |
| WO | WO 0202512 | | 1/2002 |
| WO | WO 02/074719 A2 | | 9/2002 |
| WO | WO 2005/058311 A1 | | 6/2005 |
| WO | WO 2006/009655 A1 | | 1/2006 |
| WO | WO 2006/017836 A2 | | 2/2006 |
| WO | WO 2006/017844 A1 | | 2/2006 |
| WO | WO 2006/024932 A1 | | 3/2006 |
| WO | WO 2006/041404 A1 | | 4/2006 |
| WO | WO 2006/044497 A2 | | 4/2006 |
| WO | WO 2006/076284 A2 | | 7/2006 |
| WO | WO2006138264 | | 12/2006 |
| WO | WO2006138266 | | 12/2006 |
| WO | WO 2007/049532 A1 | | 5/2007 |
| WO | WO 2007/050612 A1 | | 5/2007 |
| WO | WO2007050721 | | 5/2007 |
| WO | WO2007058583 | | 5/2007 |
| WO | WO 2007/092839 A2 | | 8/2007 |
| WO | WO 2007/092846 A2 | | 8/2007 |
| WO | WO 2007/092854 A2 | | 8/2007 |
| WO | WO 2007/114771 A1 | | 10/2007 |
| WO | WO 2007/149033 A1 | | 12/2007 |
| WO | WO2007145568 | | 12/2007 |
| WO | WO2007145569 | | 12/2007 |
| WO | WO2007145570 | | 12/2007 |
| WO | WO2007145571 | | 12/2007 |
| WO | WO 2008/022024 A2 | | 2/2008 |
| WO | WO2008063114 | | 5/2008 |
| WO | WO2008073365 | | 6/2008 |
| WO | WO2008073370 | | 6/2008 |
| WO | WO 2008/103351 A2 | | 8/2008 |
| WO | WO 2008/133273 A1 | | 11/2008 |
| WO | WO 2008/133274 A1 | | 11/2008 |
| WO | WO 2009/005470 A1 | | 1/2009 |
| WO | WO 2009/005471 A1 | | 1/2009 |
| WO | WO 2009/022961 A1 | | 2/2009 |
| WO | WO 2009/007300 A2 | | 7/2009 |
| WO | WO 2009/091016 A1 | | 7/2009 |
| WO | WO 2009/092566 A1 | | 7/2009 |
| WO | WO 2009/097278 A1 | | 8/2009 |
| WO | WO 2009/097401 A1 | | 8/2009 |
| WO | WO 2009/108550 A1 | | 9/2009 |
| WO | WO 2009/131974 A1 | | 10/2009 |
| WO | WO 2009/131975 A1 | | 10/2009 |
| WO | WO2009131974 | | 10/2009 |
| WO | WO2009131975 | | 10/2009 |
| WO | WO 2009/134617 A1 | | 11/2009 |
| WO | WO 2009/151098 A1 | | 12/2009 |
| WO | WO 2010/013302 A1 | | 2/2010 |
| WO | WO 2010/013794 A1 | | 2/2010 |
| WO | WO 2010/038686 A1 | | 4/2010 |
| WO | WO 2010/047372 A1 | | 4/2010 |
| WO | WO 2010/056194 A1 | | 5/2010 |
| WO | WO 2010/059953 A1 | | 5/2010 |
| WO | WO2010056194 | | 5/2010 |
| WO | WO2010056195 | | 5/2010 |

OTHER PUBLICATIONS

Barrett et. al. (Journal of the Chemical Society, 1939, 1809-1820).*
STN printout, downloaded Jul. 5, 2008, pp. 1-10.*
Vippagunta et. al. (Advanced Drug Delivery Reviews, 2001, 48, 3-26.*
Bartlett et al. (Journal of the Chemical Society, Section C: Organic, 1969, 2, p. 129-133).*
Matsumoto et al. (JP 08225753), machine translation, 1996.*
International Search Report PCT/US2006/0022919, mailing date Dec. 18, 2006.
Baxter, Ellen, et. al.; Journal of Medicinal Chemistry; vol. 50, No. 18, Sep. 6, 2007; "2-Amino-3,4-dihydroquinazolines as Inhibitors of BACE-1 . . . "; Published on Web on Aug. 8, 2007.
Buteau, Kristen C.; "Deuterated Drugs: Unexpectedly Nonobvious?", 10 J. High Tech L. 22 (2009).
Zhu, Zhaoning, et. al.; Journal of Medicinal Chemistry, vol. 53, No. 3, "Discovery of Cyclic Acylguanidines as Highly Potent and Selective . . . "; Sep. 21, 2009, pp. 951-965.
Nowak, Paweit, et. al.; Biiorganic and Medicinal Chemistry Letters; 20 (2010); "Discovery and initial optimization of 5, 5'-disubstituted aminohydantoins as potent . . . "; pp. 632-635.
Zhou, Ping, et. al.; Biiorganic and Medicinal Chemistry Letters; 20 (2010);"Pyridinyl aminohydantoins as small molecule BACE1 inhibitors"; pp. 2326-2329.
Malamas, Michael S.; et. al.; Biiorganic and Medicinal Chemistry Letters; 18 (2010); "Di-substituted pyridinyl aminohydantoins as potent and highly selective human . . . "; pp. 630-639.
Zhou, Ping; et. al.; "Pyridinylaminohydantoins as small molecule BACE-1 Inhibitors: Explorations of the S3 pocket", AN 2007:883652; 234th ACS Conference Meeting Abstract; 2010 ACS on SciFinder.
Baxter, Ellen, et. al.; "BACE (Beta-Amyloid site Cleaving Enzyme, β-Secretase) Inhibitors for the treatment of Alzheimer's disease"; AN 2007:883605; 234th ACS Conference Meeting Abstract; 2010 ACS on SciFinder.
Albert, Jeffrey S.; et. al.; "Fragment based lead generation approaches for inhibitors of beta-secretase: Development of a novel series of isocytosine-based inhibitors"; AN 2007:295744.
Yan, Yinfa; et. al.; Piperidinyl-2-aminohydatoin derivatives for the inhibition of beta-secretase; AN 2007:295742; 233rd ACS National Meeting Abstract; 2010 ACS on SciFinder.
Erdel, Jim; et. al.; "Carbocylic substituted aminohydatoins as BACE-1 Inhibitors"; AN 2007: 295741; 233rd ACS National Meeting Abstract; 2010 ACS on SciFinder.
Nowak, Pawei; et. al.; "Hit-to-lead optimization of aminohydantoins as b-Secretase Inhibitors"; AN 2007:295740; 233rd ACS National Meeting Abstract; 2010 ACS on SciFinder.
Malamas, Michael S.; et. al.; "Aminohydantoins as highly potent, selective and orally active BACE 1 Inhibitors", AN 2007-295667; 233rd Conference Meeting Abstract; 2010 ACS on SciFinder.
Malamas, Michael S.; et. al.; "Thienyl aminohydantoins as potent BACE1 Inhibitors", AN 2008:953770; 236th Conference Meeting Abstract; 2010 ACS on SciFinder.
Malamas, Michael S.; et. al.; "Pyrazinyl aminohydantoins as potent BACE1 Inhibitors", AN 2008:953771; 236th Conference Meeting Abstract; 2010 ACS on SciFinder.
Malamas, Michael S.; et. al.;"Pyrrolyl 2-aminopyridines as potent BACE1 Inhibitors", 238th Conference Meeting Abstract; 2010 ACS on SciFinder.
Zhou, Ping; et. al.; "Substituted-pyrrole 2-amino-3,5-dihydro-4H-imidazol-4-ones as highly potent BACE1 Inhibitors: Optimization of the S3 pocket"; 235th Conference Meeting Abstract; 2010 ACS on SciFinder.
Yan, Yinfa; et. al.; "Syntheses and biological properties of carbocylic substituted aminohydantoin derivatives", AN 2008:389811; 235th Conference Meeting Abstract; 2010 ACS on SciFinder.
Quagliato, Dominick; et. al.; "Rigid analogs of 4,4-diaryliminohydantoins as potent inhibitors of Beta-secretase", AN 2008:389810; 235th Conference Meeting Abstract; 2010 ACS on SciFinder.
Solvibile, William R.; et. al.; "2-Substituted-pyrrole 2-amino-3,5-dihydro-4H-imidazol-4-ones: Highly potent and selective BACE1 Inhibitors", AN 2008:389809; 235th Conference Meeting Abstract; 2010 ACS on SciFinder.

(56) References Cited

OTHER PUBLICATIONS

Erdel, Jim; et. al.; "N-Alkyl substituted-pyrrole 2-amino-3,5-dihydro-4H-imidazol-4-ones as potent, and selective BACE 1 Inhibitors", AN 2008:389808; 235th Conference Meeting Abstract; 2010 ACS on SciFinder.
Fobare, William F. et. al.; "Substituted-pyrrole 2-amino-3,5-dihydro-4h-imidazol-4-ones as highly potent and selective BACE1 Inhibitors", AN 2008:389736; 235th Conference Meeting Abstract; 2010 ACS on SciFinder.
Fan, Kristi Yi; et. al.; "Structure-based lead optimization of small molecule β-secretase(BACE1) Inhibitors", AN 2008:387238; 235th Conference Meeting Abstract; 2010 ACS on SciFinder.
Zhu, Zhaoning, et. al.; "Discovery of cyclic-aclguanidines as potent and selective BACE1 Inhibitors", AN 2009: 984464; 238th Conference Meeting Abstract; 2010 ACS on SciFinder.
Cuming, Jared, et. al.; Optimization of the iminohydantoin series of BACE1 Inhibitors. Part 4: Explorations of the F'subsite in the C5-aryl series; AN 2009:984451; 2010 ACS on SciFinder.
Smith, Elizabeth, et. al.; "Optimization of the iminohydantoin series of BACE1 Inhibitors. Part 5: Exploration of the S1' and S2-S3 binding sites"; AN 2009:984450; 238th Conference Meeting Abstract; 2010 ACS on SciFinder.
Mazzola, Robert, D.; et. al.; "Design and synthesis of novel iminohydatoin β-secretase (BACE) Inhibitors. Part 3: Discovery and Exploration of the A-site"; AN 2009:984449; 238th Conference Meeting Abstract; 2010 ACS on SciFinder.
Mazzola, Robert, D.; et. al.;"Novel iminopyrimidinone β-secretase (BACE)Inhibitors: Part 3: C5 Substititution"; AN 2010:345058; 239th Conference Meeting Abstract; 2010 ACS on SciFinder.
Caldwell, John, et. al.; Design and synthesis of novel iminohydatoin β-secretase (BACE) Inhibitors. Part 2: The S1 to S3 approach; AN 2009:984447; 238th Conference Meeting Abstract; 2010 ACS on SciFinder.
Sun Zhong-Yue, et. al.; "2-iminohydatoin as potential BACE1 Inhibitors"; AN 2009:984446; 238th Conference Meeting Abstract; 2010 ACS on SciFinder.
Efremov, Ivan V., et. al.; "Identificaiton of spirocycli pyrrolidines as novel BACE Inhibitors"; AN2010:345057; 239th Conference Meeting Abstract; 2010 ACS on SciFinder.
Iserloh, Ulrich; et. al.; Novel iminopyrimidinone β-secretase (BACE)Inhibitors: Part 2. P1-azoles AN 2010:345056; 239th Conference Meeting Abstract; 2010 ACS on SciFinder.
Robichaud, Albert J.; et. al.; Identification of selective BACE1 inhibitors as potential disease modifying treatments for Alzheimer's disease: AN 2010:344829; 239th Conference Meeting Abstract; 2010 ACS on SciFinder.
Brodney, Michael A.; et. al.; "Beta-secretase inhibitors for the treatment of Alzheimer's disease", AN2010:344828; 239th Conference Meeting Abstract; 2010 ACS on SciFinder.
Stamford, Andrew.W.; et. al.; "Discovery of small molecule, orally active and brain penetrant BACE 1 Inhibitors", AN 2010: 344827; 239th Conference Meeting Abstract; 2010 ACS on SciFinder.
O'Neill, Brian T.; et. al.; "Pyrrolidine ss-secretase inhibitors for the treatment of Alzheimer's disease", AN 2010: 344728; 239th Conference Meeting Abstract; 2010 ACS on SciFinder.
Cumming, Jared N.; Novel iminopyrimidinone β-secretase (BACE)Inhibitors: Part 1, P1-P3 SAR; AN 2010:344544; 239th Conference Meeting Abstract; 2010 ACS on SciFinder.
Keana, John F.W.; et. al."Synthetic Intermediates Potentially Useful for the Synthesis of Tetrodotoxin and Derivatives", Journal of Organic Chemistry; 1976, 41, No. 12; pp. 2124-2129.
Keana, John F.W.; et. al."Diels-Alder Reactions Involving Heterocyclic Dienophiles Synthesis of Substituted of Hydroquinazolines . . . "; Journal of Organic Chemistry; 1969, 34, No. 11; pp. 3705-3707.
Bolshaya Sovetskaya Entsicolpediya ("Great Russian Encycolopedia"), Moscow, 1976, vol. 25, p. 981.
N.A. Tukavkina, Yu.I. Baukov, Bioorganitcheskaya Khimiya (Bioorganic Chemistry), Moscow, "Meditsina" publishes, 1991, p. 54).

Sawanishi, Hiroyuku, Studies on diazepines, XXI. Photochemical synthesis of 1H-2,4-benzodiazepines from 4-azidoisoquinolines, Chemical & Pharmaceutical Bulletin (1985), 33 (10), 4564-71.
Kovtunenko, V. A., 2-Substituted 1-amino-3H-isoindolium salts, Ukranski Khimcheskii Zhurnal (Russian edition) (1984), 50 (5), 530-4.
Barret, P.A. Phthadocyanines and related compounds. XV. Tetrahbentriazapophin: its preparation from phthalonitrile and a proof of its structure, Journal of the Chemical Society (1939), 1809-20.
May, H. J. Chemistry and biological properties of substituted 3-aminio-1H-isoindoles, Aznetitted-Forschung (1980), 30 (9), 1487-93.
Shafik, R.M., Synthesis of novel 2-{2-(substituted amino) phenetyl]-1H-benzimidazoles, 3, 4-dihydro and 1,2,3,4-tetrahydrpyrimido[1,6-a]benzimidazoles as potential antiulcer agents, Pharmazie (2004), 59 (12), 899-905.
Arnold, Michael A., Diastereoselective [4+2] Annulation of Vinyl Carbodimides wit N-Alkyl Imines. Asymmetric Synthetic Access to the Batzelladine Alkaloids, Journal of the American Chemical Society (2005), 127 (19), 6924-6925.
Cohen, Frederick, Enantioselective total synthesis of batzelladine F: structural revision and stereochemical definition, Journal of the American Chemical Society (2001), 123 (43), 10782-10783.
Overman, Larry E., Synthesis of Polycyclic Guanidines by Cyclocondensation Reactions of N-Amidinyliminium Ions, Journal of Organic Chemistry (2001), 66 (9), 3167-3175.
Franklin, Alison S. Application of the Tethered Biginelli Reaction for Enantioselectives Synthesis of Batzelladine Alkaloids. Absolute Configuration of the Tricyclic Guanidines Portion of Batzelladines B, Journal of Organic Chemistry (1999), 64 (5), 1512-1519.
Clemens, Andrea. Studies on the chemistry of isoindoles and isoindolenines, Part XXXX. 3-hydroximino-1-alkyl(aryl)isoindolines and 3-hydroxylaminio-1-alkyl(aryl)-1H-isoindoles. Model compounds for investigations of structure and reactivity, Zeitschrift Fuer Naturforschung, B. Chemical Science (1996), 51 (12), 1791-1810.
Katritzky, Alan R. Agueous high-temperature chemistry of carbo- and heterocycles. 12 Benzonitriles and pyridinecarbonitriles, benzamides and pyridinecarboxamides, and benzylamines and pyridylamines, Energy and Guels (1990), 4 (5), 555-61.
Skala, Vratislav, Reaction of some dicyanoppyridines with methlymagnesium iodide. Nuclear Overhauser effect in the presence of NMR shift reagent, Collection of Czechoslovak Chemical Communications (1974), 39 (3), 834-841.
Nasakin, O.E. , Synthesis and anti-HIV activity of polynitriele derivatives, Khimiko-Farmatsevticheskii Zhurnal (1998), 32 (5), 21-23.
Na, et al., Aspartic proteases of *Plasmodium vivax* are highly conserved in wild isolates, Korean Journal of Prasitology (Jun. 2004), 42(2) 61-6. Journal Code: 9435800.
Moore et al., Purification of HTLV-I Protease and Synthesis of Inhibitors for the treatment of HTLV-I Invention, 55th South east Regional Meeting of the American Chemical Society, Atlanta GA, (Nov. 2003) 1073. CODEN; 69EUCH Conference, AN 2004:137641 CAPLUS (Abstract 5 Pages).
Oparil et al., The Renin-Angiotensin System (Second of Two Parts), The New England Journal of Medicine, (Aug. 1974), 291(9) 446-457.
U.S. Appl. No. 11/010,772, filed Dec. 13, 2004—325 Pages.
Baeyer, A. and Burkhardt, J. B.: Concerning the Diimidophthalien of Phenol; 2 pages of English Translation of the Chemical Laboratories of the Academy of Sciences in Munich, (1878).
Baeyer, A. and Burkhardt, J. B.: Concerning the Diimidophthalien of Phenol; From the Chemical Laboratories of the Academy of Sciences in Munich; German art; 3 pages, (1878).
Malamas, et al., Aminoimidazoles as Potent and Selective Human β-Secretas (BACE1) Inhibitors, J. Med. Chem. 2009, 52, 6314-6323.
Malamas, et al., Design and synthesis of aminohydantoins as potent and selective human b-secretase (BACE1) inhibitors with enhanced brain permeability, Bioorganic & Medicinal Chemistry Letters 20 (2010) 6597-6605.

(56) References Cited

OTHER PUBLICATIONS

Malamas, et al., Di-substituted pyridinyl aminohydantoins as potent and high selective human b-secretas (BACE1) Inhibitors, Bioorganic & Medical Chemistry 18 (2010) 630-639.

Malamas, et al., Design and Synthesis of 5,50-Disubstituted Aminohydantoins as Potent and Selective Human β-Secretas (BACE1) Inhibitors, J. Med. Chem. 2010, 53, 1146-1158.

Malamas, et al., Novel pyrrolyl 2-aminopyridines as potent and selective human b-secretase (BACE1) inhibitors, Bioorganic & Medicinal Chemistry Letters 20 (2010) 2068-2073.

Malamas, et al., New Pyrazolyl and thienyl aminohydantoins as potent BACE1 inhibitors: Exploring the S20 region, Bioorganic & Medicinal Chemistry Letters 21 (2011) 5164-5170.

Mandal, et al., Design and Validation of Bicyclic Iminopyrimidinones as Beta Amyloid Cleaving Enzyme-1 (BACE1) Inhibitors: Conformation Constraint to Favor a Bioactive Conformation, J. Med. Chem. 2012, 55, 9331-9345.

Nowak, et al. Discovery and initial optimization of 5, 50-disubstituted aminohydantoins as potent b-secretase (BACE1) inhibitors, Bioorganic & Medicinal Chemistry Letters 20 (2010) 632-635.

Probst, et al., Small-molecule BACE1 Inhibitors: a patent literature review (2006-2011), Expert Opinion on Therapeutic Patents, (2012) 22(5): 511-540.

Swahn, et al., Aminoimidazoles as BACE-1 inhibitors: The Challenge to achieve in vivo brain efficacy, Bioorganic & Medicinal Chemistry Letters 22 (2012) 1854-1859.

Swahn, et al., Design and Synthesis of β-Site Amyloid Precursor Protein Cleaving Enzyme (BACE1) Inhinitors with in Vivo Brain Reduction of β-Amyloid Peptides, J.Med. Chem. 2012, 55, 9346-9361.

Tresadern, et al., Rational design and synthesis of aminopiperazinones as b-secretase (BASE) inhibitors, Bioorganic & Medicinal Chemistry Letters 210(2011) 7255-7260.

* cited by examiner

SUBSTITUTED ISOINDOLINES AS ASPARTYL PROTEASE INHIBITORS

RELATED APPLICATIONS

This application claims priority to provisional application U.S. Ser. No. 60/690,541, filed on Jun. 14, 2005, herein incorporated by reference.

FIELD OF THE INVENTION

This invention relates to heterocyclic compounds, which function as aspartyl protease inhibitors, their preparation, pharmaceutical compositions comprising said compounds, their use in the treatment of cardiovascular diseases, cognitive and neurodegenerative diseases, and their use as inhibitors of the Human Immunodeficiency Virus, plasmepsins, cathepsin D and protozoal enzymes.

BACKGROUND

There are a number of aspartic proteases known to date, including pepsin A and C, renin, BACE, BACE 2, Napsin A, and cathepsin D, which have been implicated in pathological conditions.

The role of renin-angiotensin system (RAS) in regulation of blood pressure and fluid electrolyte has been well established (Oparil, S, et al. N Engl J Med 1974; 291:381-401/446-57). The octapeptide Angiotensin-II, a potent vasoconstrictor and stimulator for release of adrenal aldosterone, was processed from the precursor decapeptide Angiotensin-1, which in turn was processed from angiotensinogen by the renin enzyme. Angiotensin-II was also found to play roles in vascular smooth muscle cell growth, inflammation, reactive oxygen species generation and thrombosis, influence atherogenesis and vascular damage. Clinically, the benefit of interruption of the generation of angiotensin-II through antagonism of conversion of angiotensin-I has been well known and there are a number of ACE inhibitor drugs on the market. The blockade of the earlier conversion of angiotensinogen to angiotensin-I, i.e. the inhibition of renin enzyme, is expected to have similar but not identical effects. Since renin is an aspartyl protease whose only natural substrate is angiotensinogen, it is believed that there would be less frequent adverse effect for controlling high blood pressure and related symptoms regulated by angiotensin-II through its inhibition.

Another protease, Cathespin-D, is involved in lysosomal biogenesis and protein targeting, and may also be involved in antigen processing and presentation of peptide fragments. It has been linked to numerous diseases including, Alzheimer's, disease, connective tissue disease, muscular dystrophy and breast cancer.

Alzheimer's disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase activity responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result β-secretase activity, inhibition of BACE-1 should inhibit formation of Aβ peptides. Thus inhibition of BACE-1 is a therapeutic approach to the treatment of AD and other cognitive and neurodegenerative diseases caused by Aβ plaque deposition.

Human immunodeficiency virus (HIV), is the causative agent of acquired immune deficiency syndrome (AIDS). Traditionally, a major target for researchers has been HIV-1 protease, an aspartyl protease related to renin. It has been clinically demonstrated that compounds such as indinavir, ritonavir and saquinavir which are inhibitors of the HIV aspartyl protease result in lowering of viral load. As such, the compounds described herein would be expected to be useful for the treatment of AIDS.

In addition, Human T-cell leukemia virus type I (HTLV-I) is a human retrovirus that has been clinically associated with adult T-cell leukemia and other chronic diseases. Like other retroviruses, HTLV-I requires an aspartyl protease to process viral precursor proteins, which produce mature virions. This makes the protease an attractive target for inhibitor design. (Moore, et al. Purification of HTLV-I Protease and Synthesis of Inhibitors for the treatment of HTLV-I Infection, 55$^{th}$ Southeast Regional Meeting of the American Chemical Society, Atlanta, Ga., US Nov. 16-19, 2003 (2003), 1073. CODEN; 69EUCH Conference, AN 2004:137641 CAPLUS.)

Plasmepsins are essential aspartyl protease enzymes of the malarial parasite. Compounds for the inhibition of aspartyl proteases plasmepsins, particularly I, II, IV and HAP, are in development for the treatment of malaria. (Freire, et al. WO 2002074719. Na Byoung-Kuk, et al. Aspartic proteases of *Plasmodium vivax* are highly conserved in wild isolates Korean Journal of Prasitology (2004 June), 42(2) 61-6. Journal code: 9435800.) Furthermore, compounds used to target aspartyl proteases plasmepsins (e.g. I, II, IV and HAP), have been used to kill malarial parasites, thus treating patients thus afflicted. Certain compounds also exhibited inhibitory activity against Cathespin D.

Compounds that act as aspartyl protease inhibitors are described, for example in application U.S. Ser. No. 11/010, 772, filed on Dec. 13, 2004, herein incorporated by reference.

WO/9304047, herein incorporated by reference, describes compounds having a quinazolin-2-(thi)one nucleus. The document alleges that the compounds described therein are inhibitors of HIV reverse transcriptase.

US Publication No. US 2005/0282826 A1, herein incorporated by reference, describes diphenylimidazopyrimidine or -imidazole amines, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognitive impairment, Down's syndrome, hereditary cerebral hemorrhage with amyloidosis of the Dutch type, cerebral amyloid angiopathy and degenerative dementia.

US Publication No. US 2005/0282825 A1, herein incorporated by reference, describes amino-5,5-diphenylimidazolones, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognitive impairment, Down's syndrome, hereditary cerebral hemorrhage with amyloidosis of the Dutch type, cerebral amyloid angiopathy and degenerative dementia.

Other publications that disclosed compounds that are useful for treating Alzheimer's disease include WO 2006/044492, which discloses spiropiperidine compounds that are said to be inhibitors of β-secretase, and WO 2006/041404, which discloses substituted amino compounds that are said to be useful for the treatment or prophylaxis of Aβ related pathologies. Both these publications are incorporated by reference.

SUMMARY OF THE INVENTION

The present invention relates to compounds having the structural formula I

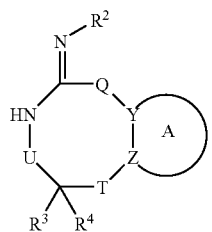

I or a stereoisomer, tautomer, or pharmaceutically acceptable salt or solvate thereof, wherein Q is a bond or —N($R^5$)—;
T is a bond, —O—, —C(O)—; —S—, —N($R^5$)—, —S(O)—, —S(O)$_2$— or —C($R^{6'}R^{7'}$)—;
U is a bond or —C($R^6$)($R^7$)—;
Y is C or N;
Z is C or N;
ring A, including variables Y and Z, is a three- to nine-membered cycloalkyl, cycloalkenyl, heterocyclyl, heterocyclenyl, aryl, and heteroaryl ring having 0 to 7, preferably 0 to 4, heteroatoms independently selected from the group consisting of O, S, N and —N(R)—, wherein ring A is unsubstituted or substituted with 1 to 5 independently selected $R^1$ moieties and/or oxo when ring A is cycloalkyl, cycloalkenyl, heterocyclyl or heterocyclenyl;

where,
R is independently selected from the group consisting of hydrogen, alkyl, alkenyl, alkynyl, cycloalkyl, cycloalkenyl, aryl, arylalkyl, heterocycloalkyl, heterocycloalkylalkyl, heteroaryl, heteroarylalkyl, arylcycloalkyl, —OR$^{15}$, —C(O)R$^8$, —C(O)OR$^9$, —S(O)R$^{10}$, —S(O)$_2$R$^{10}$, —C(O)N(R$^{11}$)(R$^{12}$), —S(O)$_2$N(R)(R$^{12}$), and —S(O)$_2$N(R$^{11}$)(R$^{12}$);

$R^1$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —S(O)$_{0-2}$R$^{15}$, —S(O)N(R$^{15}$)(R$^{16}$), S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), and —N(R$^{15}$)C(O)OR$^{16}$; and optionally:

i) when ring A is disubstituted with two $R^1$ groups on the same carbon atom, the two $R^1$ groups together with the ring carbon atom form a 3- to 7-membered cycloalkyl, cycloalkenyl, heterocyclyl or heterocyclenyl ring having 0 to 4, preferably 0 to 2, heteroatoms, independently selected from the group consisting of O, N, S, or —N(R)—, which is optionally substituted by 1 to 5 $R^{14}$ groups; or ii) when ring A is disubstituted with either: a) two $R^1$ groups; or b) a R group and a $R^1$ group, the two $R^1$ groups or the R group and $R^1$ group together with the ring A atoms to which they are attached form a 3- to 7-membered cycloalkyl, cycloalkenyl, heterocyclyl, heterocyclenyl, aryl or heteroaryl ring having 0 to 4, preferably 0 to 2 heteroatoms, independently selected from the group consisting of O, N, S, or —N(R)—, which is optionally substituted by 1 to 5 $R^{14}$ groups;

$R^2$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heterocycloalkyl, arylheterocycloalkyl, heteroarylheterocycloalkyl, alkenyl, arylalkenyl, cycloalkenyl, arylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —OR$^{15}$, —CN, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^8$)$_2$;

$R^3$, $R^4$, $R^6$ and $R^7$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heterocycloalkyl, arylheterocycloalkyl, heterocycloalkyl, heterocycloalkyl, arylheterocycloalkyl, heterocycloalkyl, heteroarylheterocycloalkyl, alkenyl, arylalkenyl, cycloalkenyl, arylcycloalkenyl, heterocycloalkenyl, arylheterocycloalkenyl, heteroarylheterocycloalkenyl, heterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^{11}$)(R$^{12}$), —SR$^{19}$, —S(O)$_2$N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S (O)R$^{10}$, —N(R$^{11}$)S(O)$_2$R$^{10}$—, —N(R$^{11}$)C(O)N(R$^{12}$)(R$^{13}$), —N(R$^{11}$)C(O)OR$^9$ and —C(=NOH)R$^8$;

and optionally, (i) R$^3$ and R$^4$, together with the carbon to which they are attached, form a 3- to 8-membered cycloalkyl, cycloalkenyl, heterocyclyl, heterocyclenyl, aryl or heteroaryl ring having 0 to 3 heteroatoms independently selected from the group consisting of O, N, S, and —N(R)—, which is optionally substituted by 1 to 5 R$^{14}$ groups and/or oxo, when said ring is cycloalkyl, cycloalkenyl, heterocyclyl, or heterocyclenyl ring;

(ii) R$^6$ and R$^7$, together with the carbon to which they are attached form a 3- to 8-membered cycloalkyl, cycloalkenyl, heterocyclyl, heterocyclenyl, aryl or heteroaryl ring having 0 to 3 heteroatoms independently selected from the group consisting of O, N, S, or —N(R)—, which is optionally substituted by 1 to 5 R$^{14}$ groups and/or oxo, when said ring is cycloalkyl, cycloalkenyl, heterocyclyl, or heterocyclenyl ring;

(iii) when U is —C(R$^6$)(R$^7$)—, R$^3$ and R$^6$ together with the carbon atoms to which they are attached form a 3- to 7-membered cycloalkyl, cycloalkenyl, heterocyclyl, heterocyclenyl, aryl or heteroaryl ring having 0 to 4, preferably 0 to 2 heteroatoms, independently selected from the group consisting of O, N, S, or —N(R)—, which is optionally substituted by 1 to 5 R$^{14}$ groups and/or oxo when said ring is cycloalkyl, cycloalkenyl, heterocyclyl, or heterocyclenyl ring;

(iv) when T is —C(R$^{6'}$)(R$^{7'}$)—, R$^3$ and R$^{6'}$ together with the carbon atoms to which they are attached form a 3- to 7-membered cycloalkyl, cycloalkenyl, heterocyclyl, heterocyclenyl, aryl or heteroaryl ring having 0 to 4, preferably 0 to 2 heteroatoms, independently selected from the group consisting of O, N, S, or —N(R)—, which is optionally substituted by 1 to 5 R$^{14}$ groups and/or oxo when said ring is a cycloalkyl, cycloalkenyl, heterocyclyl, or heterocyclenyl ring;

(v) when T is —N(R$^5$)—, R$^3$ and R$^5$ together with the atoms to which they are attached form a 3- to 7-membered heterocyclyl, heterocyclenyl, heteroaryl ring having 1 to 4, preferably 1 to 2, heteroatoms, independently selected from the group consisting of O, N, S, or —N(R)—, which is optionally substituted by 1 to 5 R$^{14}$ groups and/or by oxo when said ring is heterocyclyl, or a heterocyclenyl ring; or (vi) a) R$^3$ and R$^4$, together with the carbon to which they are attached, or b) R$^6$ and R$^7$, together with the carbon to which they are attached, form one of the following multicyclic groups:

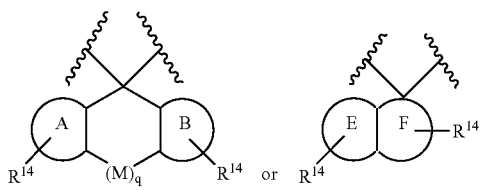

wherein:
M is independently —(CH$_2$)—, —S—, —N(R$^{19}$)—, —O—, —S(O)—, —S(O)$_2$—, or —C(O)—;
q is 0, 1, or 2;
A and B are independently aryl, heteroaryl, cycloalkyl, cycloalkenyl or heterocyclyl;
E is aryl or heteroaryl; and
F is cycloalkyl, cycloalkenyl, heterocyclyl or heterocyclenyl provided that there are no adjacent oxygen and/or sulfur atoms present in the ring system and further provided that both (a) R$^3$ and R$^4$; and (b) R$^6$ and R$^7$ cannot be combined to form said multicyclic groups:

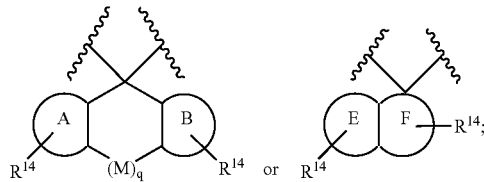

at the same time, preferably, a) R$^3$ and R$^4$, together with the carbon to which they are attached, or b) R$^6$ and R$^7$, together with the carbon to which they are attached, form one of the following multicyclic groups

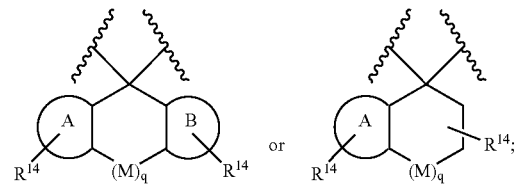

wherein
M is —CH$_2$—, —S—, —N(R$^{19}$)—, —O—, —CH$_2$—CH$_2$—, —CH=CH—, —CH$_2$—S—, —CH$_2$—O—, —O—CH$_2$—, —S—CH$_2$—, —CH$_2$—N(R$^{19}$)— or —N(R$^{19}$)—CH$_2$—
A and B are independently aryl or heteroaryl,
q is 0 or 1, provided that both (a) R$^3$ and R$^4$; and (b) R$^6$ and R$^7$ cannot be combined to form said multicyclic groups:

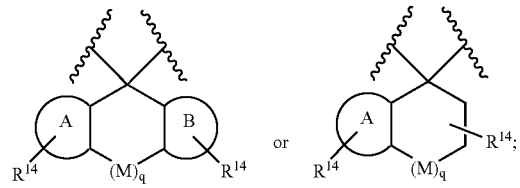

at the same time,
and provided that when there are at least two heteroatoms present, there cannot be any adjacent oxygen and/or sulfur atoms present in the above-described ring systems.

R$^5$ is selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —CH$_2$—O—Si(R$^9$)(R$^{10}$)(R$^{19}$), —CN, —C(O)R$^8$, —C(O)OR$^9$, —C(O)N($R^{11}$)($R^{12}$), —$SR^{19}$, —S(O)N($R^{11}$)($R^{12}$), —S(O)$_2$N($R^{11}$)($R^{12}$), —N($R^{11}$)($R^{12}$), —N($R^{11}$)C(O)$R^8$, —N($R^{11}$)S(O)$R^{10}$, —N($R^{11}$)S(O)$_2R^{10}$—, —N($R^{11}$)C(O)N($R^{12}$)($R^{13}$), —N($R^{11}$)C(O)$OR^9$ and —C(=NOH)$R^8$;

$R^{6'}$ and $R^{7'}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, -halo, —CH$_2$—O—Si($R^9$)($R^{10}$)($R^9$), —SH, —CN, —$OR^9$, —C(O)$R^8$, —C(O)$OR^9$, —C(O)N($R^{11}$)($R^{12}$), —$SR^{19}$, —S(O)N($R^{11}$)($R^{12}$), —S(O)$_2$N($R^{11}$)($R^{12}$), —N($R^{11}$)($R^{12}$), —N($R^{11}$)C(O)$R^8$, —N($R^{11}$)S(O)$R^{10}$, —N($R^{11}$)S(O)$_2R^{10}$—, —N($R^{11}$)C(O)N($R^{12}$)($R^{13}$), —N($R^{11}$)C(O)$OR^9$ and —C(=NOH)$R^8$;

or optionally $R^{6'}$ and $R^{7'}$ together with the carbon atom to which they are attached form a 3- to 8-membered cycloalkyl, cycloalkenyl, heterocyclyl, heterocyclenyl, aryl or heteroaryl ring having 0 to 3 heteroatoms independently selected from the group consisting of O, N, S, and —N(R)—, which is optionally substituted by 1 to 5 $R^{14}$ groups and/or oxo, when said ring is cycloalkyl, cycloalkenyl, heterocyclyl, or heterocyclenyl ring provided that when there are at least two heteroatoms present, there cannot be any adjacent oxygen and/or sulfur atoms present in the ring system;

$R^8$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, —$OR^{15}$, —N($R^{15}$)($R^{16}$), —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$) and —N($R^{15}$)C(O)$OR^{16}$;

$R^9$ is independently selected from the group consisting of H, alkyl, alkenyl, alkynyl, cycloalkyl, cycloalkylalkyl, heterocycloalkyl, heterocycloalkylalkyl, aryl, arylalkyl, heteroaryl and heteroarylalkyl;

$R^{10}$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl and —N($R^{15}$)($R^{16}$);

$R^{11}$, $R^{12}$ and $R^{13}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, —C(O)$R^8$, —C(O)$OR^9$, —S(O)$R^{10}$, —S(O)$_2R^{10}$, —C(O)N($R^{15}$)($R^{16}$), —S(O)N($R^{15}$)($R^{16}$), —S(O)$_2$N($R^{15}$)($R^{16}$) and —CN;

$R^{14}$ is 1-5 substituents independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —$OR^{15}$, —C(O)$R^{15}$, —C(O)$OR^{15}$, —C(O)N($R^{15}$)($R^{16}$), —$SR^{15}$, —S(O)N($R^{15}$)($R^{16}$), —S(O)$_2$N($R^{15}$)($R^{16}$), —C(=NOR$^{15}$)$R^1$, —P(O)(OR$^{15}$)(OR$^{16}$), —N($R^5$)($R^{16}$), —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$) and —N($R^{15}$)C(O)$OR^{16}$;

$R^{15}$, $R^{16}$ and $R^{17}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, arylheterocycloalkyl, $R^{18}$-alkyl, $R^{18}$-cycloalkyl, $R^{18}$-cycloalkylalkyl, $R^{18}$-heterocycloalkyl, $R^{18}$-heterocycloalkylalkyl, $R^{18}$-aryl, $R^{18}$-arylalkyl, $R^{18}$-heteroaryl and $R^{18}$-heteroarylalkyl; or $R^{15}$, $R^{16}$ and $R^{17}$ are

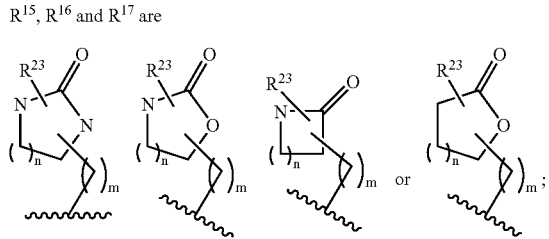

wherein $R^{23}$ numbers 0 to 5 substituents, m is 0 to 6 and n is 1 to 5;

$R^{18}$ is 1-5 substituents independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)$R^{19}$, —C(O)OH, —C(O)$OR^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —$SR^{19}$, —S(O)$_2R^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocycloalkyl), —S(O)$_2$N(alkyl)$_2$, —S(O)$_2$N(alkyl)(aryl), —OCF$_3$, —OH, —$OR^{20}$, —O-heterocycloalkyl, —O-cycloalkylalkyl, —O-heterocycloalkylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two $R^{18}$ moieties on adjacent carbons can be linked together to form

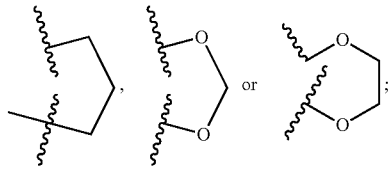

$R^{19}$ is alkyl, alkenyl, alkynyl, cycloalkyl, aryl, arylalkyl or heteroarylalkyl;

$R^{20}$ is alkyl, alkenyl, alkynyl, cycloalkyl, aryl, halo substituted aryl, arylalkyl, heteroaryl or heteroarylalkyl; and wherein:

i) each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkyl heteroaryl, cycloalkenylaryl, heterocycloalkenylaryl, in $R^2$, $R^3$, $R^4$, $R^5$, $R^6$, $R^{6'}$, $R^7$ and $R^{7'}$; and ii) each of the alkyl, cycloalkyl, cycloalkenyl, cycloalkylalkyl, heterocycloalkyl, heterocycloalkylalkyl, aryl, arylalkyl, arylcycloalkyl, heteroaryl, heteroarylalkyl, alkenyl and alkynyl groups in R, $R^1$, $R^8$, $R^9$, $R^{10}$, $R^{11}$, $R^{12}$, $R^{13}$ and $R^{14}$ are independently unsubstituted or substituted by 1 to 5 $R^{21}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroaryl heterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, halo, —CN, —$OR^{15}$, —$C(O)R^{15}$, —$C(O)OR^{15}$, —$C(O)N(R^{15})(R^{16})$, —$SR^{15}$, —$S(O)N(R^{15})(R^{16})$, —$CH(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$CH_2$—$N(R^{15})C(O)N(R^{16})(R^{17})$, —$CH_2$—$R^{15}$; —$CH_2N(R^{15})(R^{16})$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, —$N_3$, —$NO_2$ and —$S(O)_2R^{15}$; and wherein each of the alkyl, cycloalkenyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{21}$ are independently unsubstituted or substituted by 1 to 5 $R^{22}$ groups independently selected from the group consisting of alkyl, alkenyl, alkynyl, cycloalkyl, cycloalkenyl, heterocycloalkyl, aryl, heteroaryl, halo, —$CF_3$, —CN, —$OR^{15}$, —$C(O)R^{15}$, —$C(O)OR^{15}$, -alkyl-$C(O)OR^{15}$, $C(O)N(R^{15})(R^{16})$, —$SR^{15}$, —$S(O)N(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$N_3$, —$NO_2$, —$S(O)R^{15}$ and —$S(O)_2R^{15}$;

or two $R^{21}$ or two $R^{22}$ moieties on adjacent carbons can be linked together to form

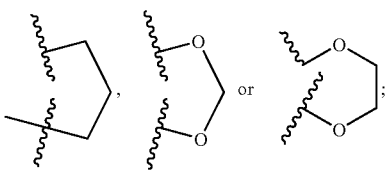

and when $R^{21}$ or $R^{22}$ are selected from the group consisting of —$C(=NOR^{15})R^{16}$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$ and —$CH_2$—$N(R^{15})C(O)OR^{16}$, $R^{15}$ and $R^{16}$ together can be a $C_2$ to $C_4$ chain wherein, optionally, one, two or three ring carbons can be replaced by —C(O)— or —N(H)— and $R^{15}$ and $R^{16}$, together with the atoms to which they are attached, form a 5 to 7 membered ring, optionally substituted by $R^{23}$;

$R^{23}$ is 1 to 5 groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —$OR^{24}$, —$C(O)R^{24}$, —$C(O)OR^{24}$, —$C(O)N(R^{24})(R^{25})$, —$SR^{24}$, —$S(O)N(R^{24})(R^{25})$, —$S(O)_2N(R^{24})(R^{25})$, —$C(=NOR^{24})R^{25}$, —$P(O)(OR^{24})(OR^{25})$, —$N(R^{24})(R^{25})$, -alkyl-$N(R^{24})(R^{25})$, —$N(R^{24})C(O)R^{25}$, —$CH_2$—$N(R^{24})C(O)R^{25}$, —$N(R^{24})S(O)R^{25}$, —$N(R^{24})S(O)_2R^{25}$, —$CH_2$—$N(R^{24})S(O)$ 25-$N(R^{24})S(O)_2N(R^{25})(R^{26})$, —$N(R^{24})S(O)N(R^{25})(R^{26})$, —$N(R^{24})C(O)N(R^{25})(R^{26})$, —$CH_2$—$N(R^{24}C(O)N(R^{25})(R^{26})$, —$N(R^{24})C(O)OR^{25}$, —$CH_2$—$N(R^{24})C(O)OR^{25}$, —$S(O)R^{24}$ and —$S(O)_2R^{24}$; and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{23}$ are independently unsubstituted or substituted by 1 to 5 $R^{27}$ groups independently selected from the group consisting of alkyl, cycloalkyl, heterocycloalkyl, aryl, heteroaryl, halo, —$CF_3$, —CN, —$OR^{24}$, —$C(O)R^{24}$, —$C(O)OR^{24}$, alkyl-$C(O)OR^{24}C(O)N(R^{24})(R^{25})$, —$SR^{24}$, —$S(O)N(R^{24})(R^{25})$, —$S(O)_2N(R^{24})(R^{25})$, —$C(=NOR^{24})R^{25}$, —$P(O)(OR^{24})(R^{25})$, —$N(R^{24})(R^{25})$, -alkyl-$N(R^{24})(R^{25})$, —$N(R^{24})C(O)R^{25}$, —$CH_2$—$N(R^{24})C(O)R^{25}$, —$N(R^{24})S(O)R^{25}$, —$N(R^{24})S(O)_2R^{25}$, —$CH_2$—$N(R^{24})S(O)R^{25}$, —$N(R^{24})S(O)_2N(R^{25})(R^{26})$, —$N(R^{24})S(O)N(R^{25})(R^{26})$, —$N(R^{24})C(O)N(R^{25})(R^{26})$, —$CH_2$—$N(R^{24}C(O)N(R^{25})(R^{26})$, —$N(R^{24})C(O)OR^{25}$, —$CH_2$—$N(R^{24})C(O)OR^{25}$, —$S(O)R^{24}$ and —$S(O)_2R^{24}$;

$R^{24}$, $R^{25}$ and $R^{26}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, $R^{27}$-alkyl, $R^{27}$-cycloalkyl, $R^{27}$-cycloalkylalkyl, $R^{27}$-heterocycloalkyl, $R^{27}$-heterocycloalkylalkyl, $R^{27}$-aryl, $R^{27}$-arylalkyl, $R^{27}$-heteroaryl and $R^{27}$-heteroarylalkyl;

$R^{27}$ is 1-5 substituents independently selected from the group consisting of alkyl, alkenyl, alkynyl, aryl, arylalkyl, —$NO_2$, halo, —$CF_3$, —CN, alkyl-CN, —$C(O)R^{28}$, —$C(O)OH$, —$C(O)OR^{28}$, —$C(O)NHR^{29}$, —$C(O)N(alkyl)_2$, —$C(O)N(alkyl)(aryl)$, —$C(O)N(alkyl)(heteroaryl)$, —$SR^{28}$, —$S(O)_2R^{29}$, —$S(O)NH_2$, —$S(O)NH(alkyl)$, —$S(O)N(alkyl)(alkyl)$, —$S(O)NH(aryl)$, —$S(O)_2NH_2$, —$S(O)_2NHR^{28}$, —$S(O)_2NH(aryl)$, —$S(O)_2NH(heterocycloalkyl)$, —$S(O)_2N(alkyl)_2$, —$S(O)_2N(alkyl)(aryl)$, —OH, —$OR^{29}$, —O-heterocycloalkyl, —O-cycloalkylalkyl, —O-heterocycloalkylalkyl, —$NH_2$, —$NHR^{29}$, —$N(alkyl)_2$, —$N(arylalkyl)_2$, —$N(arylalkyl)(heteroarylalkyl)$, —$NHC(O)R^{29}$, —$NHC(O)NH_2$, —$NHC(O)NH(alkyl)$, —$NHC(O)N(alkyl)(alkyl)$, —$N(alkyl)C(O)NH(alkyl)$, —$N(alkyl)C(O)N(alkyl)(alkyl)$, —$NHS(O)_2R^{29}$, —$NHS(O)_2NH(alkyl)$, —$NHS(O)_2N(alkyl)(alkyl)$, —$N(alkyl)S(O)_2NH(alkyl)$ and —$N(alkyl)S(O)_2N(alkyl)(alkyl)$;

$R^{28}$ is alkyl, alkenyl, alkynyl, cycloalkyl, arylalkyl or heteroarylalkyl; and $R^{29}$ is alkyl, alkenyl, alkynyl, cycloalkyl, arylalkyl, heteroaryl or heteroarylalkyl;

provided that:

i) when U is a bond, Q is a bond, Y is N, and Z is C, then T is not —$N(R^5)$—;

ii) when U is —$C(R^6)(R^7)$—, Q is a bond, Y is N, and Z is C, then T is not —$N(R^5)$—;

iii) when Q is —$N(R^5)$—, U is a bond, then T is not a bond;

iv) when Q is —N(R$^5$), T is a bond, Z is N and Y is C, then U is not a bond;

v) when Q is —N(R$^5$), Z is a N, Y is C and U is a bond, then T is not a bond, —C(O)—, or —C(R$^{6'}$)(R$^{7'}$)—; and vi) when R$^3$ and R$^4$ are both phenyl, then A is not

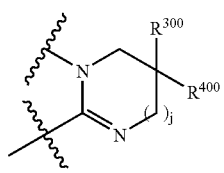

where

R$^{300}$ is H, an optionally substituted C$_1$-C$_4$ alkyl group, or together with the carbon to which it is attached and an adjacent ring carbon atom form a double bond;

R$^{400}$ is H or an optionally substituted C$_1$-C$_4$ alkyl group or

R$^{300}$ and R$^{400}$ are taken together and form a 3- to 7-membered ring optionally containing one or two heteroatoms optionally selected from O, N and S; and j is 0, 1, 2, or 3, and vii) when Q is NR$^5$ and T is a bond or —CR$^{6'}$R$^{7'}$, then

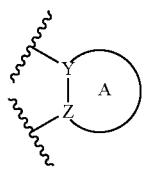

is not a 3- to 7-membered cycloalkyl or cycloalkylether ring.

This invention further provides for compounds of the formula:

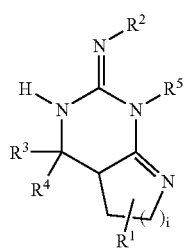

(II)

or a stereoisomer, tautomer, or pharmaceutically acceptable salt or solvate thereof, wherein R is independently selected from the group consisting of hydrogen, alkyl, alkenyl, alkynyl, cycloalkyl, cycloalkenyl, aryl, arylalkyl, heterocycloalkyl, heterocycloalkylalkyl, heteroaryl, heteroarylalkyl, arylcycloalkyl, —OR$^{15}$, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), and —S(O)$_2$N(R$^{11}$)(R$^{12}$);

R$^1$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —S(O)$_{0-2}$R$^{15}$, —S(O)N(R$^{15}$)(R$^{16}$), S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), and —N(R$^{15}$)C(O)OR$^{16}$;

R$^2$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —OR$^{15}$, —CN, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^8$)$_2$;

R$^3$ and R$^4$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^{18}$, —N(R$^{11}$)S(O)R$^{10}$, —N(R$^{11}$)S(O)$_2$R$^{10}$—, —N(R$^{11}$)C(O)N(R$^{12}$)(R$^{13}$), —N(R$^{11}$)C(O)OR$^9$ and —C(=NOH)R$^8$; and optionally, (i) R$^3$ and R$^4$, together with the carbon to which they are attached, form a 3- to 8-membered cycloalkyl, cycloalkenyl, heterocyclyl, heterocyclenyl, aryl or heteroaryl ring having 0 to 3 heteroatoms independently selected from the group consisting of O, N, S, and —N(R)—, which is optionally substituted by 1 to 5 R$^{14}$ groups and/or oxo, when said ring is cycloalkyl, cycloalkenyl, heterocyclyl, or heterocyclenyl ring; or (ii) a) R$^3$ and R$^4$, together with the carbon to which they are attached, form one of the following multicyclic groups:

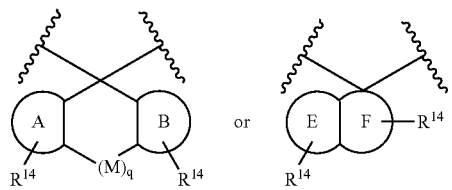

wherein:
M is independently —(CH$_2$)—, —S—, —N(R$^{19}$)—, —O—, —S(O)—, —S(O)$_2$—, or —C(O)—;
q is 0, 1, or 2;
A and B are independently aryl, heteroaryl, cycloalkyl, cycloalkenyl or heterocyclyl;
E is aryl or heteroaryl; and
F is cycloalkyl, cycloalkenyl, heterocyclyl or heterocyclenyl
provided that there are no adjacent oxygen and/or sulfur atoms present in the ring system; preferably, a) R$^3$ and R$^4$, together with the carbon to which they are attached, form one of the following multicyclic groups

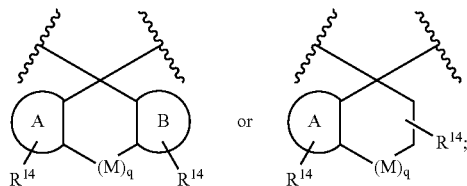

wherein
M is —CH$_2$—, —S—, —N(R$^{19}$)—, —O—, —CH$_2$—CH$_2$—, —CH═CH—, —CH$_2$—S—, —CH$_2$—O—, —O—CH$_2$—, —S—CH$_2$—, —CH$_2$—N(R$^{19}$)— or —N(R$^{19}$)—CH$_2$—
A and B are independently aryl or heteroaryl,
q is 0 or 1,
and provided that when there are at least two heteroatoms present, there cannot be any adjacent oxygen and/or sulfur atoms present in the above-described ring systems.

R$^5$ is selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —CH$_2$—O—Si(R$^9$)(R$^{10}$)(R$^{19}$), —CN, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$—, —N(R$^{11}$)C(O)N(R$^{12}$)(R$^{13}$), —N(R$^{11}$)C(O)OR$^9$ and —C(═NOH)R$^8$;

R$^8$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, —OR$^{15}$, N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

R$^9$ is independently selected from the group consisting of H, alkyl, alkenyl, alkynyl, cycloalkyl, cycloalkylalkyl, heterocycloalkyl, heterocycloalkylalkyl, aryl, arylalkyl, heteroaryl and heteroarylalkyl;

R$^{10}$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl and —N(R$^{15}$)(R$^{16}$);

R$^{11}$, R$^{12}$ and R$^{13}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$), —S(O)$_2$N(R$^{15}$)(R$^{16}$) and —CN;

R$^{14}$ is 1-5 substituents independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(═NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

R$^{15}$, R$^{16}$ and R$^{17}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, arylheterocycloalkyl, R$^{18}$-alkyl, R$^{18}$-cycloalkyl, R$^{18}$-cycloalkylalkyl, R$^{18}$-heterocycloalkyl, R$^{18}$-heterocycloalkylalkyl, R$^{18}$-aryl, R$^{18}$-arylalkyl, R$^{18}$-heteroaryl and R$^{18}$-heteroarylalkyl; or R$^{15}$, R$^{16}$ and R$^{17}$ are

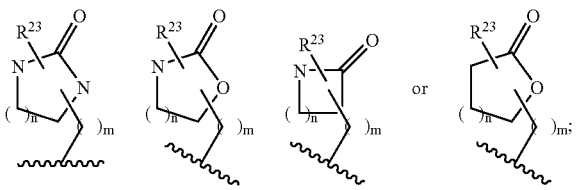

wherein R$^{23}$ numbers 0 to 5 substituents, m is 0 to 6 and n is 1 to 5;

R$^{18}$ is 1-5 substituents independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocycloalkyl), —S(O)$_2$N(alkyl)$_2$, —S(O)$_2$N(alkyl)(aryl), —OCF$_3$, —OH, —OR$^{20}$, —O-heterocycloalkyl, —O-cycloalkylalkyl, —O-heterocycloalkylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$ N(alkyl)(alkyl);

or two R$^{18}$ moieties on adjacent carbons can be linked together to form

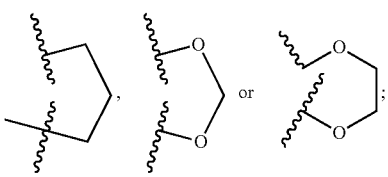

R$^{19}$ is alkyl, alkenyl, alkynyl, cycloalkyl, aryl, arylalkyl or heteroarylalkyl;

R$^{20}$ is alkyl, alkenyl, alkynyl, cycloalkyl, aryl, halo substituted aryl, arylalkyl, heteroaryl or heteroarylalkyl;

and wherein:

iii) each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylaryl, heterocycloalkenylaryl, in R$^2$, R$^3$, R$^4$, and R$^5$; and iv) each of the alkyl, cycloalkyl, cycloalkenyl, cycloalkylalkyl, heterocycloalkyl, heterocycloalkylalkyl, aryl, arylalkyl, arylcycloalkyl, heteroaryl, heteroarylalkyl, alkenyl and alkynyl groups in R, R$^1$, R$^8$, R$^9$, R$^{10}$, R$^{11}$, R$^{12}$, R$^{13}$ and R$^{14}$ are independently unsubstituted or substituted by 1 to 5 R$^{21}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heteroarylcycloalkylaryl, heteroaryl, cycloalkylheteroaryl, heterocycloalkylheteroaryl, cycloalkenylaryl, heterocycloalkenylaryl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, —N$_3$, —NO$_2$ and —S(O)$_2$R$^{15}$; and wherein each of the alkyl, cycloalkenyl, cycloalkyl, cycloalkylalkyl, heterocycloalkyl, heterocycloalkylalkyl, aryl, arylalkyl, heteroaryl, heteroarylalkyl, alkenyl and alkynyl groups in R$^{21}$ are independently unsubstituted or substituted by 1 to 5 R$^{22}$ groups independently selected from the group consisting of alkyl, alkenyl, alkynyl, cycloalkyl, cycloalkylalkyl, heterocycloalkyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, —NO$_2$, —S(O)R$^{15}$ and —S(O)$_2$R$^{15}$;

or two R$^{21}$ or two R$^{22}$ moieties on adjacent carbons can be linked together to form

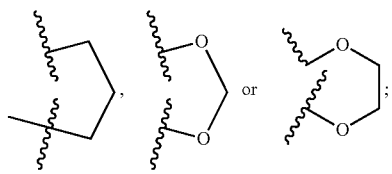

and when R$^{21}$ or R$^{22}$ are selected from the group consisting of —C(=NOR$^{15}$)R$^{16}$, —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$ and —CH$_2$—N(R$^{15}$)C(O)OR$^{16}$, R$^{15}$ and R$^{16}$ together can be a C$_2$ to C$_4$ chain wherein, optionally, one, two or three ring carbons can be replaced by —C(O)— or —N(H)— and R$^{15}$ and R$^{16}$, together with the atoms to which they are attached, form a 5 to 7 membered ring, optionally substituted by R$^{23}$;

R$^{23}$ is 1 to 5 groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{24}$, —C(O)R$^{24}$, —C(O)OR$^{24}$, —C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2^{24}$; and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in R$^{23}$ are independently unsubstituted or substituted by 1 to 5 R$^{27}$ groups independently selected from the group consisting of alkyl, cycloalkyl, heterocycloalkyl, aryl, heteroaryl, halo, —CF$_3$, —CN, —OR$^{24}$, —C(O)R$^{24}$, —C(O)OR$^{24}$, alkyl-C(O)OR$^{24}$, C(O)N(R$^{24}$)(R$^{25}$), —SR$^{24}$, —S(O)N(R$^{24}$)(R$^{25}$), S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), N(R$^{24}$)C(O)OR$^{25}$, —CH$_2$—N(R$^{24}$)C(O)OR$^{25}$, —S(O)R$^{24}$ and —S(O)$_2$R$^{24}$;

R$^{24}$, R$^{25}$ and R$^{26}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, R$^{27}$-alkyl, R$^{27}$-cycloalkyl, R$^{27}$-cycloalkylalkyl, $R^{27}$-heterocycloalkyl, $R^{27}$-heterocycloalkylalkyl, $R^{27}$-aryl, $R^{27}$-arylalkyl, $R^{27}$-heteroaryl and $R^{27}$-heteroarylalkyl;

$R^{27}$ is 1-5 substituents independently selected from the group consisting of alkyl, alkenyl, alkynyl, aryl, arylalkyl, —$NO_2$, halo, —$CF_3$, —CN, alkyl-CN, —C(O)$R^{28}$, —C(O)OH, —C(O)$OR^{28}$, —C(O)$NHR^{29}$, —C(O)N(alkyl)$_2$, —C(O)N(alkyl)(aryl), —C(O)N(alkyl)(heteroaryl), —$SR^{28}$, —S(O)$_2R^{29}$, —S(O)$NH_2$, —S(O)NH(alkyl), —S(O)N(alkyl)(alkyl), —S(O)NH(aryl), —S(O)$_2NH_2$, —S(O)$_2NHR^{28}$, —S(O)$_2$NH(aryl), —S(O)$_2$NH(heterocycloalkyl), —S(O)$_2$N(alkyl)$_2$, —S(O)$_2$N(alkyl)(aryl), —OH, —$OR^{29}$, —O-heterocycloalkyl, —O-cycloalkylalkyl, —O-heterocycloalkylalkyl, —$NH_2$, —$NHR^{29}$, —N(alkyl)$_2$, —N(arylalkyl)$_2$, —N(arylalkyl)(heteroarylalkyl), —NHC(O)$R^{29}$, —NHC(O)$NH_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{29}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

$R^{28}$ is alkyl, alkenyl, alkynyl, cycloalkyl, arylalkyl or heteroarylalkyl;

$R^{29}$ is alkyl, alkenyl, alkynyl, cycloalkyl, aryl, arylalkyl, heteroaryl or heteroarylalkyl; and i is 1, 2, or 3.

In another aspect, the invention relates to a pharmaceutical composition comprising at least one compound of formula I and/or II and a pharmaceutically acceptable carrier.

In another aspect, the invention comprises the method of inhibiting aspartyl protease comprising administering at least one compound of formula I and/or II to a patient in need of such treatment.

More specifically, the invention comprises: the method of treating a cardiovascular disease such as hypertension, renal failure, or a disease modulated by renin inhibition; the method of treating Human Immunodeficiency Virus; the method of treating a cognitive or neurodegenerative disease such as Alzheimer's Disease; the method of inhibiting plasmepins I and II for treatment of malaria; the method of inhibiting Cathepsin D for the treatment of Alzheimer's Disease, breast cancer, and ovarian cancer; and the method of inhibiting protozoal enzymes, for example inhibition of *plasmodium falciparnum*, for the treatment of fungal infections. Said method of treatment comprise administering at least one compound of formula I and/or II to a patient in need of such treatment. In particular, the invention comprises the method of treating Alzheimer's disease comprising administering at least one compound of formula I and/or II to a patient in need of such treatment.

In another aspect, the invention comprises the method of treating Alzheimer's disease comprising administering to a patient in need of such treatment a combination of at least one compound of formula I and/or II and a cholinesterase inhibitor or a modulator of muscarinic receptors, such as, but not limited to, a muscarinic m2 antagonist or an m1 muscarinic agonist.

Another aspect of this invention is pharmaceutical composition comprising an effective amount of a compound of formula I and/or II and at least one second pharmaceutical agent selected from the group consisting of beta secretase inhibitors; gamma secretase inhibitors; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; and promoters of alpha secretase activity and methods of treating the disease states associated with this compounds.

In a final aspect, the invention relates to a kit comprising in separate containers in a single package pharmaceutical compositions for use in combination, in which one container comprises a compound of formula I and/or II in a pharmaceutically acceptable carrier and a second container comprises a cholinesterase inhibitor or a muscarinic antagonist in a pharmaceutically acceptable carrier, the combined quantities being an effective amount to treat a cognitive disease or neurodegenerative disease such as Alzheimer's disease.

DETAILED DESCRIPTION

The terms used herein have their ordinary meaning and the meaning of such terms is independent at each occurrence thereof. That notwithstanding and except where stated otherwise, the following definitions apply throughout the specification and claims, Chemical names, common names and chemical structures may be used interchangeably to describe that same structure, These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", "alkoxy" etc.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. $R^{32}$-substituted alkyl groups include fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain.

Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" means an aromatic monocyclic or multicyclic ring system comprising about 6 to about 14 carbon atoms, preferably about 6 to about 10 carbon atoms. The aryl group can be optionally substituted with one or more substituents (e.g., $R^{18}$, $R^{21}R^{22}$, etc.) which may be the same or different, and are as defined herein or two substituents on adjacent carbons can be linked together to form

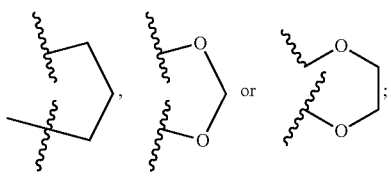

Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one to four of the ring atoms is an element other than carbon, for example nitrogen, oxygen or sulfur, alone or in combination. Preferred heteroaryls contain about 5 to about 6 ring atoms. The "heteroaryl" can be optionally substituted by one or more $R^{21}$ substituents which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more $R^{21}$ substituents which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Further non-limiting examples of cycloalkyl include the following

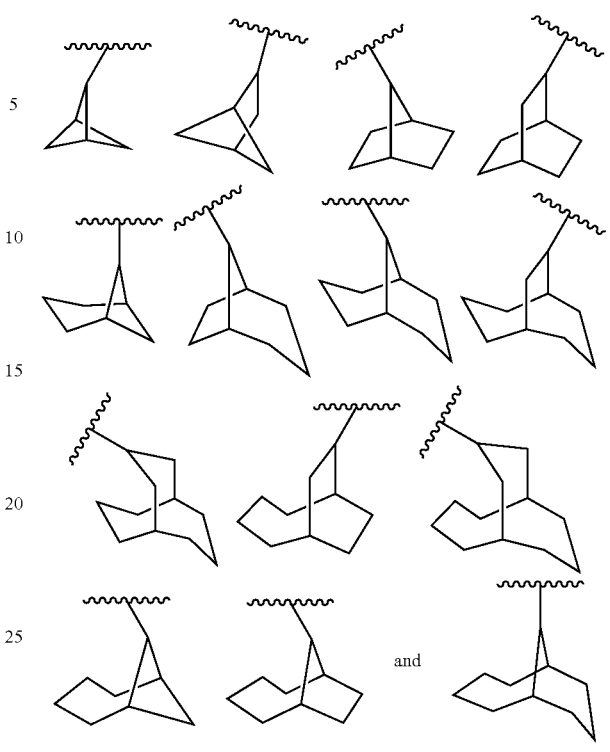

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkenyl" means a non-aromatic mono or multicyclic ring system comprising about 3 to about 10 carbon atoms, preferably about 5 to about 10 carbon atoms which contains at least one carbon-carbon double bond. The cycloalkenyl ring can be optionally substituted with one or more $R^{21}$ substituents which may be the same or different, and are as defined above. Preferred cycloalkenyl rings contain about 5 to about 7 ring atoms. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" (or "heterocycloalkeneyl") means a non-aromatic monocyclic or multicyclic ring system comprising about 3 to about 10 ring atoms, preferably about to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Heterocyclyl" (or "heterocycloalkyl") means a non-aromatic saturated monocyclic or multicyclic ring system comprising about 3 to about 10 ring atoms, preferably about 5 to about 10 ring atoms, in which 1-3, preferably 1 or 2 of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more $R^{21}$ substituents which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Arylcycloalkyl" means a group derived from a fused aryl and cycloalkyl as defined herein. Preferred arylcycloalkyls are those wherein aryl is phenyl and cycloalkyl consists of about 5 to about 6 ring atoms. The arylcycloalkyl can be optionally substituted by 1-5 $R^{21}$ substituents. Non-limiting examples of suitable arylcycloalkyls include indanyl and 1,2,3,4-tetrahydronaphthyl and the like. The bond to the parent moiety is through a non-aromatic carbon atom.

"Arylheterocycloalkyl" means a group derived from a fused aryl and heterocycloalkyl as defined herein. Preferred arylcycloalkyls are those wherein aryl is phenyl and heterocycloalkyl consists of about 5 to about 6 ring atoms. The arylheterocycloalkyl can be optionally substituted by 1-5 $R^{21}$ substituents. Non-limiting examples of suitable arylheterocycloalkyls include

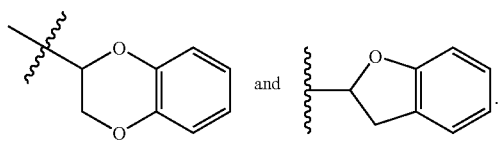 [SMILES: *C1COc2ccccc2O1 ; *C1Cc2ccccc2O1]

The bond to the parent moiety is through a non-aromatic carbon atom.

Similarly, "heteroarylalkyl" "cycloalkylalkyl" and "heterocycloalkylalkyl" mean a heteroaryl-, cycloalkyl- or heterocycloalkyl-alkyl-group in which the heteroaryl, cycloalkyl, heterocycloalkyl and alkyl are as previously described. It is also understood that the terms "arylcycloalkylalkyl", "heteroarylcycloalkylalkyl", "arylheterocycloalkylalkyl", "heteroarylheterocycloalkylalkyl", "heteroarylcycloalkyl", "heteroarylheterocycloalkyl", "arylcycloalkenyl", "heteroarylcycloalkenyl", "heterocycloalkenyl", "arylheterocycloalkenyl", "heteroarylheterocycloalkenyl", "cycloalkylaryl", "heterocycloalkylaryl", "heterocycloalkenylaryl", "heterocycloalkylheteroaryl", "cycloalkenylaryl" and "heterocycloalkenylaryl" similarly represented by the combination of the groups aryl-, cycloalkyl-, alkyl-, heteroaryl-, heterocycloalkyl-, cycloalkenyl- and heterocycloalkenyl- as previously described. Preferred groups contain a lower alkyl group. The bond to the parent moiety is through the alkyl.

"Acyl" means an H—C(O)—, alkyl-C(O)—, alkenyl-C(O)—, alkynyl-C(O)—, aryl-C(O)— or cycloalkyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkyoxyalkyl" means a group derived from an alkoxy and alkyl as defined herein. The bond to the parent moiety is through the alkyl.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more $R^{27}$ substituents. The bond to the parent moiety is through a non-aromatic carbon atom.

"Arylalkynyl" means a group derived from an aryl and alkenyl as defined herein. Preferred arylalkynyls are those wherein aryl is phenyl and the alkynyl consists of about 3 to about 6 atoms. The arylalkynyl can be optionally substituted by one or more $R^{27}$ substituents. The bond to the parent moiety is through a non-aromatic carbon atom.

The suffix "ene" on alkyl, aryl, heterocycloalkyl, etc. indicates a divalent moiety, e.g., —CH$_2$CH$_2$— is ethylene, and

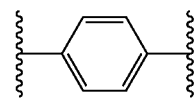

is para-phenylene.

The term "optionally substituted" means optional substitution with the specified groups, radicals or moieties, in available position or positions.

Substitution on a cycloalkylalkyl, heterocycloalkylalkyl, arylalkyl, or heteroarylalkyl moiety includes substitution on the ring portion and/or on the alkyl portion of the group.

When a variable appears more than once in a group, e.g., $R^8$ in —N(R$^8$)$_2$, or a variable appears more than once in the structure of formula I, e.g., $R^{15}$ may appear in both $R^1$ and $R^3$, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," or "at least one compound of formula II" one to three compounds of formula I or II can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line 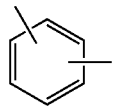 as a bond generally indicates a mixture of, or either of, the possible isomers, e.g., containing (R)— and (S)— stereochemistry. For example,

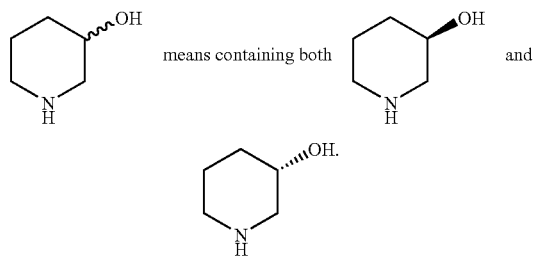

Lines drawn into the ring systems, such as, for example:

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, or heterocyclenyl ring, e.g.,

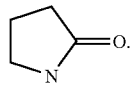

In this specification, where there are multiple oxygen and/or sulfur atoms in a ring system, there cannot be any adjacent oxygen and/or sulfur present in said ring system.

It is noted that the carbon atoms for formula I or II may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

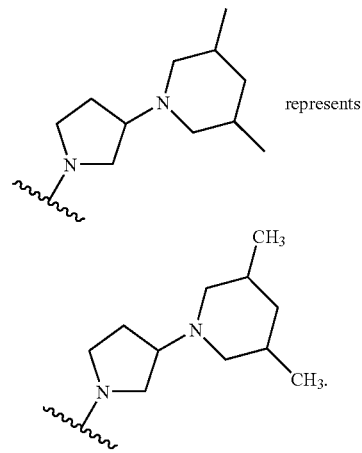 represents

It should also be noted that any heteroatom with unsatisfied valences in the text, schemes, examples, structural formulae, and any Tables herein is assumed to have the hydrogen atom or atoms to satisfy the valences.

Those skilled in the art will recognize that certain compounds of formula I are tautomeric, and all such tautomeric forms are contemplated herein as part of the present invention. For example, the compounds when Q is a bond and ring A including variables Y and Z is a benzene ring can be represented by

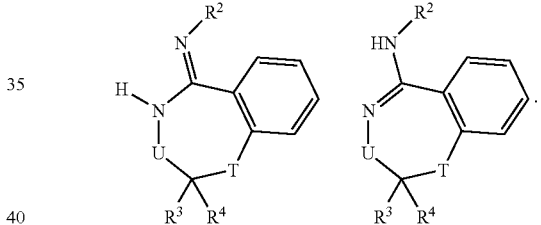

Similarly, compounds where Q is —N($R^5$)—, $R^5$ is H, and T is a bond can be represented by

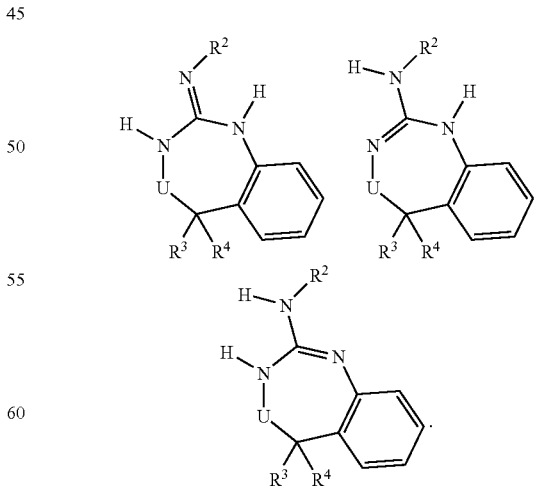

When $R^{21}$ and $R^{22}$, are, for example, —N($R^{15}$)C(O)N($R^{16}$)($R^{17}$) and $R^{15}$ and $R^{16}$ form a ring, the moiety formed, is, for example,

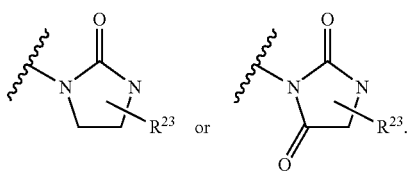

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula (I) or (II) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula (I) or (II) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) or (II) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

The compounds of formula I or (II) may exists in unsolvated as well as solvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting aspartyl protease and/or inhibiting BACE-1 and thus producing the desired therapeutic effect in a suitable patient.

The compounds of formula I or II form salts which are also within the scope of this invention. Reference to a compound of formula I or II herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I or II contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I or II may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. For example, if a compound of Formula (I) or (II) incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prod rug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) or (II) may be atropisomers (e.g., substituted biaryls) and are considered as part of this invention. Enantiomers can also be separated by use of chiral HPLC column.

Polymorphic forms of the compounds of formula I or II, and of the salts, solvates and prodrugs of the compounds of formula I or II, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) or (II) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of formula (I) or (II) can generally be prepared by following procedures analogous to those disclosed in the Schemes and/or in the Examples hereinbelow, by substituting an appropriate isotopically labelled reagent for a non-isotopically labelled reagent.

It should be noted that throughout the specification and Claims appended hereto any formula, compound, moiety or chemical illustration with unsatisfied valences is assumed to have the hydrogen atom to satisfy the valences unless the context indicates a bond.

Compounds of formula I, wherein the variables are as defined above, include the following independently preferred structures:

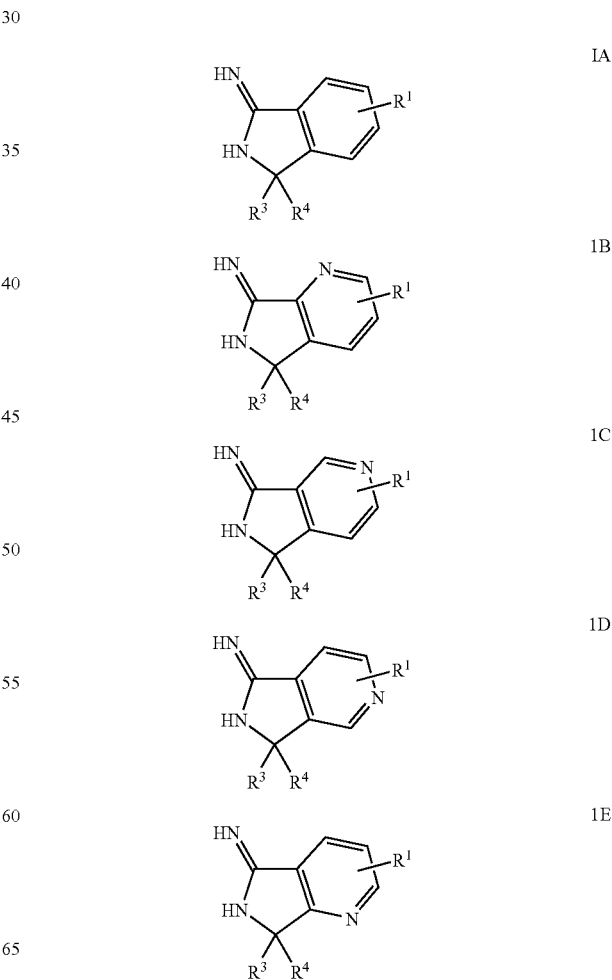

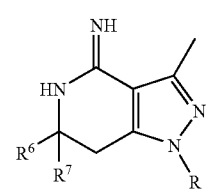
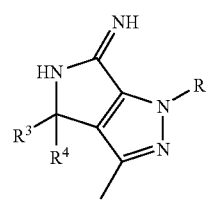
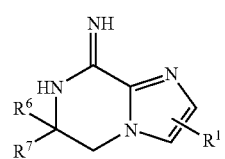
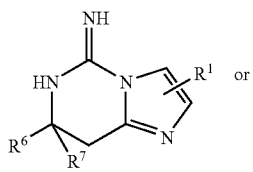
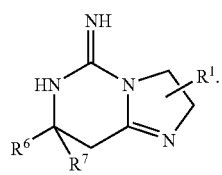
Another group of preferred compounds of formula I is that wherein R² is H.
Preferred embodiments for ring A include:
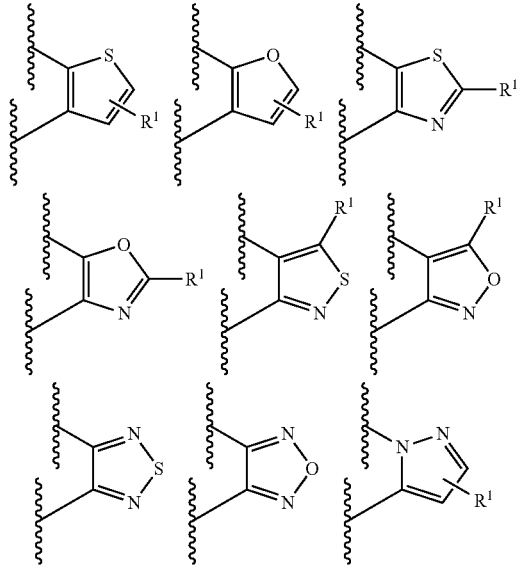
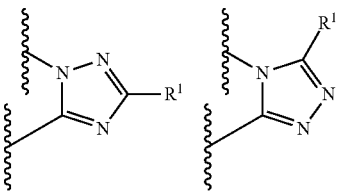
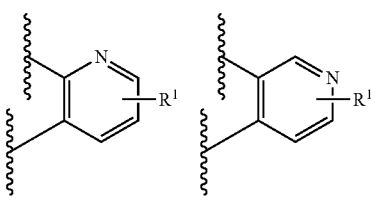
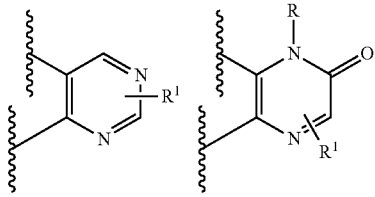
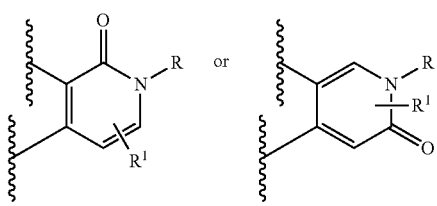
where preferably
R is hydrogen, lower alkyl, alkoxy, haloalkyl, cyano; and
R¹ is hydrogen, lower alkyl, halogen, alkoxy, haloalkyl, cyano.
In addition, preferred are embodiments of ring A which include:
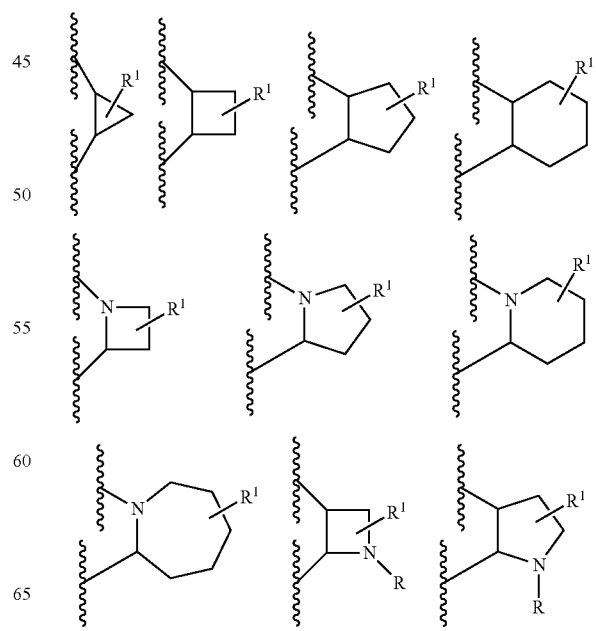

where
R is hydrogen, lower alkyl, alkoxy, haloalkyl, cyano; and
$R^1$ is hydrogen, lower alkyl, halogen, alkoxy, haloalkyl, cyano.

$R^3$, $R^4$, $R^6$, $R^{6'}$, $R^7$ and $R^{7'}$ are preferably selected from the group consisting of alkyl, cycloalkyl, cycloalkylalkyl, heterocycloalkyl, heterocycloalkylalkyl, aryl, arylalkyl, heteroaryl, heteroarylalkyl, halo, —$CH_2$—O—$Si(R^9)(R^{10})(R^{19})$, —SH, —CN, —$OR^9$, —$C(O)R^8$, —$C(O)OR^9$, —$C(O)N(R^{11})(R^{12})$, —$SR^{19}$, —$S(O)N(R^{11})(R^{12})$, —$S(O)_2N(R^{11})(R^{12})$, —$N(R^{11})(R^{12})$, —$N(R^{11})C(O)R^8$, —$N(R^{11})S(O)R^{10}$, —$N(R^{11})C(O)N(R^{12})(R^{13})$, —$N(R^{11})C(O)OR^9$ and —$C(=NOH)R^8$.

More preferably, $R^3$, $R^4$, $R^6$, $R^{6'}$, $R^7$ and $R^{7'}$ are preferably selected from the group consisting of aryl, heteroaryl, heteroarylalkyl, arylalkyl, cycloalkyl, heterocycloalkyl, heterocycloalkylalkyl, alkyl and cycloalkylalkyl.

In a group of preferred compounds
U is a bond;
$R^2$ is H;
$R^3$ is alkyl, cycloalkylalkyl, cycloalkyl, aryl, arylalkyl, $R^2$-alkyl, $R^{21}$-cycloalkylalkyl, $R^{21}$-cycloalkyl, $R^{21}$-aryl or $R^{21}$-arylalkyl;
$R^4$ is alkyl, cycloalkylalkyl, cycloalkyl, aryl, arylalkyl, $R^2$-alkyl, $R^2$-cycloalkylalkyl, $R^{21}$-cycloalkyl, $R^{21}$-aryl or $R^{21}$-arylalkyl;
In a group of preferred compounds $R^3$ or $R^4$ are alkyl or Additional groups of preferred compounds of formula I include those where:
a) U is —$C(R^6)(R^7)$—
$R^2$, $R^3$, $R^4$=H
T is a bond
Q is a bond;
b) U is —$C(R^6)(R^7)$—
$R^2$=H
$R^3$, $R^4$=H or alkyl;
c) T is a bond
Q is —$N(R^5)$—
Y is C
Z is C;
d) T is —$C(R^{6'})(R^{7'})$—, —O—, or —$N(R^5)$—
Q is a bond
U is —$C(R^6)(R^7)$—
$R^2$=H
$R^3$, $R^4$=H or alkyl
Y is C
Z is C; or
e) T is —$C(R^{6'})(R^{7'})$—
Q is $NR^5$
U is a bond
$R^2$=H
$R^3$, $R^4$=H or alkyl
Y is C
Z is C.

In an additional group of preferred compounds:
T is a bond;
U is a bond;
Q is a bond;
Y is C;
Z is C; and
ring A including Y and Z is $R^1$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —$OR^{15}$,
$R^2$ is H;
$R^3$ is alkyl, cycloalkylalkyl, cycloalkyl, aryl, arylalkyl, $R^{21}$-alkyl, $R^2$-cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl; and
$R^4$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl.

An additional group of preferred compounds of formula I are whose wherein
U is a bond;
Q is a bond;
T is —$C(R^{6'})(R^{7'})$—;
Y is N;
z is C; and
$R^2$ is H.

An even more preferred group of compound of this preferred group of compounds of formula are those compounds of the formula:

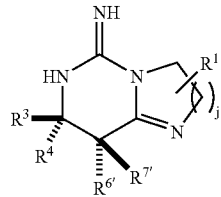
(III)

wherein
$R^3$ and $R^4$ are independently H, alkyl, aryl or heteroaryl; and
$R^{6'}$ and $R^{7'}$ are H, alkyl, aryl or heteroaryl.

An even more preferred group of compounds of formula III is those of the formula:

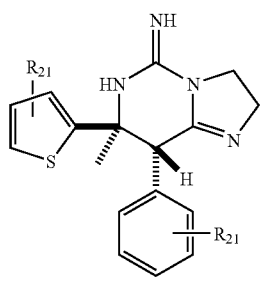
(III')

wherein $R^{21}$ is H, alkyl, halo, CN or —$OR^{24}$, where $R^{24}$ is H, alkyl, aryl or heteroaryl.

Especially preferred definitions for $R^{21}$ include phenyl wherein the phenyl moiety is optionally substituted by alkyl, optionally substituted phenyl or optionally substituted heteroaryl, wherein the optional substituents on the optionally substituted phenyl or optionally substituted heteroaryl are alkyl, halo, CN or —$OR^{24}$, where $R^{24}$ is H, alkyl, aryl or heteroaryl.

An especially preferred compound of formula II is:

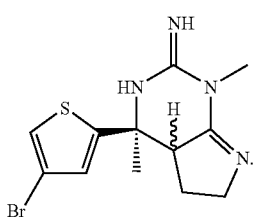
(II-A)

Compounds of formula I can be made using procedures known in the art. Preparative methods for preparing starting materials and compounds of formula I are show below as general reaction schemes followed by specific procedures, but those skilled in the art will recognize that other procedures can also be suitable. In the Schemes and in the Examples below, the following abbreviations are used: methyl: Me; ethyl: Et; propyl: Pr; butyl: Bu; benzyl: Bn; tertiary butyloxycarbonyl: Boc or BOC high pressure liquid chromatography: HPLC
liquid chromatography mass spectrometry: LCMS
thin layer chromatography: TLC
preparative thin layer chromatography: PTLC
room temperature: RT
hour: h
minute: min
retention time: $t_R$
N,N-dimethylformamide: DMF
N-bromosuccinimide: NBS
ethyl acetate: EtOAc
methanol: MeOH
trifluoroacetic acid: TFA
polymer-bound triphenylphosphine-Pd (0): PS-Ph$_3$P—Pd
meta chloroperbenzoic acid: mCPBA
trimethylsilyl cyanide: TMSCN
lithium diisopropylamide: LDA
1-(3-dimethylaminopropyl)-3-ethylcarbodiimide hydrochloride: EDCI
diisopropylethylamine: DIEA
diisopropyl azodicarboxylate: DIAD
Saturated (sat.); anhydrous. (anhyd); molecular weight (MW); milliliter (mL); gram (g). milligram (mg); equivalent (eq); day (d); microwave (μW); microliter(μL);

All NMR data were collected on 400 MHz NMR spectrometers unless otherwise indicated. For examples 1-7 LC-Electrospray-Mass spectroscopy with a C-18 column and 5% to 95% MeCN in water as the mobile phase was used to determine the molecular mass and retention time. The table contains the compounds with retention time/observed MW and/or NMR data.

For examples 8-21 HPLC retention times are reported under the conditions of a 6 minute gradient from 10% to 90% CH$_3$CN/H$_2$O with 0.05% TFA, 1.0 mL/min flow rate on an analytical C18 reverse-phase column.

For the synthesis of any particular compound, one skilled in the art will recognize that the use of protection groups may be required. A description of suitable protecting groups may be found in "Protective Groups in Organic Synthesis", 3$^{nd}$ Ed., John Wiley and Sons, New York (1999) by T. W. Greene In general, the compounds in the invention may be produced by variety of processes known to those skilled in the art and by known processes analogous thereto. The following reaction schemes serve as examples of these processes and illustrate routes to prepare specific embodiments; the practitioner is not limited to these methods.

One skilled in the art will recognize that one route will be optimized depending on the choice appendage substituents. Additionally, one skilled in the art will recognize that in some cases the order of steps has to be controlled to avoid functional group incomparability.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

General Methods of Preparing Compounds of Formula I

In the following reaction scheme, each variable may be any moiety within that variable's definition.

The compounds of formula IA can be synthesized according to Reaction Scheme I. Compound 1 is reacted with HCO$_2$H and HCONH$_2$ to yield compound 2. Compound 2 is then reacted with Et$_3$OBF$_4$ to give compound 3. Compound 3 is then reacted with sodium hydride and the halide R$^4$X, where X may be, for example Br or I to yield compound 4. Compound IA is formed by reacting compound 4 with ammonia and methanol.

Reaction Scheme 1

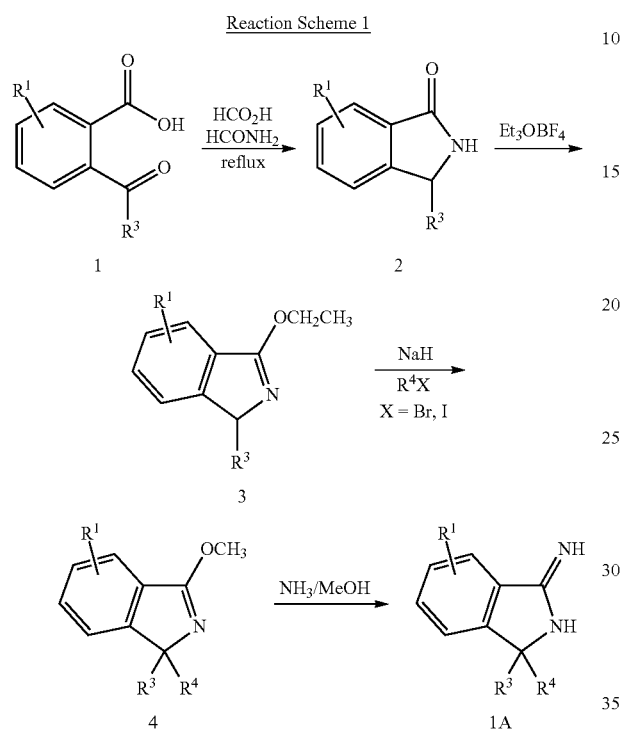

Compounds of formula IB can be prepared by Reaction Scheme 2. Compound 5, prepared by reacting acetoacetyl chloride with a methyl beta-amino carboxylate, is reacted with a base such as sodium methoxide in methanol to give compound 6. Compound 6 is reacted with H$_2$NNHR to give compound 7. Compound 7 is reacted with phosphorous pentasulfide to give compound 8, which is then reacted with methyl iodide and a base to give compound 9. Compound 9 is reacted with ammonia to give a compound of IB.

Reaction Scheme 2

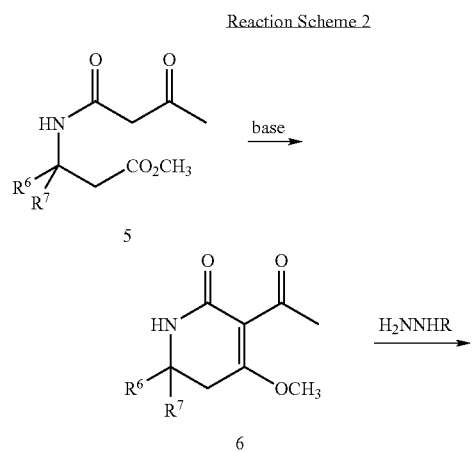

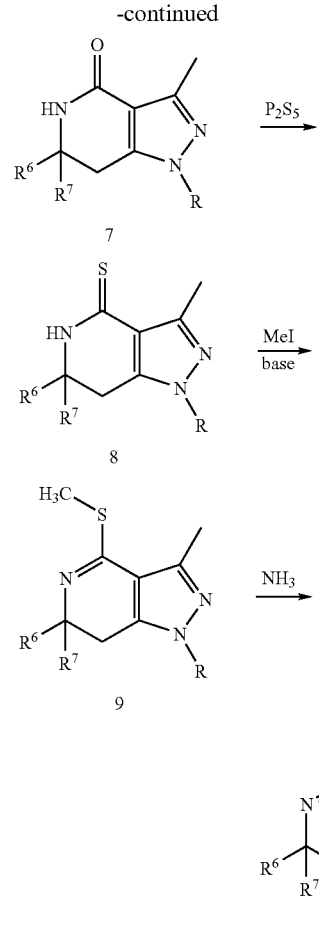

Compounds of formula 1C can be prepared following Reaction Scheme 3 by starting with ketone 10 and reacting it with 2-methyl-2-propanesulfinamide and titanium (IV) ethoxide give compound 11. Compound 11 is then reacted with compound 12 and ClTi(O-iPr)$_3$ to give compound 13, which is then reacted with a mineral acid, such as HCl to yield compound 14. Compound 14 is reacted with ethyl chlorooxoacetate and a base such as pyridine to yield compound 15, which is then cyclized in base such as sodium ethoxide in ethanol to form compound 16. Compound 16 is reacted with H$_2$NNHR to give compound 17. Reacting compound 17 with phosphorous pentasulfide gives compound 18. Compound 18 is then reacted with methyl iodide in the presence of a base such as sodium hydride to give compound 19. Compound 19 is then reacted with ammonia to give a compound of formula 1C.

Reaction Scheme 3

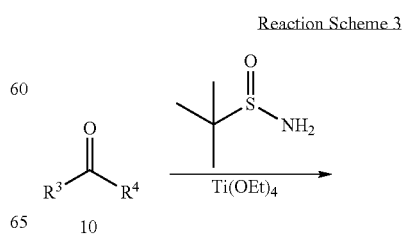

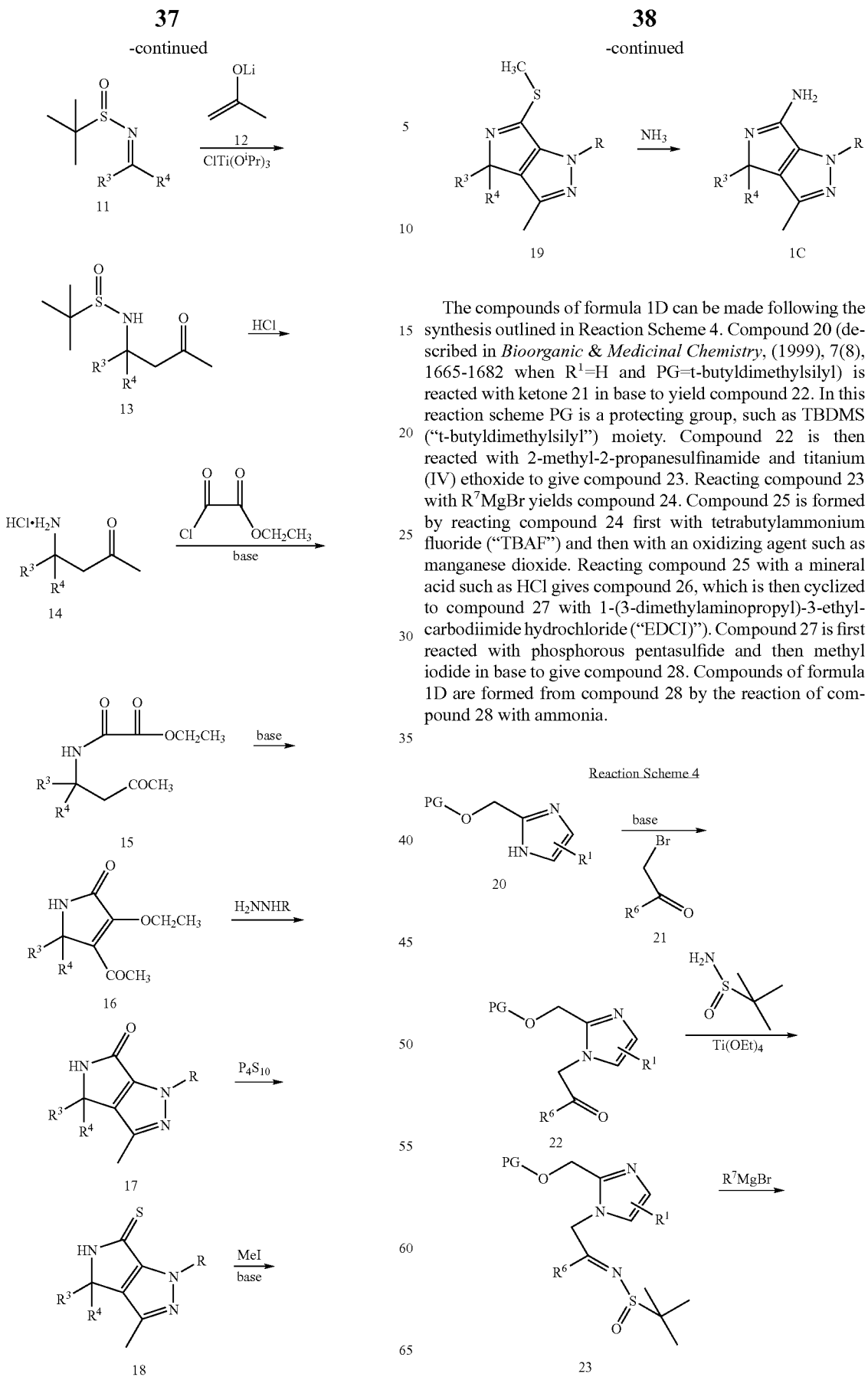

The compounds of formula 1D can be made following the synthesis outlined in Reaction Scheme 4. Compound 20 (described in *Bioorganic & Medicinal Chemistry*, (1999), 7(8), 1665-1682 when $R^1$=H and PG=t-butyldimethylsilyl) is reacted with ketone 21 in base to yield compound 22. In this reaction scheme PG is a protecting group, such as TBDMS ("t-butyldimethylsilyl") moiety. Compound 22 is then reacted with 2-methyl-2-propanesulfinamide and titanium (IV) ethoxide to give compound 23. Reacting compound 23 with $R^7$MgBr yields compound 24. Compound 25 is formed by reacting compound 24 first with tetrabutylammonium fluoride ("TBAF") and then with an oxidizing agent such as manganese dioxide. Reacting compound 25 with a mineral acid such as HCl gives compound 26, which is then cyclized to compound 27 with 1-(3-dimethylaminopropyl)-3-ethyl-carbodiimide hydrochloride ("EDCI"). Compound 27 is first reacted with phosphorous pentasulfide and then methyl iodide in base to give compound 28. Compounds of formula 1D are formed from compound 28 by the reaction of compound 28 with ammonia.

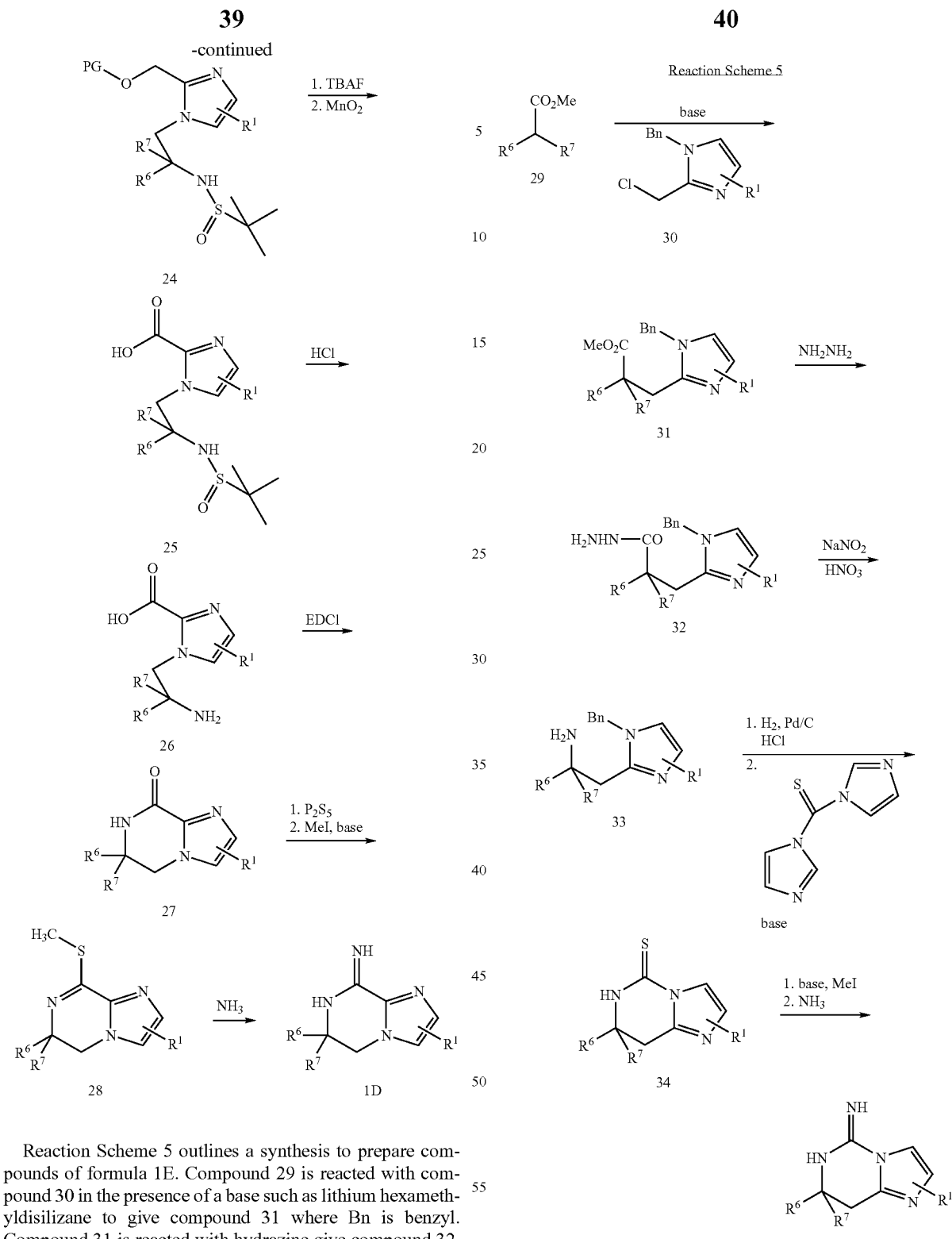

Reaction Scheme 5 outlines a synthesis to prepare compounds of formula 1E. Compound 29 is reacted with compound 30 in the presence of a base such as lithium hexamethyldisilizane to give compound 31 where Bn is benzyl. Compound 31 is reacted with hydrazine give compound 32, which is then reacted with sodium nitrite in an acid, such nitric acid, to give compound 33. Reaction of compound 33 with hydrogen and palladium on carbon in the presence of an acid, such as HCl, followed by reaction with 1,1'-thiocarbonyl diimidazole and a base such as triethylamine gives compound 34. Compounds of formula 1E are formed from compound 34 by first reacting compound 34 with methyl iodide in the presence of a base, such as sodium hydride, and then with ammonia.

Compounds of formula 1F are prepared as outlined in Reaction Scheme 6. Reaction of an ester with sulfinyl imine 11 and ClTi(O-iPr)$_3$ affords compound 35. Condensation of 35 with a diamine and trimethylaluminum (AlMe$_3$) affords compound 36. Hydrolysis of compound 36 with HCl gives compound 37. Reaction of compound 37 with cyanogen bromide gives compounds of formula 1F.

Reaction Scheme 6

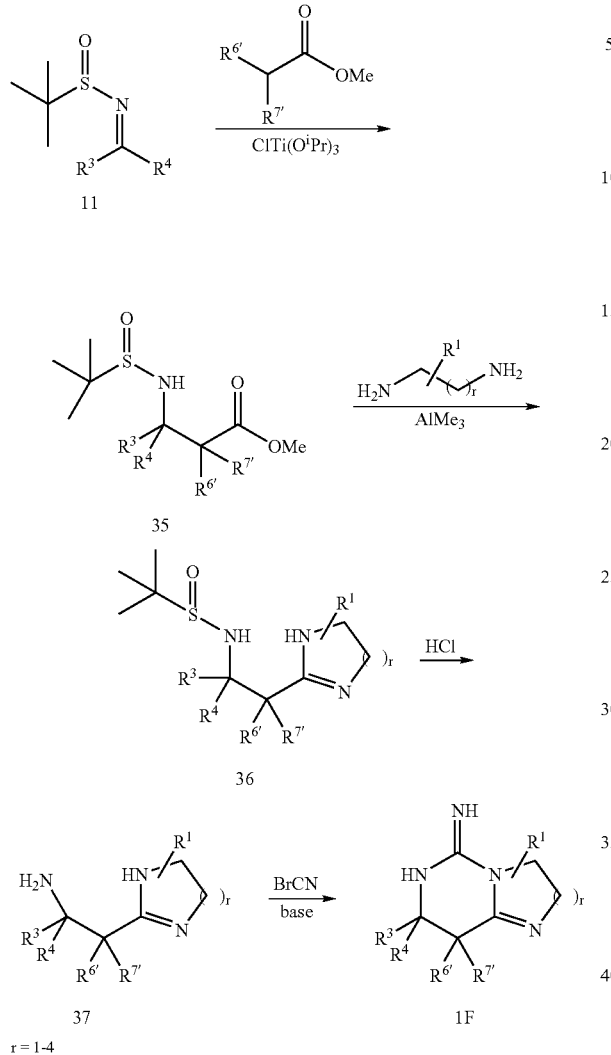

Compounds of formula 1G can be prepared as described in Reaction Scheme 7. Addition of 3-pyridylmagnesium bromide to the ketone 10 affords adduct 38. Reaction of 38 with thionyl chloride and displacement of the intermediate chloride by sodium azide affords the azido derivative 39. Compound 39 is oxidized by mCPBA (meta-chloroperbenzoic acid) to give N-oxide 40. Reaction of 40 with TMSCN (trimethylsilylcyanide) in the presence of dimethylcarbamyl chloride gives the cyanopyridine 41. Reduction of 41 with PPh₃ (triphenylphosphine) yields compounds of formula 1G.

Reaction Scheme 7

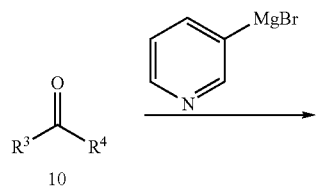

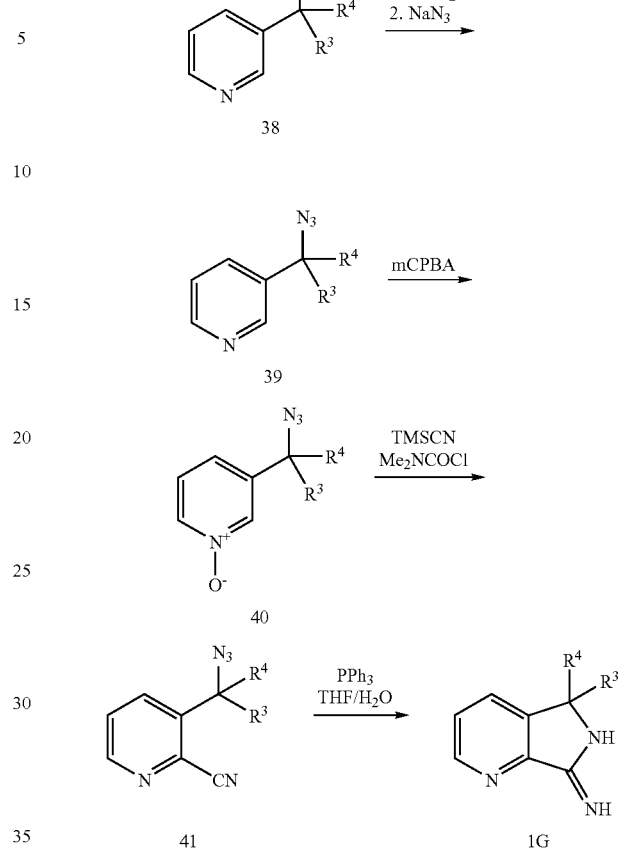

In Reaction Scheme 8, the sulfinyl imine 11 is reacted with an enolate derived from methyl acetate in the presence of ClTi(OiPr)₃ to afford the adduct 42. Hydrolysis of the methyl ester of 42 gives the acid 43, which is converted to keto ester 44 by reaction with isopropenyl chloroformate (IPCF) in the presence of 4-dimethylaminopyridine (DMAP) and Meldrum's acid, followed by heating. Condensation of 44 with hydrazine gives 45, which is hydrolyzed with HCl to afford an amine, which is treated with cyanogen bromide in the presence of a base to afford compounds of formula 1H.

Reaction Scheme 8

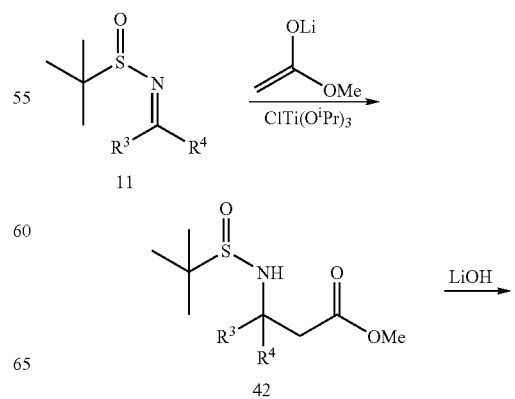

Reaction Scheme 9

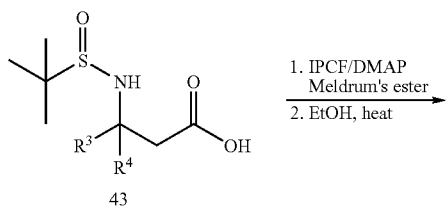

43

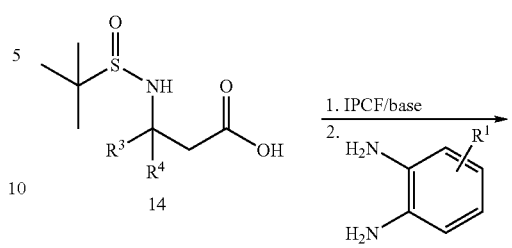

14

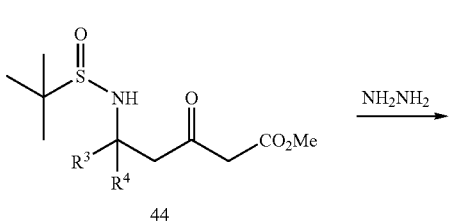

44

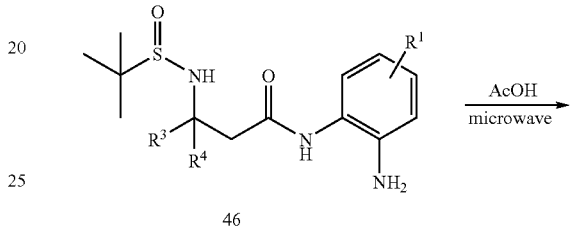

46

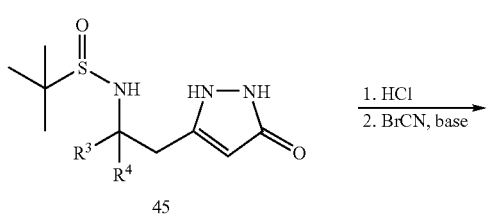

45

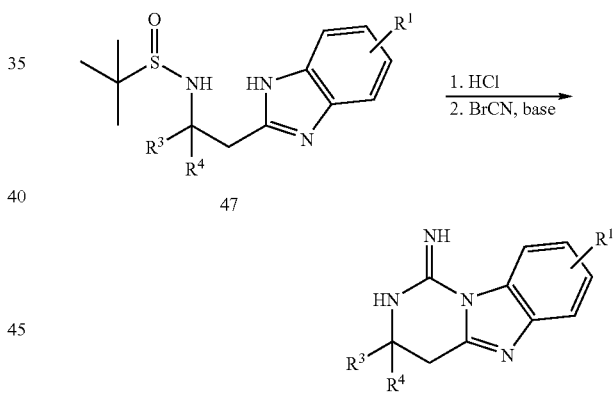

47

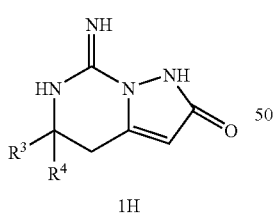

1H

The preparation of compounds of formula II is described in Reaction Scheme 9. Acid 14 is condensed with an o-phenylenediamine in the presence of IPCF and a base to give amide 46. Cyclodehydration of 46 by reaction with acetic acid (AcOH) under microwave conditions gives benzimidazole 47. The sulfinyl group of 47 is hydrolyzed by HCl and the resulting diamine derivative is condensed with BrCN to give compounds of formula II.

Compounds of formula 1J and 1F can be produced by the method outlined in Reaction Scheme 10. Reaction of sulfinyl imine 11 with an anion derived from a methyl substituted cyclic amidine 48 in the presence of trimethylaluminum (AlMe$_3$) affords the adduct 49. Treatment of 49 with TFA to remove the Boc protecting group is followed by cleavage of the sulfinyl group to give 50. Condensing 50 with BrCN affords compounds of formula 1J. Alternatively, hydrolysis of the sulfinyl group of 49 with HCl is followed by reaction with ethyl isothiocyanatoformate in the presence of a base to give thiourea derivative 51. Subjection of 51 to TFA to remove the Boc group followed by intramolecular guanidine formation mediated by EDC (1-[3-(dimethylamino)propyl]-3-ethylcarbodiimide hydrochloride) and triethylamine (Et$_3$N) gives 52. Cleavage of the carbamate of 52 by TMSBr (trimethylsilyl bromide) gives compounds of formula 1F.

Reaction Scheme 10

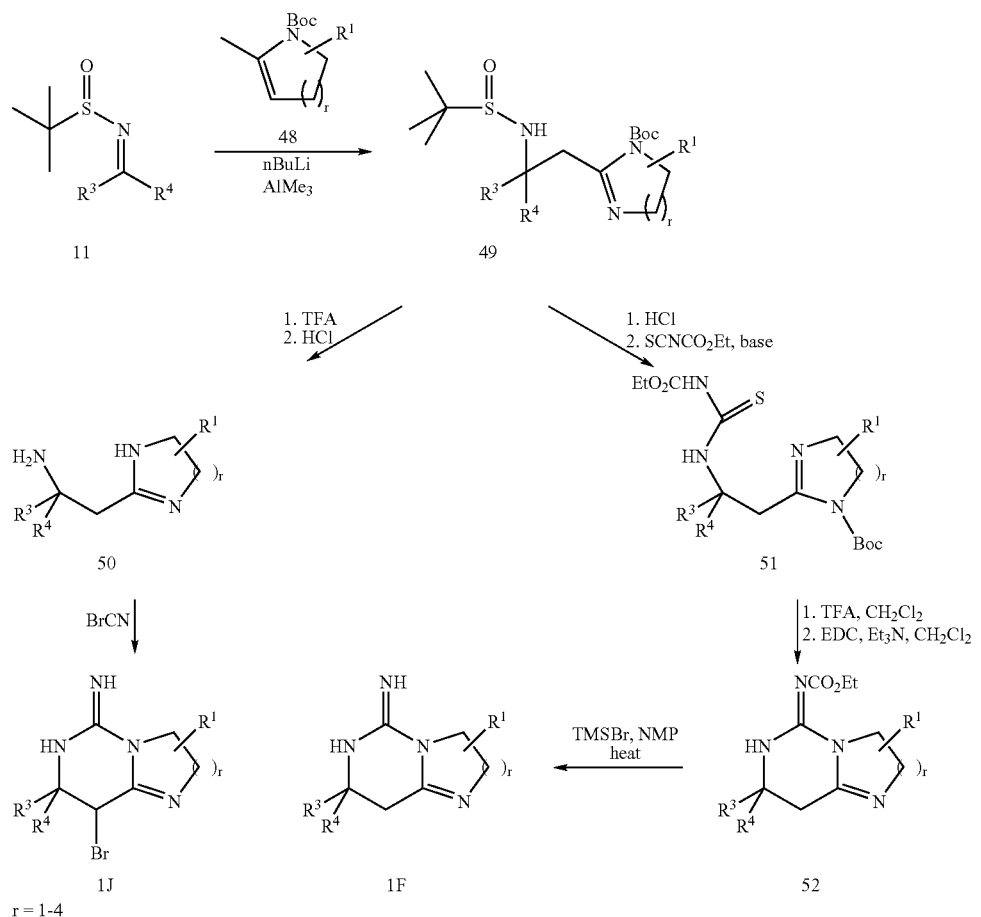

General Methods of Preparing Compounds of Formula II

The compounds of formula II can be prepared as outlined in Scheme 11. Addition of an appropriate precursor, for example an anion of lactone 53, to sulfinyl imine 11, affords the addition product 54. Treatment of 54 with HCl to cleave the sulfinyl group, followed by coupling with N-Boc-N'-methylthiourea with EDCI affords the cyclic imino product 55. The hydroxyl group of 55 can be converted to an azide 56 by treatment with azide under Mitsunobu conditions. Aza-Wittig reaction of 56 with $Bu_3P$ affords the bicyclic structure 57, which upon treatment with TFA affords compounds of formula II where $R^2$=H and $R^5$=Me.

Reaction Scheme 11

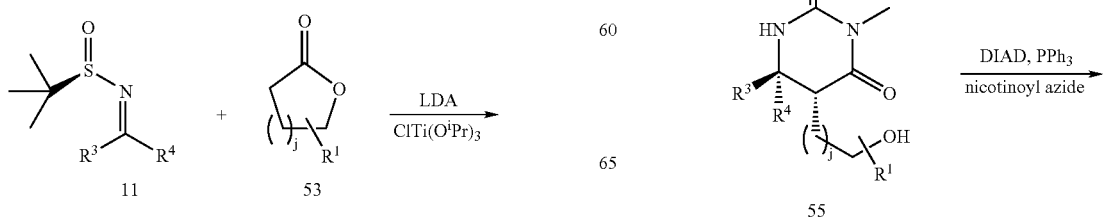

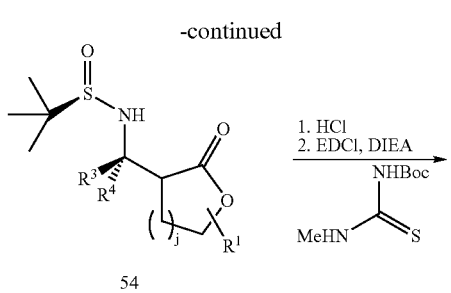

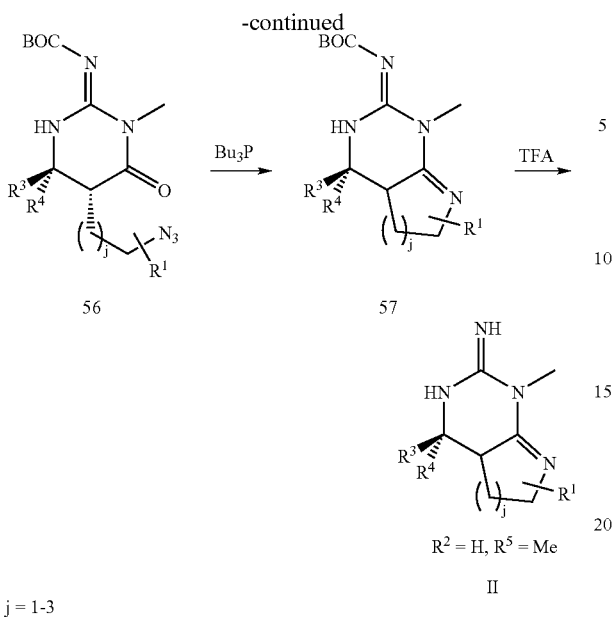

j = 1-3

The following Preparative Examples are intended to illustrate, but not limit, the scope of the invention.

PREPARATIVE EXAMPLES

Compound Example 1

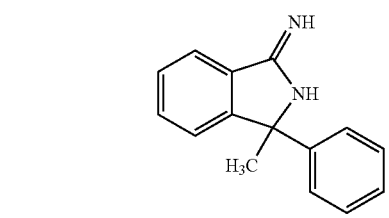

Step 1

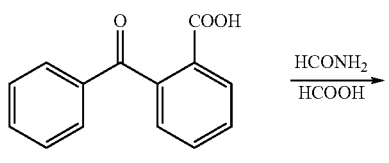

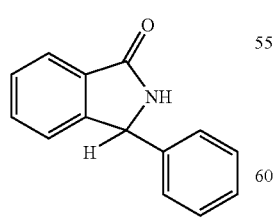

A mixture of 2-benzoylbenzoic acid A1 (11.3 g, 50 mmol) in formic acid (54 g, 1.2 mol) and formamide (29.7 g, 0.66 mol) was heated at refux for 22 h. The solid was collected by filtration, washed with ice-H$_2$O and dried in vacuo to give A2 (10.1 g, 97%). $^1$H-NMR (CDCl$_3$/CD$_3$OD): δ=7.77 (m, 1H), 7.39-7.48 (m, 2H), 7.19-7.30 (m, 6H), 5.78 (s, 1H). MS m/e 210 (M+H)$^+$.

Step 2

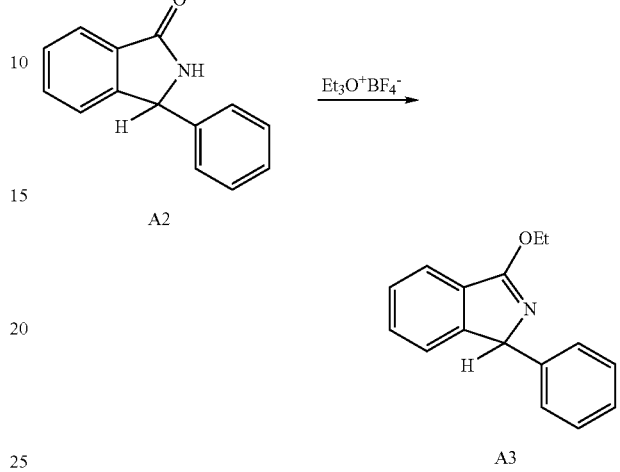

In analogy to the published procedure (M. Eberle and W. J. Houlihan, *Tetrahedron Lett.*, 1970, 36, 3167), a suspension of A2 (2.09 g, 10.0 mmol) in anhydrous CH$_2$Cl$_2$ (60 mL) was treated with 1 M triethyloxonium tetrafluoroborate in CH$_2$Cl$_2$ (12 mL, 12.0 mmol) at RT. The mixture was stirred at RT for 22 h. The reaction was quenched with saturated sodium carbonate (50 mL) and stirred vigorously for 0.5 h. The aqueous layer was extracted with CH$_2$Cl$_2$ (100 mL). The combined organic layers were washed with brine, dried (K$_2$CO$_3$) and concentrated. The residue was purified by column chromatography (silica gel, elution with CH$_2$Cl$_2$) to give the product A3 (900 mg, 38%). $^1$H-NMR (CDCl$_3$): δ=7.56 (m, 1H), 7.20-7.35 (m, 8H), 5.66 (s, 1H), 4.53 (m, 2H), 1.45 (m, 3H). MS m/e 238 (M+H)$^+$.

Step 3

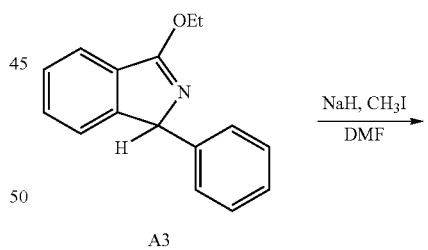

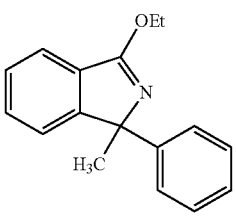

In analogy to the published procedure (M. K. Eberle et. al, J. Org. Chem., 1977, 42, 894), to a N$_2$ flushed flask was added NaH (60% in mineral oil, 44 mg, 1.1 mmol) and anhydrous DMF (3 mL). After the flask was purged with argon, a solution of A3 (237 mg, 1.0 mmol) in DMF (1.5 mL) was added.

The mixture was stirred at RT for 5 min. Then CH₃I (213 mg, 1.5 mmol) was added. The reaction mixture was stirred at RT for 16 h. The mixture was diluted with CH₂Cl₂ (100 mL), then quenched with saturated NH₄Cl. The organic layer was washed with H₂O and brine, then dried (MgSO₄) and concentrated. The residue was purified by column chromatography (silica gel, elution with hexane) to give the product A4 (220 mg, 88%). $^1$H-NMR (CDCl₃): δ=7.48 (m, 1H), 7.16-7.39 (m, 8H), 4.51 (m, 2H), 1.81 (s, 3H), 1.45 (m, 3H). MS m/e 252 (M+H)⁺.

Step 4

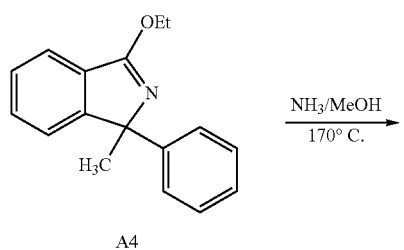

A4

A solution of A4 (70 mg, 0.28 mmol) in 7 N NH₃/MeOH (15 mL) was heated at 170° C. in a high pressure reactor for 6 h. The reaction mixture was cooled to RT and concentrated. Purification by PTLC (10% MeOH (2M NH₃)/CH₂Cl₂, developed 3 times) gave the product 1 (17 mg, 27%). $^1$H-NMR (CD₃OD): δ=7.68 (m, 1H), 7.31-7.39 (m, 5H), 7.13-7.22 (m, 3H), 1.77 (s, 3H). LCMS $t_R$=2.63 min m/e 223 (M+H)⁺.

Compound Example 2

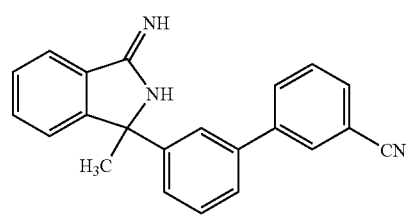

2

Step 1

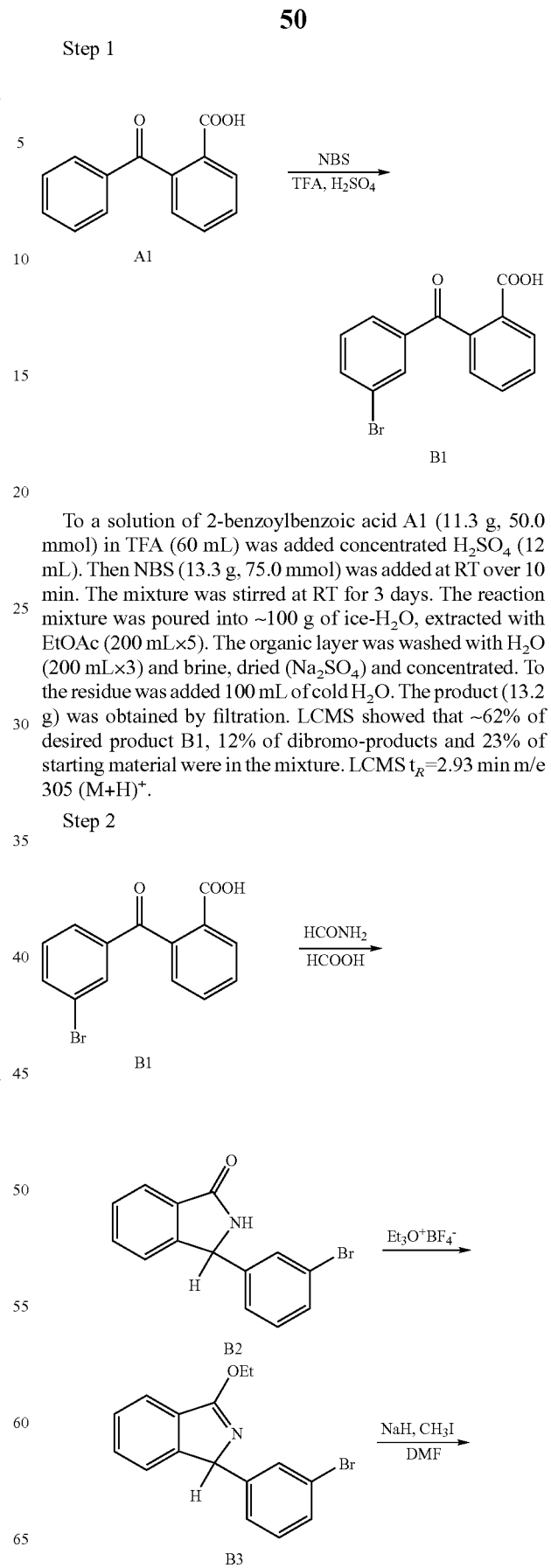

To a solution of 2-benzoylbenzoic acid A1 (11.3 g, 50.0 mmol) in TFA (60 mL) was added concentrated H₂SO₄ (12 mL). Then NBS (13.3 g, 75.0 mmol) was added at RT over 10 min. The mixture was stirred at RT for 3 days. The reaction mixture was poured into ~100 g of ice-H₂O, extracted with EtOAc (200 mL×5). The organic layer was washed with H₂O (200 mL×3) and brine, dried (Na₂SO₄) and concentrated. To the residue was added 100 mL of cold H₂O. The product (13.2 g) was obtained by filtration. LCMS showed that ~62% of desired product B1, 12% of dibromo-products and 23% of starting material were in the mixture. LCMS $t_R$=2.93 min m/e 305 (M+H)⁺.

Step 2

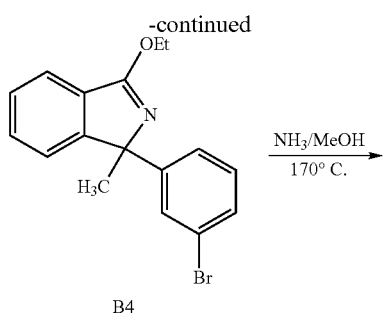

B4

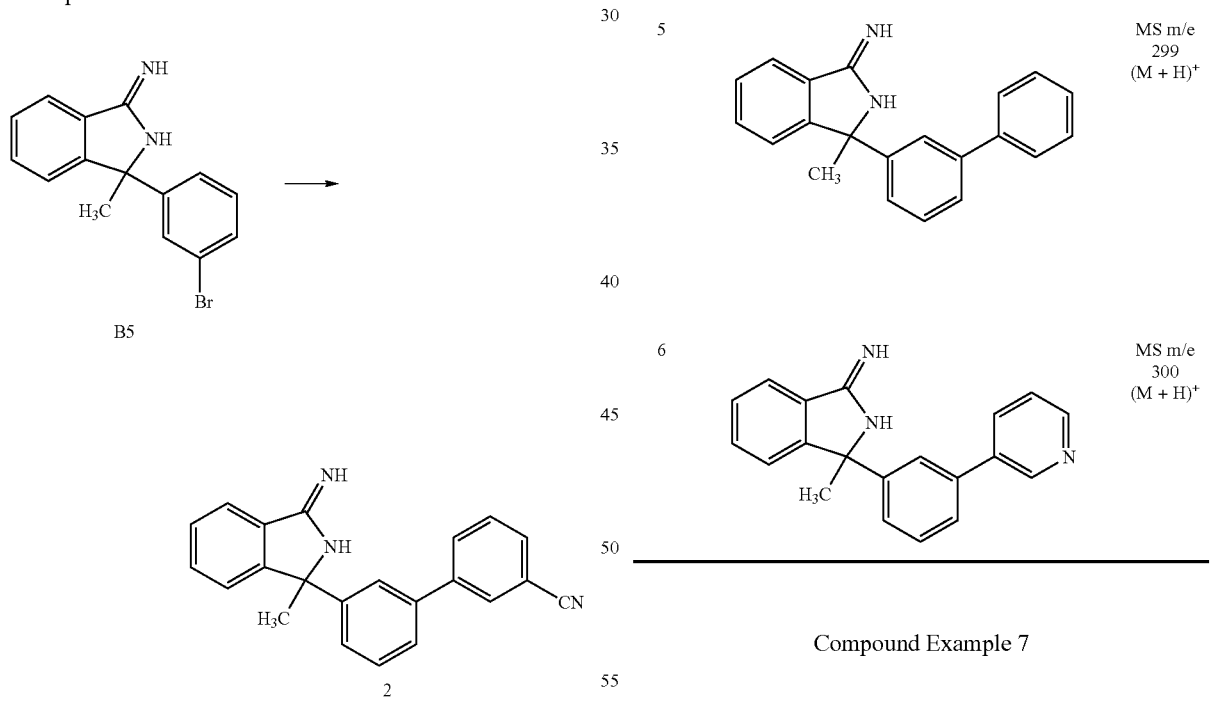

In analogy to the sequence of reactions described in Example 1, BI was converted to B5. ¹H-NMR (CD₃OD): δ=7.68 (m, 1H), 7.28-7.43 (m, 6H), 7.14 (t, 1H, J=8 Hz), 1.73 (s, 3H). LCMS $t_R$=2.95 min m/e 303 (M+H)⁺.

Step 6

B5

2

A mixture of B5 (30 mg, 0.10 mmol), 3-cyanophenylboronic acid (22 mg, 0.15 mmol), K₂CO₃ (28 mg, 0.20 mmol), and PS-Ph₃P—Pd (0.1 mmol/g, 50 mg, 0.005 mmol) in ethanol (1 mL) and H₂O (0.1 mL) was degassed with N₂ and then heated in a microwave reactor at 110° C. for 20 min. The mixture was filtered and concentrated. The residue was purified by PTLC (10% (2M NH₃MeOH)/CH₂Cl₂) to give 2 (23 mg, 71%). ¹H-NMR (CDCl₃): δ=7.70-7.75 (m, 2H), 7.41-7.56 (m, 10H), 1.86 (s, 3H). LCMS $t_R$=3.14 min m/e 324 (M+H)⁺.

By analogy to the procedures of Example 2, the following compounds were prepared:

TABLE 1

| Example | Structure | Masspectrum |
|---|---|---|
| 3 | <br>NH, NH, H₃C, Cl structure | MS m/e 333 (M + H)⁺ |
| 4 | <br>NH, NH, H₃C, OCH₃ structure | MS m/e 329 (M + H)⁺ |
| 5 | <br>NH, NH, CH₃, phenyl structure | MS m/e 299 (M + H)⁺ |
| 6 | <br>NH, NH, H₃C, pyridyl structure | MS m/e 300 (M + H)⁺ |

Compound Example 7

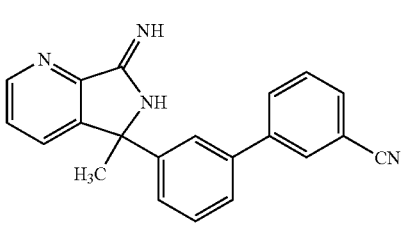

7

Step 1

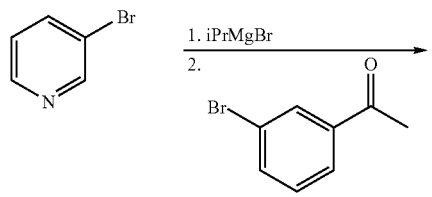

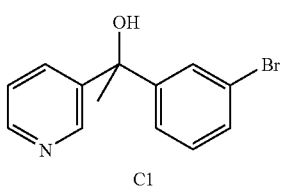

To a solution of 3-bromopyridine (7.9 g, 50 mmol) in THF (50 ml) was added 2M isopropylmagnesium chloride in THF (22.5 ml, 45 mmol). The mixture was stirred for 2 h and 3-bromoacetophenone (9.95 g, 50.0 mmol) was added. The resulting mixture was stirred for 4 h and quenched with saturated NH$_4$Cl. The mixture was extracted with EtOAc (2×200 ml) and the combined organic layers were washed with saturated NaHCO$_3$ and brine, dried over MgSO$_4$, and concentrated. The residue was purified by column chromatography (gradient 0-70% EtOAc/Hexanes) to give the product C1 (1.68 g, 13%). MS (M+H): 278, 280

Step 2

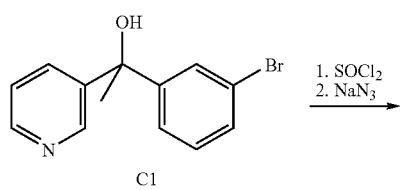

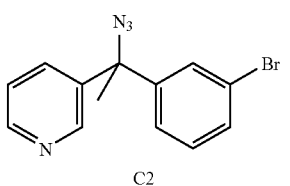

A mixture of the product of Step 1 C1 (1.26 g, 4.53 mmol) and thionyl chloride (0.595 g, 5.00 mmol) in anhydrous toluene (12 ml) was stirred at 80° C. for 45 minutes. The mixture was concentrated and the residue was dissolved in DMSO (10 ml). Sodium azide (0.878 g, 13.5 mmol) was added and the mixture was stirred at 50° C. for 1 h. The mixture was diluted with water (50 ml) and extracted with EtOAc (2×100 ml). The combined organic layers were washed with water and brine, dried over MgSO$_4$, and concentrated to give the crude product C2 (1.05 g). MS (M+H): 303, 305

Step 3

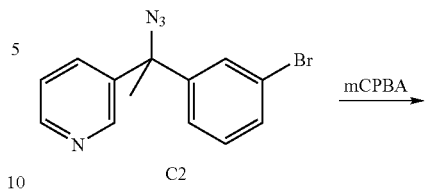

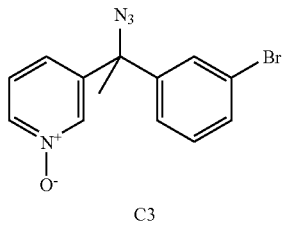

A mixture of the product C2 (190 mg, 0.629 mmol) and mCPBA (155 mg, 0.692 mmol) in CH$_2$Cl$_2$ (5 ml) was stirred for 80 minutes. The mixture was diluted with CH$_2$Cl$_2$ (50 ml) and extracted with saturated NaHCO$_3$ and brine. The organic layer was dried over MgSO$_4$, concentrated, and purified by column chromatography (gradient 0-2% MeOH/CH$_2$Cl$_2$) to give the product C3 (210 mg, 100%). MS (M+H): 319, 321.

Step 4

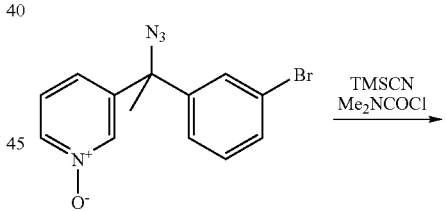

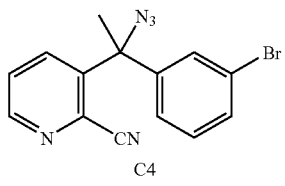

To a solution of the product of Step 3 C3 (210 mg, 0.629 mmol) in anhydrous CH$_3$CN (5 ml) was added TMSCN (103 mg, 1.04 mmol) and dimethylcarbamyl chloride (112 mg, 1.04 mmol). The solution was heated to 80° C. in a sealed tube for 3.5 h. After cooling to room temperature, the mixture was diluted with EtOAc (60 ml) and washed with water and brine. The organic layer was dried over MgSO$_4$, concentrated, and purified by column chromatography (gradient 0-15% EtOAC/Hexanes) to give the product C4 (40 mg, 19%). MS (M+H): 328, 330

55
Step 5

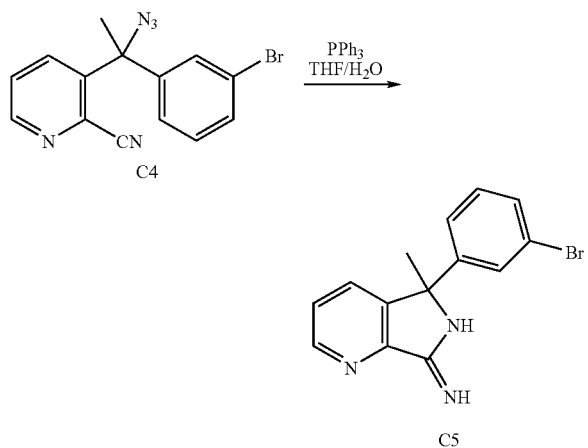

To a solution of the product of Step 4 C4 (40 mg, 0.12 mmol) in THF (2.5 ml) and water (75 µl) was added triphenylphosphine (54 mg, 0.21 mmol). The mixture was stirred for 5 h and 1M trimethylphosphine (0.4 ml) was added. The mixture was stirred for 16 h and concentrated. The residue was purified by preparative TLC (10% 2M $NH_3$/MeOH in $CH_2Cl_2$) to give the product C5 (27 mg, 74%). MS (M+H): 302, 304.

Step 6

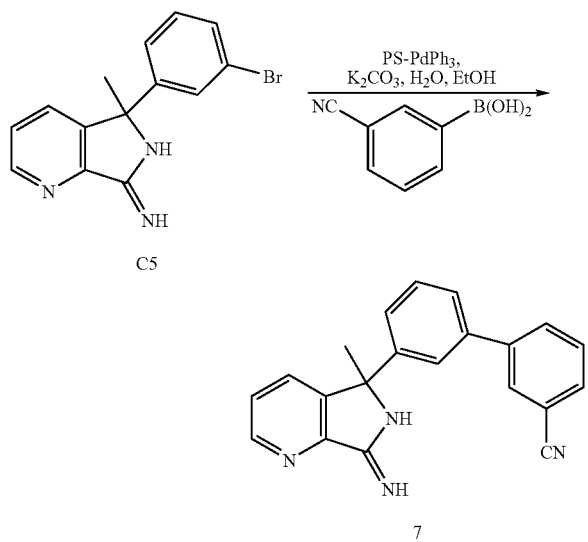

A mixture of the product of Step 5 C5 (13 mg, 0.043 mmol), 3-cyanophenylboronic acid (9.5 mg, 0.065 mmol), potassium carbonate (12 mg, 0.086 mmol), and PS —$PPh_3$-Pd (22 mg, 0.0022 mmol) in water (0.1 ml) and EtOH (1 ml) was heated to 110° C. in a microwave reactor for 30 minutes. The mixture was filtered, concentrated, and purified by preparative TLC (10% 2M $NH_3$/MeOH in $CH_2Cl_2$) to give the product 7 (10 mg, 72%). $^1$H-NMR ($CDCl_3$) δ 8.59 (m, 1H), 7.79 (m, 3H), 7.61 (m, 2H), 7.50 (m, 2H), 7.41 (m, 2H), 7.32 (m, 1H), 1.90 (s, 3H).

LCMS RT=2.64 min, M+H=325

56
Compound Example 8

Step 1

To a solution of (R)-(+)-2-methyl-2-propane sulfinamide (5.0 g, 41 mmol, 1 eq) and 1-(4-bromo-2-thienyl)ethan-1-one (9.3 g, 45 mmol, 1.1 eq) in anhydrous THF (70 mL) at room temperature was added $Ti(OEt)_4$ (17.3 mL, 82.6 mmol, 2 eq). The mixture was heated at 70° C. for 24 h. After cooling to room temperature, the mixture was poured into 70 mL of brine under vigorous stirring. The resulting suspension was filtered through a pad of Celite and the solid was washed with EtOAc (2×100 mL). The filtrate was washed with brine (100 mL), dried ($Na_2SO_4$), and concentrated in vacuo. The residue was chromatographed on silica gel by eluting with hexane/EtOAc (5:1) to give 10.1 g (80%) of D1 as a yellow solid. $^1$HNMR ($CDCl_3$, 300 MHz): δ 7.39 (m, 2H), 2.71 (s, 3H), 1.3 (s, 9H). MS (ESI): MH$^+$=309.7. HPLC $t_R$=7.1 min.

Step 2

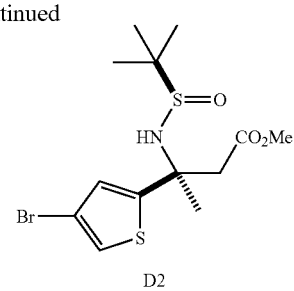

D2

To a solution of methyl acetate (5.15 mL, 64.8 mmol, 2 eq) in THF (5 mL), LDA (2M in heptane/THF, 34 mL, 68 mmol, 2.1 eq) was added dropwise via a syringe at −78° C. After stirring at −78° C. for 30 min, a solution of ClTi(Oi-Pr)$_3$ (32.5 mL, 136 mmol, 4.2 eq) in THF (90 mL) was added dropwise to form an orange-colored enolate solution. After stirring for another 30 min, a solution of D1 (10.0 g, 32.4 mmol, 1 eq) in THF (20 mL) was added dropwise via a syringe. The mixture was stirred at −78° C. for 3 h and TLC showed no starting material left. A saturated aqueous solution of NH$_4$Cl (10 eq) was added and the suspension was warmed up to room temperature. The mixture was diluted with H$_2$O (100 mL) and stirred for 10 min. The mixture was then partitioned between H$_2$O (100 mL) and EtOAc (150 mL). The organic layer was separated and the aqueous layer was extracted with EtOAc (3×150 mL). The combined organic layers were washed with brine, dried (MgSO$_4$) and concentrated to give a brown oil. Chromatography on silica gel using 50% EtOAc/hexanes as eluent gave 7.82 g (63%) of D2 as a yellow solid. $^1$HNMR (CDCl$_3$, 300 MHz): δ 7.14 (s, 1H), 6.79 (s, 1H), 5.8 (br s, 1H), 3.66 (s, 3H), 3.08 (m, 2H), 1.79 (m, 3H), 1.3 (s, 9H). MS (ESI): MH$^+$=383.7. HPLC t$_R$=7.05 min.

Step 3

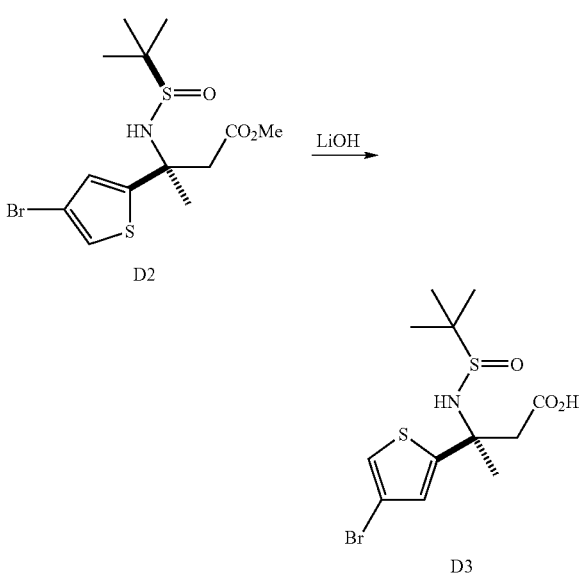

To a solution of D2 (2.6 g, 6.8 mmol) in 5 mL of MeOH/H$_2$O (3:2 v/v) was added LiOH (0.49 g, 20 mmol, 3 eq). The reaction mixture was stirred at room temperature for 16 h. The solvent was evaporated and the residue was dissolved in 15% MeOH/CH$_2$Cl$_2$ (20 mL) and filtered through a short silica column. The eluent was collected and concentrated to give 2.2 g (88%) of D3 as an off-white solid. $^1$HNMR (CDCl$_3$, 300 MHz): δ 7.05 (s, 1H), 6.80 (s, 1H), 2.81 (m, 2H), 1.66 (br. s, 3H), 1.20 (m, 9H). MS (ESI): MH$^+$=369.7. HPLC t$_R$=6.2 min.

Step 4

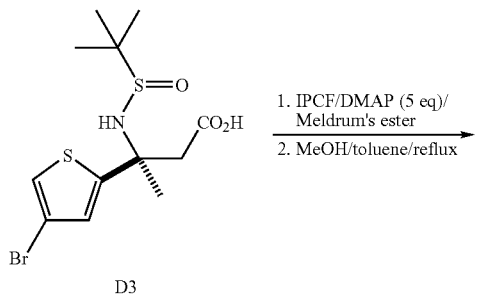

D3

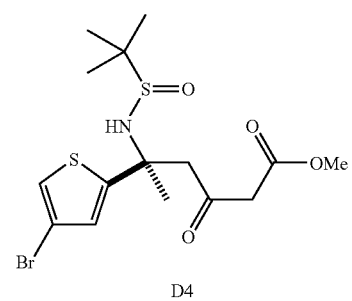

D4

To a solution of isoprenyl chloroformate (0.62 mL, 3.5 mmol) in anhydrous CH$_2$Cl$_2$ (3.0 mL) was added dropwise a solution of D3 (1.0 g, 2.7 mmol, 1 eq), DMAP (1.66 g, 15.6 mmol, 5 eq), and Meldrum's acid (0.47 g, 3.2 mmol, 1.2 eq) in CH$_2$Cl$_2$ (9 mL) at −5° C. After stirring at −5° C. for 2 h, the resulting mixture was washed with 5% KHSO$_4$, water, brine, dried (MgSO$_4$), and concentrated in vacuo to give 1.45 g of a yellow oil. The oil was dissolved in 20 mL of toluene and 5 mL of MeOH and the mixture was heated at reflux for 5 h. The solvent was evaporated and the residue was purified by column chromatography using 1:2 EtOAc/hexane as eluent to give 1.31 g (88%) of D4 as a yellow oil. $^1$HNMR (CDCl$_3$, 300 MHz) δ7.06 (s, 1H), 6.74 (s, 1H), 3.71 (s, 3H), 3.49-3.32 (m, 4H), 1.70 (s, 3H), 1.24 (s, 9H). MS (ESI): MH$^+$=425.7. HPLC t$_R$=6.9 min.

Step 5

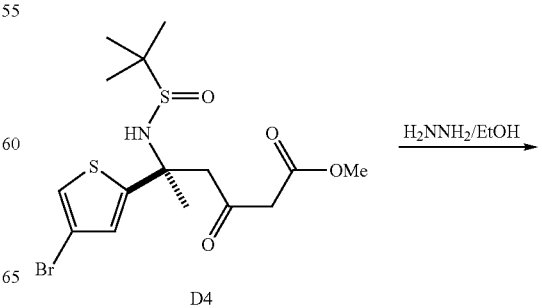

D4

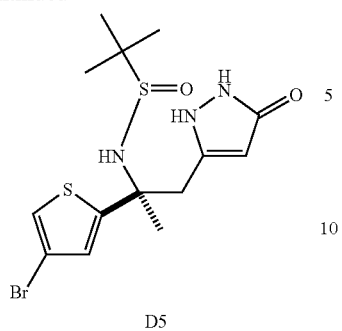

D5

To a solution of D4 (0.093 g, 0.22 mmol, 1 eq) in ethanol (0.5 mL) was added hydrazine (0.02 mL, 0.44 mmol, 2 eq). The reaction mixture was heated at 50° C. for 3 h. The solvent was evaporated to give 0.090 g (99%) of D5 as a yellow oil. ¹HNMR (CDCl₃, 300 MHz): δ 7.1 (s, 1H), 6.86 (s, 1H), 5.6 (br s, 1H), 5.20 (s, 1H), 4.24 (br s, 1H), 3.26-3.18 (m, 2H), 2.81 (br s, 1H), 1.76 (s, 3H), 1.29 (br s, 9H). MS (ESI): MH⁺=407.7. HPLC $t_R$=5.5 min.

Step 6

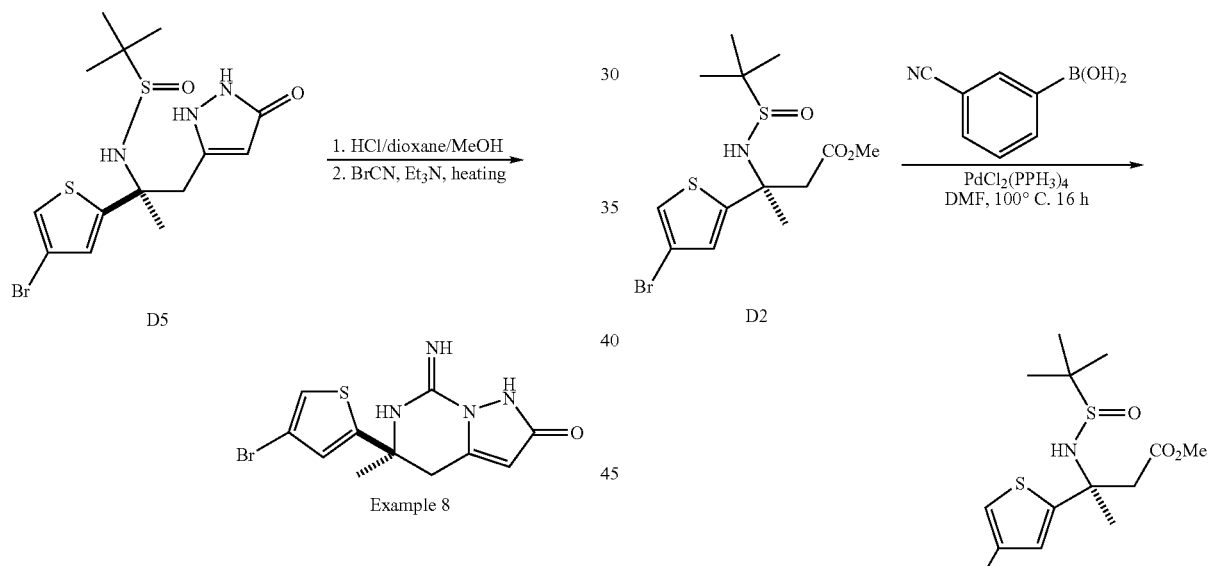

Example 8

To a solution of D5 (0.90 g, 0.22 mmol, 1 eq) in MeOH (2.5 mL) at 0° C. was added 4N HCl in dioxane (3.2 mL). The reaction mixture was stirred at room temperature for 30 min. The solvent was evaporated and the residue dissolved in 1.2 mL of MeOH. After stirring at room temperature for 15 min, the mixture was concentrated under reduced pressure to give 0.098 g (100%) of (S)-3-(2-amino-2-(4-bromothiophen-2-yl) propyl)-1,2-dihydropyrazol-5-one HCl salt as a yellow solid. ¹HNMR (CDCl₃, 300 MHz): δ 7.72 (s, 1H), 7.54 (s, 1H), 5.63 (s, 1H), 3.70-3.6 (m, 2H), 3.4 (br s, 2H), 2.05 (br s, 1H), 2.00 (br s, 1H), 1.76 (s, 3H). MS (ESI): MH⁺=303.8. HPLC $t_R$=1.5 min. A solution of (S)-3-(2-amino-2-(4-bromothiophen-2-yl) propyl)-1,2-dihydropyrazol-5-one HCL salt (0.044 g, 0.15 mmol) in EtOH (3 mL) was treated with BrCN (0.022 g, 0.20 mmol, 1.4 eq) at room temperature for 16 h. The solvent was evaporated and the residue was purified by reverse phase preparative HPLC to give 0.030 g (53%) of Example 8 as a white solid. ¹HNMR (CDCl₃, 300 MHz): δ 7.72 (s, 1H), 7.54 (s, 1H), 5.63 (s, 1H), 3.70-3.6 (m, 2H), 3.4 (br s, 2H), 2.05 (br s, 1H), 2.00 (br s, 1H), 1.76 (s, 3H) d. MS (ESI): MH⁺+1=329.8. HPLC $t_R$=1.2 min.

Compound Example 9

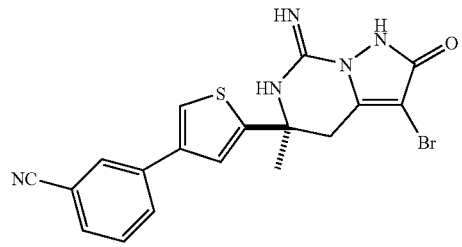

Example 9

Step 1

A mixture of D2 (500 mg, 1.3 mmol), 3-cyanophenylboronic acid (385 mg, 2.6 mmol), bis(triphenylphosphine)palladium(II) dichloride (92 mg, 0.13 mmol) and potassium carbonate (7.8 mmol, 1.1 g) in 25 mL of N,N-dimethylformamide was heated at 100° C. under argon for 16 h. After cooling to room temperature, the mixture was filtered and the filtrate evaporated. The residue was subjected to flash column chromatography (hexanes/EtOAc 1:3) to provide 307 mg (58%) of E1 as a brown solid. ¹HNMR (CDCl₃, 300 MHz): δ 7.78 (m, 2H), 7.52 (m, 2H), 7.41 (s, 1H), 7.18 (s, 1H), 5.82 (s, NH), 3.63 (s, 3H), 3.12 (s, 2H), 1.85 (s, 3H), 1.32 (s, 9H). MS (ESI): MH⁺=405.4. HPLC $t_R$=7.3 min Step 2

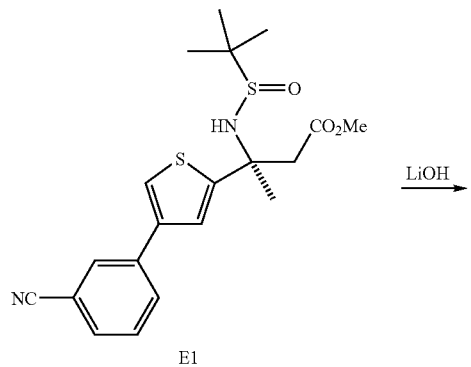

Following a similar procedure as described in Example 8, hydrolysis of E1 provided E2 as a white solid. ¹HNMR (CDCl₃, 300 MHz): δ 7.94 (br s, 1H), 7.87 (m, 1H), 7.57 (s, 1H), 7.54-7.37 (m, 2H), 7.33 (s, 1H), 2.81 (m, 2H), 1.83 (br. s, 3H), 1.21 (m, 9H). MS (ESI): MH⁺=390.7. HPLC $t_R$=6.6 min.

Step 3

Following a similar procedure as described in Example 8, E3 (0.61 g, 55% yield) was obtained from E2 as a yellow oil. ¹HNMR (CDCl₃, 300 MHz): δ 7.81 (br s, 1H), 7.72 (m, 1H), 7.54-7.37 (m, 2H), 7.33 (s, 1H), 7.18 (s, 1H), 5.49 (s, 1H), 4.18 (m, 2H), 3.63-3.32 (m, 4H), 1.77 (br. s, 3H), 1.25-1.20 (m, 12H). MS (ESI): MH⁺=460.7. HPLC $t_R$=7.2 min.

Step 4

A mixture of E3 (0.14 g, 0.30 mmol) and hydrazine (0.014 mL, 0.45 mmol, 1.5 eq) in EtOH (1 mL) was heated at 50° C. for 2 h. The solvent was evaporated to give 0.12 g (90%) of E4 as a yellow oil. ¹HNMR (CDCl₃, 300 MHz): δ 7.80 (m, 2H), 7.67 (m, 2H), 7.27 (s, 1H), 7.18 (s, 1H), 5.22 (s, 1H), 4.25 (br s, 1H), 4.17 (br s, 1H), 3.46 (s, 3H), 3.32-3.28 (m, 2H), 1.79 (s, 3H), 1.29 (br s, 9H). MS (ESI): MH⁺=429.4.

Step 5

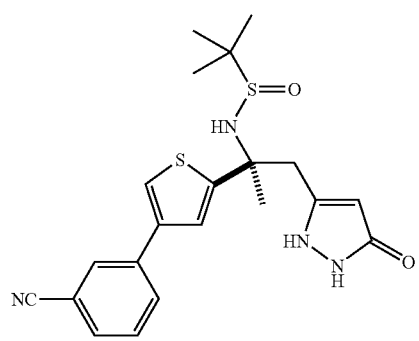

E4

1. HCl/dioxane/MeOH
2. BrCN, Et₃N, heating

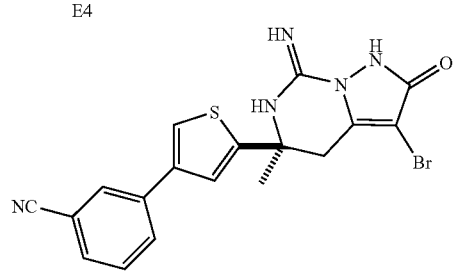

Example 9

To a solution of E4 (0.018 g, 0.56 mmol, 1 eq) in MeOH (2.0 mL) at 0° C. was added 4N HCl in dioxane (1.0 mL). The mixture was stirred at room temperature for 1 h. The solvent was evaporated and the residue dissolved in 1.2 mL of MeOH. After stirring for 15 min, the mixture was concentrated under reduced pressure to give 0.020 g (100%) of (3-(5-((S)-2-amino-1-(5-oxo-2,5-dihydro-1H-pyrazol-3-yl) propan-2-yl) thiophen-3-yl)benzonitrile HCl salt as a yellow solid. The (S)-3-(2-amino-2-(4-bromothiophen-2-yl)propyl)-1,2-dihydropyrazol-5-one HCl salt (0.018 g, 0.056 mmol) was dissolved in EtOH (2 mL) was treated with BrCN (0.009 g, 0.08 mmol) at room temperature for 16 h. The solvent was evaporated and the residue was purified by reverse phase preparative HPLC to give 0.003 g (53%) of Example 9 as a white solid. ¹HNMR (CDCl₃, 300 MHz): 612.09 (br s, 1H), 7.74 (m, 1H), 7.61-7.44 (m, 2H), 7.40 (s, 1H), 7.3 (s, 1H), 3.51-3.46 (m, 1H), 3.42 (s, 3H), 3.22 (m, 1H), 2.05 (m, 2H), 1.76 (s, 3H). MS (ESI): MH⁺=429.9. HPLC t$_R$=5.5 min.

Compound Example 10

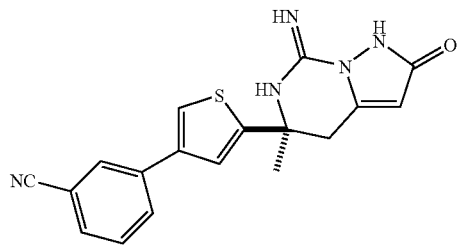

Example 10

Step 1

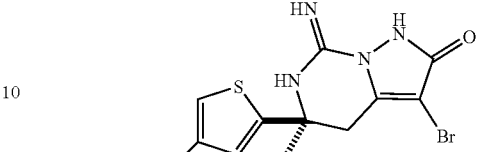

Example 9

Pd(C)/H₂
EtOH

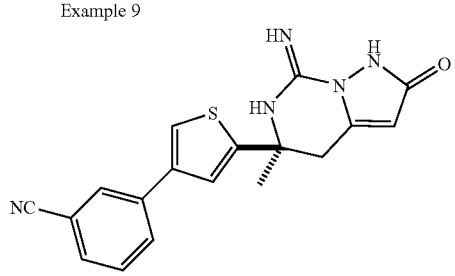

Example 10

A mixture of Example 9 (0.020 g, 0.047 mmol) and Pd(C) (25 mg) in EtOH (5 mL) was hydrogenate at room temperature under a hydrogen balloon for 16 h. The reaction mixture was filtered through Celite and the filtrate was concentrated in vacuo. The residue was purified by reverse phase preparative HPLC to give 0.0030 g (18%) Example 10 as a white solid. ¹HNMR (CDCl₃, 300 MHz): 67.98 (m, 1H), 7.93-7.90 (m, 1H), 7.72 (s, 1H), 7.64-7.53 (m, 2H), 7.50 (s, 1H), 5.97 (s, 1H), 3.8-3.34 (m, 1H), 3.33 (s, 3H), 3.24-3.22 (m, 1H), 1.90 (s, 3H). MS (ESI): MH⁺=350.0. HPLC t$_R$=5.2 min.

Compound Example 11

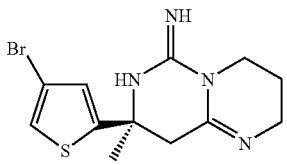 [SMILES: C[C@@]1(c2cc(Br)cs2)CC2=NCCCN2C(=N)N1]

Example 11

Compound Example 12

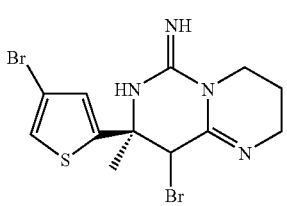 [SMILES: C[C@]1(c2cc(Br)cs2)NC(=N)N2CCCN=C2C1Br]

Example 12

Step 1

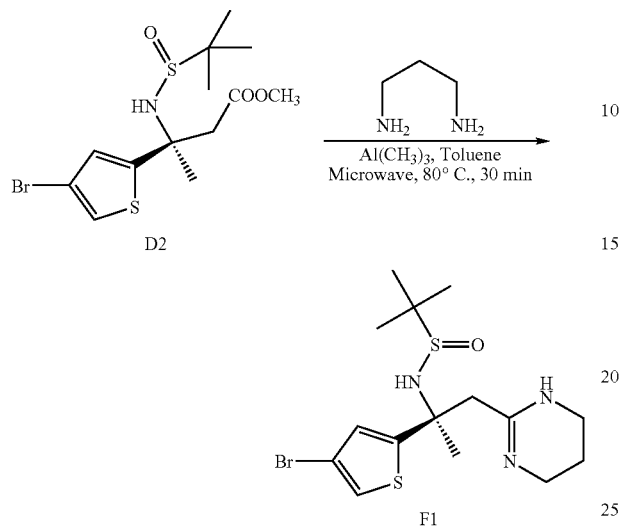

To a solution of 1,3-diaminopropane (116 mg, 1.6 mmol, 2 eq) in 5 mL of toluene at −5° C. bath was added dropwise Al(CH$_3$)$_3$ (2M in toluene, 0.75 mL, 1.5 mmol, 1.9 eq). The mixture was stirred at −5° C. for 5 min followed by the slow addition of a solution of D2 (300 mg, 0.79 mmol, 1 eq) in 2 mL of toluene. The cold bath was removed and the mixture was first stirred at RT for 5 min followed by heating in a microwave reactor at 90° C. for 10 min. The mixture was cooled to RT, quenched with water (5 mL), and diluted with EtOAc (20 mL). The solid was filtered off and the filtrate was washed with brine (10 mL×2), dried (Na$_2$SO$_4$), and concentrated to give F1 as a yellowish gum. MS (ESI): MH$^+$=406.3. HPLC t$_R$=5.2 min. $^1$HNMR (CDCl$_3$, 300 MHz): δ 7.65 (s, NH), 7.09 (s, 1H), 6.89 (s, 1H), 6.67 (s, NH), 2.65-2.90 (m, 4H), 1.79 (s, 3H), 1.59 (m, 2H), 1.30 (m, 11H).

Step 2

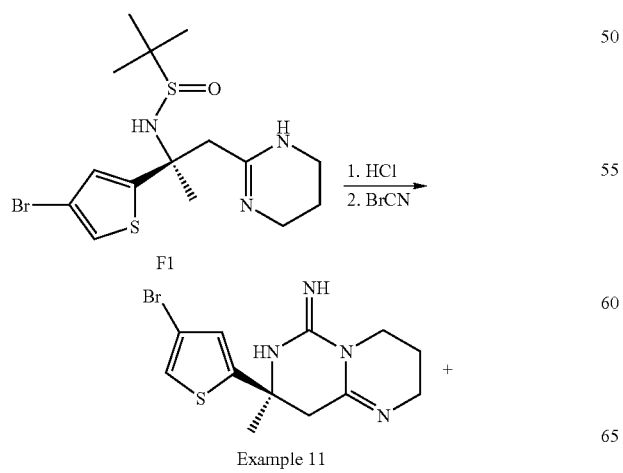

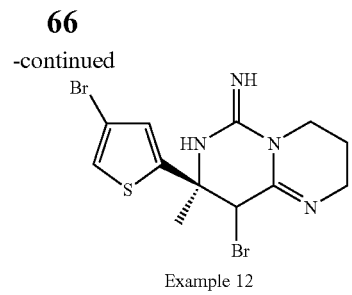

Example 12

To a solution of crude F1 (~79 mmol) in 10 mL of MeOH was added 1 mL of 4M HCl/dioxane. After stirring at RT for 3 h, the reaction mixture was concentrated and the crude product was purified on reverse phase preparative HPLC. The purified product was dissolved in 3 mL of sat. Na$_2$CO$_3$ and extracted with EtOAc (30 mL×3). The combined organic phase was dried (Na$_2$SO$_4$) and concentrated to give 182 mg (76%) of (S)-2-(4-bromothiophen-2-yl)-1-(1,4,5,6-tetrahydropyrimidin-2-yl)propan-2-amine as a white solid. MS (ESI): MH$^+$=302.2. HPLC t$_R$=1.1 min.

To a solution of (S)-2-(4-bromothiophen-2-yl)-1-(1,4,5,6-tetrahydropyrimidin-2-yl)propan-2-amine (35 mg, 0.12 mmol) in 4 mL of EtOH/CH$_2$Cl$_2$ (3:1, v/v) under argon was added BrCN (18 mg, 0.17 mmol, 1.4 eq). After stirring at RT for 16 h, the mixture was concentrated and the crude product was purified on reverse phase preparative HPLC to give 1.5 mg (4%) of Example 11 as a white solid. MS (ESI): MH$^+$=327.1. HPLC t$_R$=4.4 min. In addition, 15 mg of Example 12 was obtained as a white solid. MS (ESI): MH$^+$=407.2. HPLC t$_R$=4.8 min. $^1$HNMR (CDCl$_3$, 300 MHz): δ 7.22 (s, 1H), 6.96 (s, 1H), 5.58 (s, 1H), 3.83 (m, 2H), 3.57 (m, 2H), 2.08 (m, 2H), 1.92 (s, 3H).

Compound Example 13

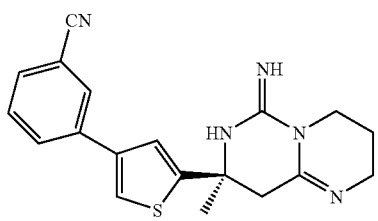 [SMILES: C[C@@]1(c2cc(-c3cccc(C#N)c3)cs2)CC2=NCCCN2C(=N)N1]

Example 13

Compound Example 14

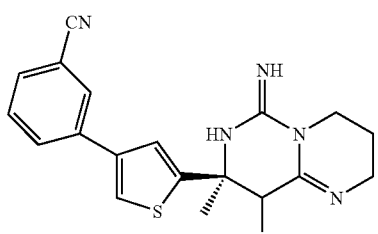

Example 14

Step 1

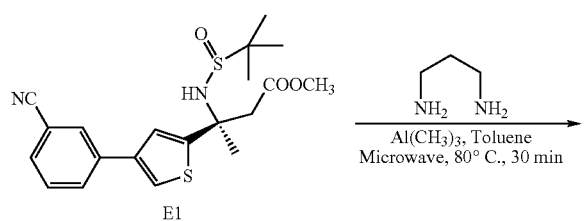

To a solution of 1,3-diaminopropane (37 mg, 0.50 mmol) in 4 mL of dry toluene under argon at −5° C. was slowly added trimethylaluminum (2M in toluene, 0.25 mL, 0.50 mmol) in 5 min. The mixture was stirred at −5° C. for 5 min and a solution of E1 in 2 mL of toluene was slowly added in 5 min. The bath was removed and the mixture was stirred for 5 min and then heated under microwave at 80° C. for 30 min. The reaction mixture was cooled to room temperature and quenched by 1 mL of water. 50 mL of ethyl acetate was added and the mixture was filtered. The filtrate was washed twice with brine and dried ($Na_2SO_4$). The solvent was removed and the residue was redissolved in dichloromethane and passed through a short silica plug using 15% methanol in dichloromethane to yield 90.5 mg (42%) G1 as a yellow solid. MS (ESI): $MH^+$=429.5. HPLC $t_R$=5.1 min.

Step 2

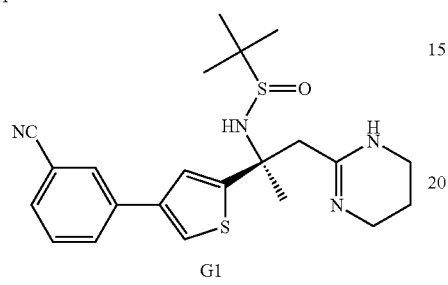

To a solution of G1 (90 mg, 0.21 mmol) in 5 mL of methanol was added 1 mL of 2M HCl in dioxane. The mixture was stirred at room temperature for 3 h and the solvent was evaporated under reduced pressure. The residue was suspended in 5 mL of saturated sodium carbonate and extracted with ethyl acetate (10 mL×3). The organic phases were combined and dried ($Na_2SO_4$). The solvent was removed and 66 mg (97%) of G2 was obtained as a sticky solid. MS (ESI): $MH^+$=325.0, HPLC $t_R$=4.1 min.

Step 3

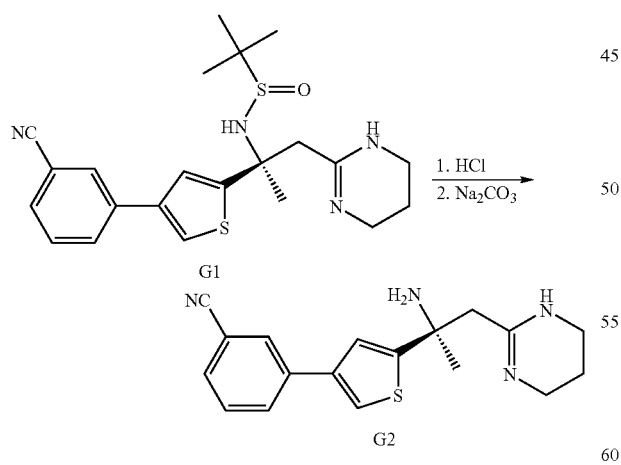

To a solution of G2 (60 mg, 0.18 mmol) in 2 mL of dry dichloromethane was added cyanogen bromide (23.5 mg, 0.22 mmol). The mixture was stirred at room temperature overnight and the solvent was evaporated. The residue was purified using preparative HPLC to produce 10.5 mg (17%) of Example 13 as a white solid. MS (ESI): $MH^+$=350.1, HPLC $t_R$=5.1 min. The HPLC purification also produced 11 mg (14%) of Example 14 as a white solid. MS (ESI): $MH^+$=428.0, HPLC $t_R$=5.3 min.

Compound Example 15

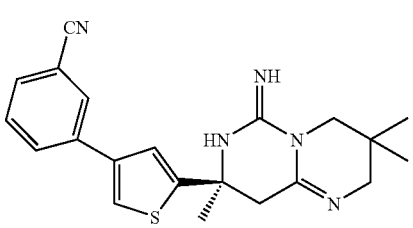 [SMILES: CC1(C)CN=C2C[C@@](C)(c3cc(-c4cccc(C#N)c4)cs3)NC(=N)N2C1]

Example 15

Example 15 was prepared following a similar procedure as described for Example 13. MS (ESI): MH⁺=378.1. HPLC $t_R$=4.8 min.

Compound Example 16

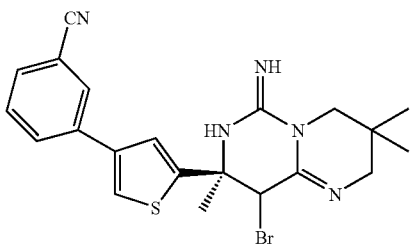 [SMILES: CC1(C)CN=C2C(Br)[C@@](C)(c3cc(-c4cccc(C#N)c4)cs3)NC(=N)N2C1]

Example 16

Example 16 was prepared following a procedure similar to that described for Example 14. MS (ESI): MH⁺=456.0. HPLC $t_R$=5.6 min. ¹HNMR (CDCl₃, 300 MHz): δ 7.5-8.0 (m, 6H), 5.48 (s, 1H), 3.2-3.5 (m, 4H), 1.9 (s, 3H), 0.97 (s, 3H), 0.46 (s, 3H).

Compound Example 17

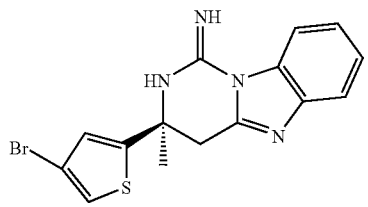 [SMILES: C[C@@]1(c2cc(Br)cs2)Cc2nc3ccccc3n2C(=N)N1]

Example 17

Step 1

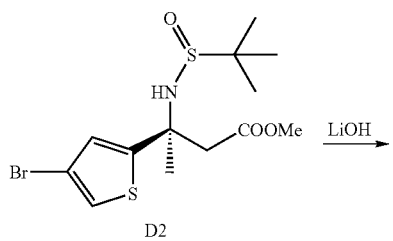

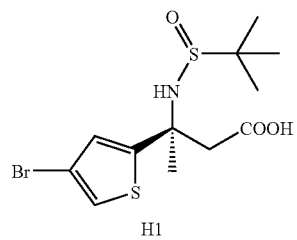

To a solution of D2 (400 mg, 1.0 mmol) in 10 mL of MeOH was added a solution of LiOH (100 mg, 4.1 mmol, 4.1 eq) in 3 mL of water. After stirring at RT for 16 h, the mixture concentrated. The residue was purified through short silica gel column (15% MeOH/CH₂Cl₂) to give 400 mg (100%) of H1 as a white solid.

Step 2

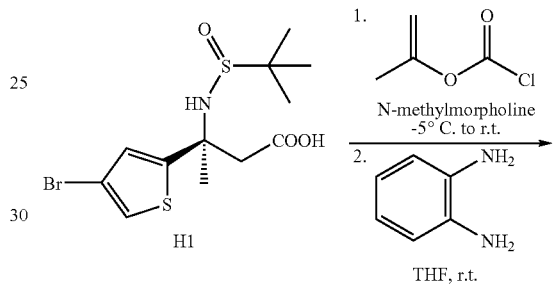

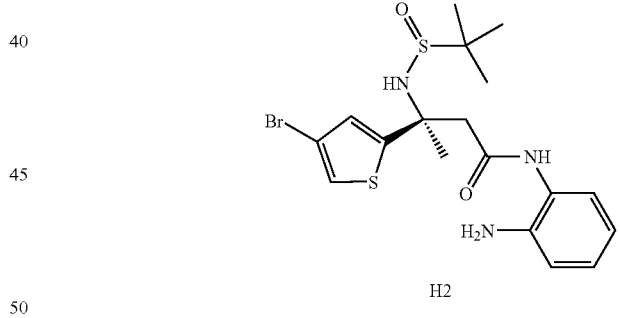

To a solution of H1 (200 mg, 0.52 mmol) in 10 mL of THF at −5° C. was added N-methylmorpholine (58 mg, 0.57 mmol, 1.1 eq) followed by the slow addition of a solution of isopropenyl chloroformate (70 mg, 0.58 mmol, 1.1 eq) in 2 mL of THF over min. Finally, a solution of 1,2-diaminobenzene (114 mg, 1.1 mmol, 2 eq) in 1 mL of THF was added. The mixture was stirred at −5 to 0° C. for 1 h and then at RT for 16 h. The mixture was concentrated and the residue was redissolved in EtOAc (20 mL), washed with NaHCO₃ and saturated brine, dried (Na₂SO₄), and concentrated. Silica gel column chromatography (5% MeOH/EtOAc) gave 106 mg (44%) of H2 as a yellow sticky solid. ¹HNMR (CDCl₃, 300 MHz): δ 8.23 (s, 1H), 7.20-6.65 (m, 6H), 5.86 (s, 1H), 3.08 (m, 2H), 1.81 (s, 3H), 1.27 (s, 9H). MS (ESI): MH⁺=458.4. HPLC $t_R$=6.1 min.

Step 3

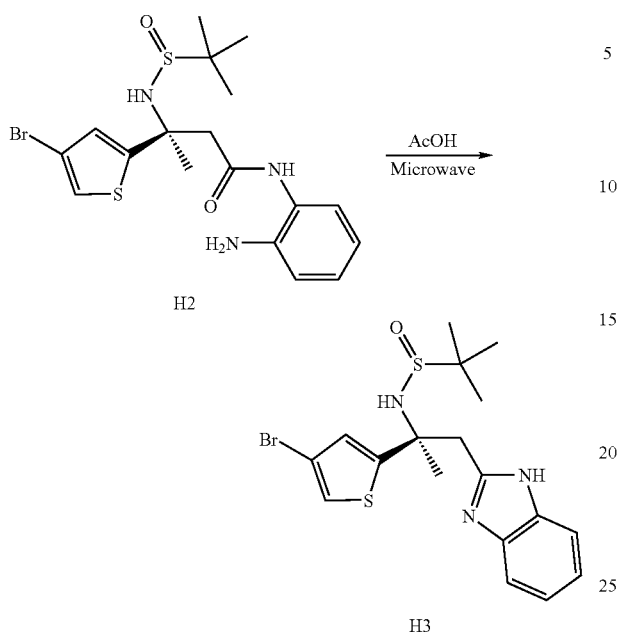

A solution of H2 (98 mg, 0.21 mmol) in 4 mL of AcOH was heated in a microwave reactor at 100° C. for 10 min. The mixture was concentrated to give 90 mg (100%) H3 as a yellow sticky solid. MS (ESI): MH$^+$=440.2. HPLC t$_R$=6.3 min

Step 4

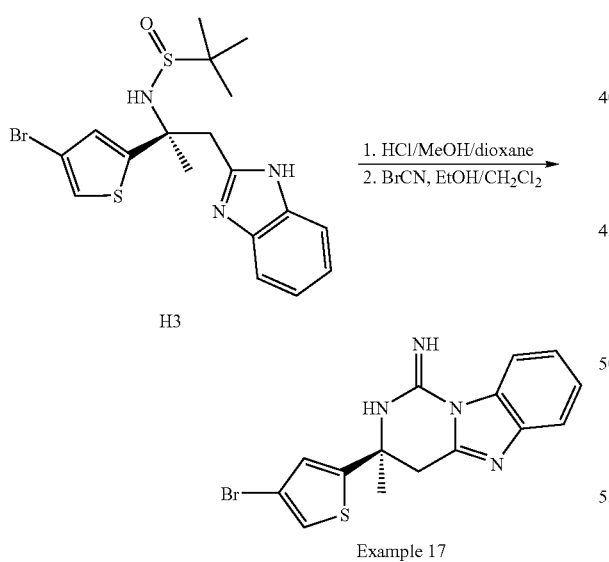

The crude H3 (~0.21 mmol) was treated with HCl/dioxane (4N, 2 mL) in 10 mL of MeOH at RT for 3 h. After evaporation of the solvent, the residue was partitioned between EtOAc (50 mL) and 10% NaHCO$_3$ (10 mL). The organic layer was separated and aqueous layer was extracted again with EtOAc (50 mL). The combined organic phase was washed with saturated brine, dried (Na$_2$SO$_4$), and concentrated to give 80 mg (100%) of (S)-1-(1H-benzo[d]imidazol-2-yl)-2-(4-bromothiophen-2-yl)propan-2-amine as a light brown solid. MS (ESI): MH$^+$=336.1 HPLC t$_R$=4.1 min.

To a solution of (S)-1-(1H-benzo[d]imidazol-2-yl)-2-(4-bromothiophen-2-yl)propan-2-amine (80 mg, 0.21 mmol) in 8 mL of EtOH/CH$_2$Cl$_2$ (3:1 v/v) was added BrCN (38 mg, 0.36 mmol, 1.5 eq). After stirring at RT for 16 h, the mixture was concentrated and the residue was purified on reverse phase preparative HPLC to give 31 mg (41%) of Example 17 as a white solid. $^1$HNMR (CDCl$_3$, 300 MHz): δ 7.78 (m, 2H), 7.48 (m, 2H), 7.07 (s, 1H), 6.90 (s, 1H), 3.87 (d, J=17 Hz, 1H), 3.56 (d, J=17 Hz, 1H), 2.00 (s, 3H). MS (ESI): MH$^+$=361.3. HPLC t$_R$=4.7 min.

Compound Example 18

Example 18

Step 1

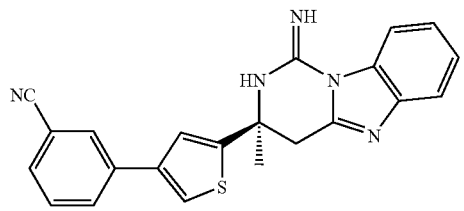

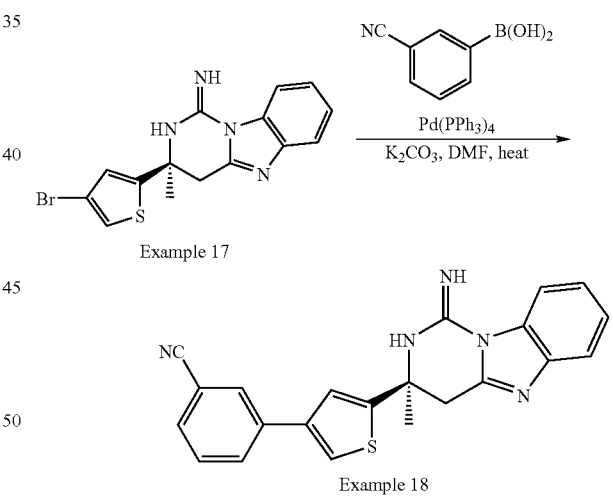

A mixture of Example 17 (14 mg, 0.039 mmol), 3-cyanophenylboronic acid (17 mg, 0.12 mmol, 3 eq), tetrakis(triphenylphosphine)palladium (5 mg, 0.004 mmol, 0.1 eq), and potassium carbonate (1M in H$_2$O, 0.5 mL, 0.5 mmol, 13 eq) in 1 mL of DMF was heated at 100° C. in a microwave reactor for 15 min. The mixture was concentrated and the residue was purified on reverse phase preparative HPLC to give 13 mg (87%) of Example 18 as a white solid. $^1$HNMR (CDCl$_3$, 300 MHz): δ 7.85-7.30 (m, 10H), 4.15 (d, J=17 Hz, 1H), 3.64 (d, J=17 Hz, 1H), 2.07 (s, 3H). MS (ESI): MH⁺=384.1. HPLC t_R=5.4 min.

Compound Example 19

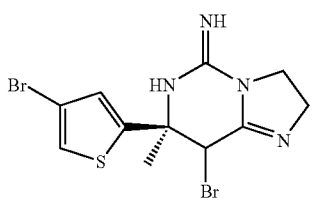 [SMILES: C[C@]1(c2cc(Br)cs2)NC(=N)N2CCN=C2C1Br]

Example 19

Step 1

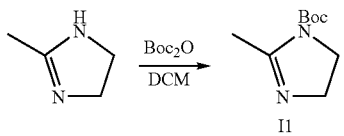

To a solution of 2-methyl-2-imidazole (5 g, 59 mmol, 1.0 eq) in 60 mL of dichloromethane at 0° C. was added (Boc) 20 (13.6 g, 1.05 eq) portionwise over 5 min. The mixture was stirred at RT for 4 h, and TLC showed no starting material left. The content was then washed with water and brine, dried over Na₂SO₄, and concentrated to give 9.5 g (87%) of I1 slightly as a yellow solid. ¹HNMR (CDCl₃, 300 MHz): δ 3.75 (m, 4H), 2.30 (s, 3H), 1.50 (s, 9H).

Step 2

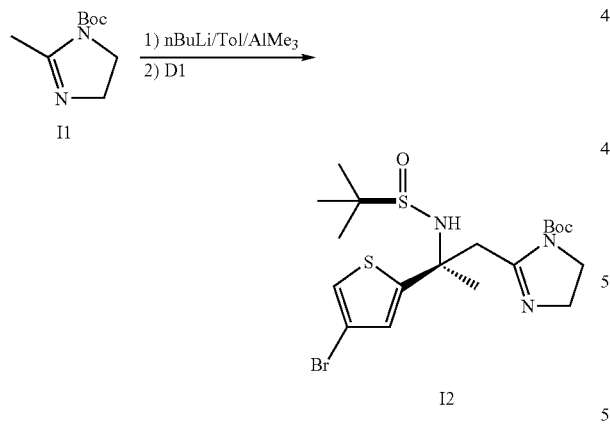

To a solution of I1 (2.54 g, 13.8 mmol, 2.0 eq) in 23 mL of toluene at −78° C. was added dropwise nBuLi (1.6M, 9.5 ml, 2.2 eq) and the mixture was stirred at −78° C. for 10 min (solution A). Meanwhile, to a solution of D1 (2.13 g, 6.9 mmol, 1.0 eq) in 8 mL of toluene at −78° C. was slowly added trimethylaluminum (2M in toluene, 4.0 mL, 8.0 mmol, 1.2 eq) and the mixture was stirred for 5 min at −78° C. (solution B). Solution B was slowly cannulated to solution A over 20 min. The resulting mixture was stirred at −78° C. for 3 h, followed by slow warm-up to 0° C. Saturated aq. Na₂SO₄ solution was added dropwise until gas was no longer evolved upon addition. Dry MgSO₄ powder was then added and the mixture was stirred for 10 min before it was filtered and rinsed with EtOAc. The filtrate was concentrated and the residue was purified on silica gel chromatography (1:1 EtOAc/hexane) to give 2.1 g (62%) of 12 as a brown oil. ¹HNMR (CDCl₃, 300 MHz): δ 7.05 (s, 1H), 6.80 (s, 1H), 3.60 (m, 4H), 3.55 (d, J=24 Hz, 1H), 3.35 (d, J=24 Hz, 1H), 1.80 (s, 3H), 1.50 (s, 9H), 1.30 (s, 9H). MS (ESI): MH⁺=491.8. HPLC t_R=6.2 min.

Step 3

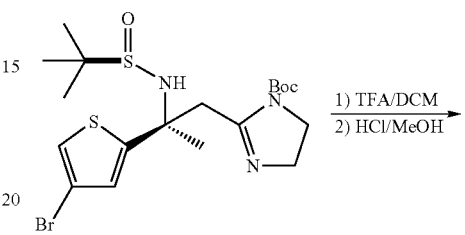

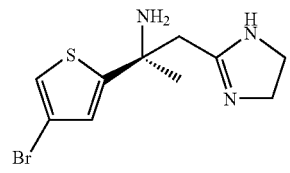

A mixture of I2 (600 mg, 1.2 mmol) with 4 mL of 1:2 (v/v) TFA/CH₂Cl₂ was stirred at RT for 16 h. The mixture was concentrated and the residue was redissolved in 6 mL of 1.5M HCl/MeOH. After stirring at RT for 16 h, the mixture was concentrated to 230 mg (65%) of 13 as a brown solid. MS (ESI): MH⁺=288.2.

Step 4

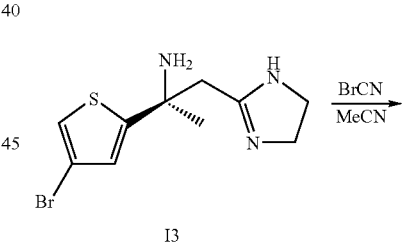

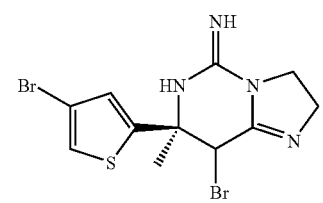

Example 19

To a solution of I3 (230 mg, 0.80 mmol) in 6 mL of acetonitrile at 0° C. was added dropwise cyanogen bromide (2 mL, 5 M in acetonitrile, 12 eq). After stirring at RT for 2 h, the mixture was concentrated and the residue was chromatographed on silica gel (5% MeOH/CH₂Cl₂) to give 160 mg (40%) of Example 19 as yellowish solid. ¹HNMR (CDCl₃, 300 MHz, a mixture of ~1:1 diastereomers): δ 7.10 (s, 1H), 7.0 (s, 1H), 6.85 (s, 1H), 6.80 (s, 1H), 4.95 (s, 1H), 4.80 (s, 1H), 4.0-3.6 (m, 8H), 1.75 (s, 3H), 1.55 (s, 3H). MS (ESI): MH$^+$=390.9. HPLC $t_R$=4.6 min.

Compound Example 20

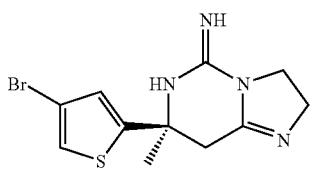 [SMILES: C[C@@]1(c2cc(Br)cs2)CC2=NCCN2C(=N)N1]

Example 20

Step 1

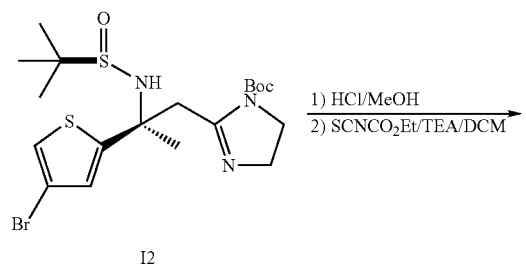

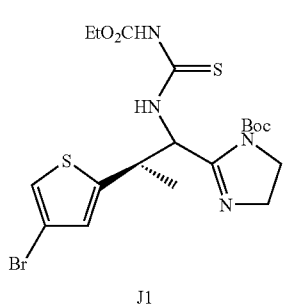

A mixture of 1.24 g (2.5 mmol) 12 with 8 mL of 1.5M HCl/MeOH was stirred at RT for 16 h. The solvent was evaporated and the residue was concentrated to give 0.90 g (92%) of (S)-tert-butyl 2-(2-amino-2-(4-bromothiophen-2-yl)propyl)-4,5-dihydroimidazole-1-carboxylate as a brown solid. MH$^+$=387.8. HPLC $t_R$=5.3 min. To a solution of (S)-tert-butyl 2-(2-amino-2-(4-bromothiophen-2-yl)propyl)-4,5-dihydroimidazole-1-carboxylate (~2.5 mmol) in 16 mL of dichloromethane was added Et$_3$N (0.65 g, 6.4 mmol, 2.5 eq), followed by ethyl isothiocyanatoformate (0.40 g, 3.0 mmol, 1.2 eq). After stirring at RT for 16 h, the mixture was washed with water, brine, dried over Na$_2$SO$_4$, and concentrated. The residue was chromatographed on silica gel (1:1 EtOAc/hexane) to give 600 mg (50%) of J1 as a brown solid. $^1$HNMR (CDCl$_3$, 300 MHz): δ 10.65 (s, 1H), 7.90 (s, 1H), 7.05 (s, 1H), 6.80 (s, 1H), 4.20 (m, 2H), 3.8 (m, 4H), 3.65 (d, J=16 Hz, 1H), 3.50 (d, J=16 Hz, 1H), 2.10 (s, 3H), 1.50 (s, 9H), 1.30 (s, 9H). MS (ESI): MH$^+$=518.7. HPLC $t_R$=6.4 min.

Step 2

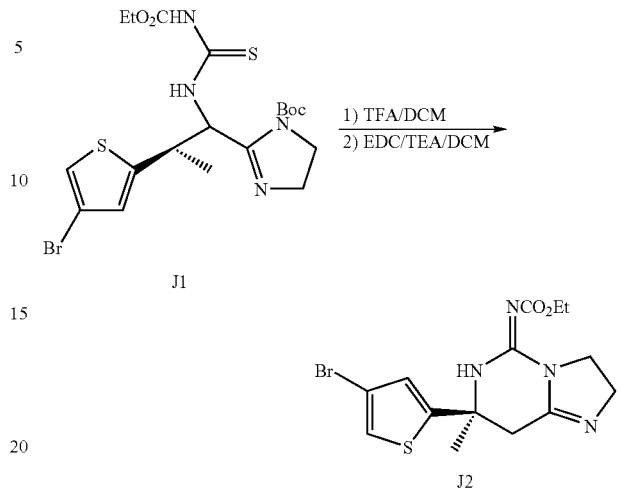

A mixture of J1 (600 mg, 1.1 mmol) with 10 mL of 1:2 (v/v) TFA/CH$_2$Cl$_2$ was stirred at RT for 16 h. The solvent was evaporated to give 420 mg (87%) of (S)-ethyl 2-(4-bromothiophen-2-yl)-1-(4,5-dihydro-1H-imidazol-2-yl)propan-2-ylcarbamothioylcarbamate as a brown solid MH$^+$=392.2. HPLC $t_R$=5.4 min. To a solution of (S)-ethyl 2-(4-bromothiophen-2-yl)-1-(4,5-dihydro-1H-imidazol-2-yl)propan-2-ylcarbamothioylcarbamate (~1.1 mmol) in 14 mL of dichloromethane was added diisopropylethylamine (0.59 g, 4.5 mmol, 4 eq), followed by 1-[3-(dimethylamino)propyl]-3-ethylcarbodiimide hydrochloride (0.47 g, 2.5 mmol, 2.2 eq). After stirring at RT for 3 days, the mixture was washed with water, brine, dried (Na$_2$SO$_4$) and concentrated. The crude material was chromatographed on silica gel (5% MeOH/CH$_2$Cl$_2$) to give 300 mg (77%) of J2 as an amber solid. $^1$HNMR (CDCl$_3$, 300 MHz): δ 9.72 (s, 1H), 7.13 (s, 1H), 6.84 (s, 1H), 4.16 (q, J=6.9 Hz, 2H), 3.9 (m, 4H), 3.20 (d, J=16 Hz, 1H), 3.50 (d, J=16 Hz, 1H), 1.74 (s, 3H), 1.50 (s, 9H), 1.32 (t, J=6.9 Hz, 3H). MH$^+$=385.0. HPLC $t_R$=5.3 min.

Step 3

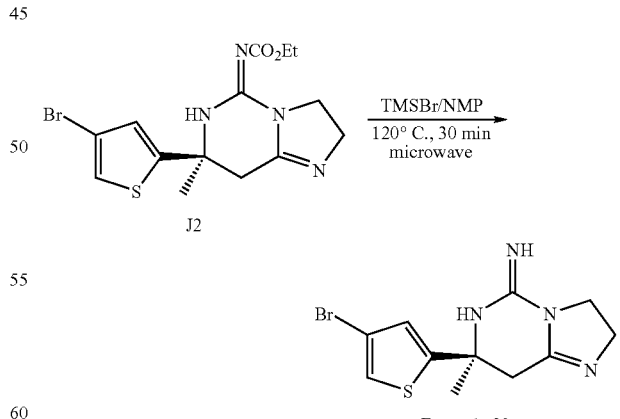

Example 20

To a solution of J2 (76 mg, 0.20 mmol, 1 eq) in 2 mL of 1-methyl-2-pyrrolidinone was added bromotrimethylsilane. The mixture was heated at 120° C. in a microwave reactor for 30 min. The mixture was diluted with CH$_2$Cl$_2$ (50 mL), quenched with saturated aq. NaHCO$_3$, and then washed with water, brine, dried over Na$_2$SO$_4$ and concentrated. The crude material was purified by reverse phase preparative HPLC to afford 22 mg (62%) of Example 20 as a colorless oil. $^1$HNMR (CD$_3$OD, 300 MHz): δ 7.43 (s, 1H), 7.09 (s, 1H), 4.20 (m, 1H), 4.0 (m, 1H), 3.45 (d, J=16 Hz, 1H), 3.28 (d, J=16 Hz, 1H), 1.80 (s, 3H). MH$^+$=313.0. HPLC t$_R$=4.3 min.

Compound Example 21

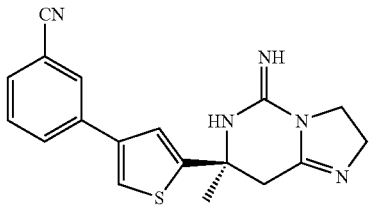 [SMILES: C[C@@]1(c2cc(-c3cccc(C#N)c3)cs2)CC2=NCCN2C(=N)N1]

Example 21

Step 1

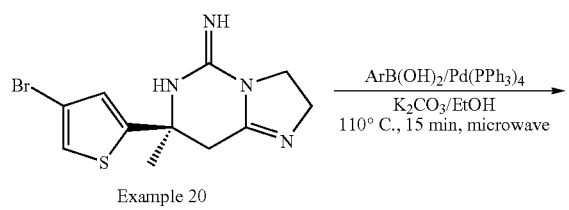

A mixture of Example 20 (16 mg, 0.05 mmol), 3-cyanophenylboronic acid (16 mg, 0.11 mmol), Pd(PPh$_3$)$_4$ (8 mg, 0.007 mmol), and K$_3$CO$_3$ (0.5 mL, 1M aq. solution, 0.5 mmol, 10 eq) in 1.5 mL of EtOH was heated at 110° C. in a microwave reactor for 15 min. The mixture was concentrated and the residue was purified by reverse phase preparative HPLC to afford 7 mg (42%) of Example 21 as a white solid. $^1$HNMR (CD$_3$OD, 300 MHz): δ 8.05 (s, 1H), 7.95 (d, J=12 Hz, 1H), 7.80 (s, 1H), 7.65 (d, J=12 Hz, 1H), 7.60 (t, J=12 Hz, 1H), 7.55 (s, 1H), 4.20 (m, 1H), 4.0 (m, 1H), 3.55 (d, J=16 Hz, 1H), 3.30 (d, J=16 Hz, 1H), 3.2 (m, 2H), 1.90 (s, 3H). MH$^+$+18=354.3. HPLC t$_R$=4.6 min.

Compound Example 22

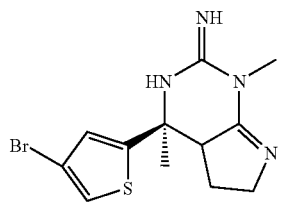 [SMILES: CN1C(=N)N[C@](C)(c2cc(Br)cs2)C2CCN=C21]

Example 22

Step 1

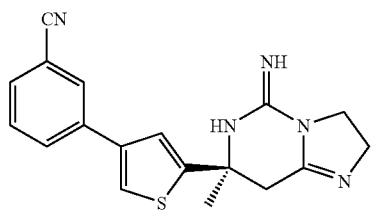

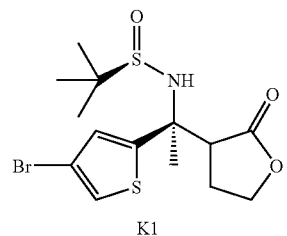

To a solution of iPr$_2$NH (5.0 mL, 35.6 mmol) in THF (160 mL) cooled to 0° C. was added BuLi. The mixture was stirred at 0° C. for 10 minutes and then cooled to −78° C. γ-Butyrolactone (2.5 mL, 32.5 mmol) was added slowly as a solution in THF (35 mL), and the resulting solution was stirred at −78° C. for 20 minutes. To this solution was added ClTi(OiPr)$_3$ (14 mL, 58.5 mmol) and stirring continued for an additional 25 minutes. A solution of D1 (5.0 g, 16.3 mmol) in THF (30 mL) was added slowly, and the resulting solution was warmed to −20° C. over a 3 h period. The reaction was quenched with H$_2$O and diluted with EtOAc. The suspension was filtered through a pad of celite with the aid of additional EtOAc. The organic layer was removed and the aqueous layer was extracted with EtOAc (3×). The combined organics were dried (Na$_2$SO$_4$), filtered, and concentrated. The residue was purified by silica gel chromatography to yield K1 (4.25 g, 10.8 mmol, 66% yield). MS m/e: 394.2 (M+H).

Step 2

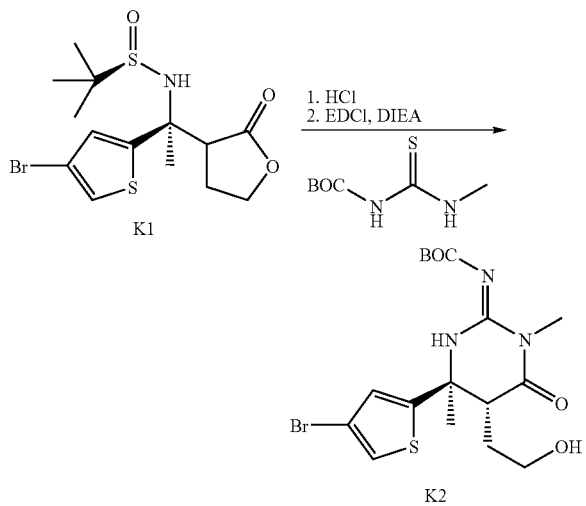

A solution of K1 (4.1 g, 10.5 mmol) in MeOH (40 mL) was treated with 4N HCl/Dioxane (40 mL) at RT for 45 minutes. The reaction was concentrated, and the material was used without purification.

To a solution of the crude material prepared above in DMF (20 mL) was added DIEA (15 mL, 86.3 mmol), 1-BOC-3-methyl thiourea (2.4 g, 12.6 mmol), and EDCI (2.4 g, 12.6 mmol). The resulting mixture was stirred at RT for 72 h. After dilution with H$_2$O and EtOAc, the organic layer was removed, and the aqueous phase was extracted with EtOAc (3×). The combined organics were washed with brine (4×), dried (Na$_2$SO$_4$), filtered, and concentrated. The residue was purified by silica gel chromatography to yield K2 (4.5 g, 10.1 mmol, 96% yield). MS m/e: 446.2 (M+H).

Step 3

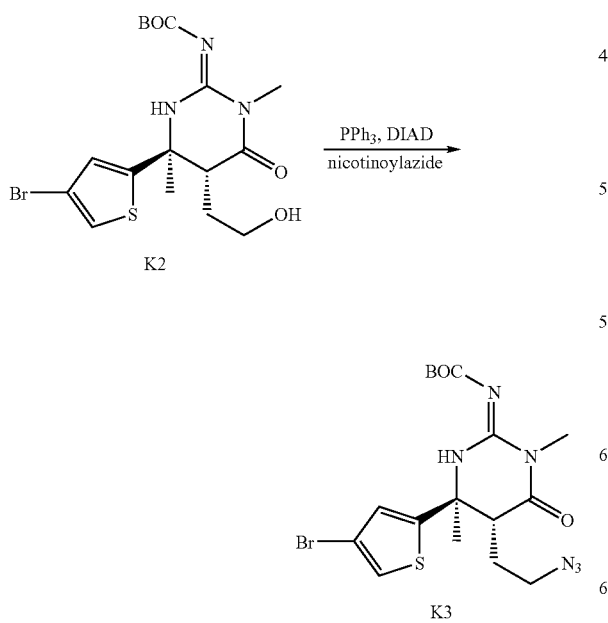

To a solution of K2 (0.523 g, 1.17 mmol) and PPh$_3$ (0.463 g, 1.76 mmol) in THF (11 mL) cooled to 0° C. was added DIAD (0.350 mL, 1.78 mmol). The resulting yellow solution was stirred for 20 minutes and nicotinoyl azide (0.227 g, 1.52 mmol) was added as one solid portion. The mixture was stirred at 0° C. for 30 minutes and at RT for 2 h. The solvent was concentrated, and the orange oil was purified by silica gel chromatography to yield K3 (0.453 g, 0.96 mmol, 82% yield). MS m/e: 471.3 (M+H).

Step 4

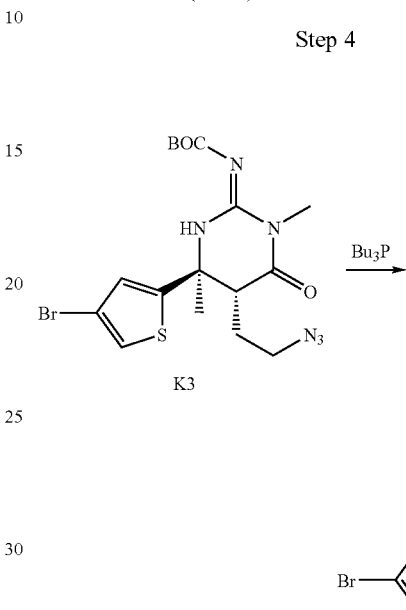

To a degassed solution of K3 (0.071 g, 0.15 mmol) in THF (1 mL) was added Bu$_3$P (0.030 mL, 0.22 mmol). The reaction was stirred at RT for 2 h and then an additional 16 h at 65° C. The reaction was concentrated and the material was purified by reverse phase HPLC to yield K4 (0.002 g, 0.005 mmol, 3% yield). MS m/e: 427.2 (M+H).

Step 5

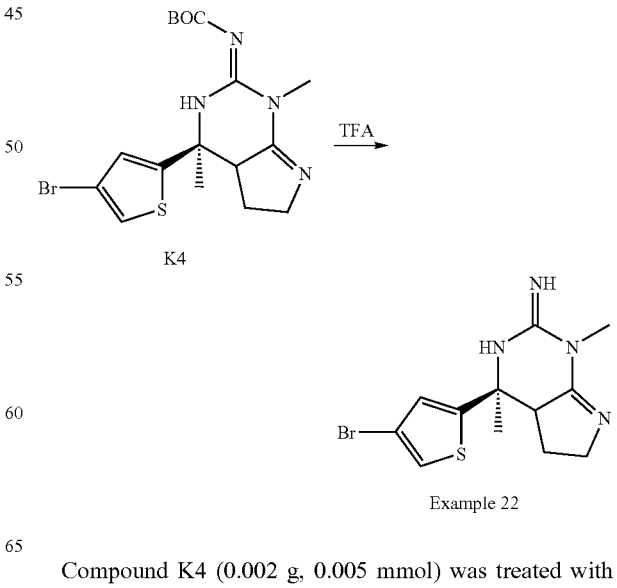

Compound K4 (0.002 g, 0.005 mmol) was treated with 20% TFA/CH$_2$Cl$_2$ for 1 h. The solution was concentrated, and the residue was purified by reverse phase HPLC to yield Example 22 (0.001 g, 0.003 mmol, 67% yield). MS m/e: 327.2 (M+H).

The following assays may be used to evaluate the biological properties of the inventive compounds.

Human Cathepsin D FRET assay

The substrate discussed below is described (Y. Yasuda et al., J. Biochem., 125, 1137 (1999)). Substrate and enzyme are commercially available. A Km of 4 uM was determined for the substrate below under the assay conditions described and is consistent with Yasuda et al.

The assay is run in a 30 ul final volume using a 384 well Nunc black plate. 8 concentrations of compound are pre-incubated with enzyme for 30 mins at 37 C followed by addition of substrate with continued incubation at 37 C for 45 mins. The rate of increase in fluorescence is linear for over 1 h and is measured at the end of the incubation period using a Molecular Devices FLEX station plate reader. K is are interpolated from the IC50s using a Km value of 4 uM and the substrate concentration of 2.5 uM.

Reagents
Na-Acetate pH 5
1% Brij-35 from 10% stock (Calbiochem)
DMSO
Purified (>95%) human liver Cathepsin D (Athens Research & Technology Cat#16-12-030104)
Peptide substrate (Km=4 uM) Bachem Cat # M-2455
Pepstatin is used as a control inhibitor (Ki~0.5 nM) and is available from Sigma.
Nunc 384 well black plates
Final Assay Buffer Conditions
100 mM Na Acetate pH 5.0
0.02% Brij-35
1% DMSO Compound is diluted to 3x final concentration in assay buffer containing 3% DMSO. 10 ul of compound is added to 10 ul of 2.25 nM enzyme(3x) diluted in assay buffer without DMSO, mixed briefly, spun, and incubated at 37 C for 30 mins. 3x substrate (7.5 uM) is prepared in 1x assay buffer without DMSO. 10 ul of substrate is added to each well mixed and spun briefly to initiate the reaction. Assay plates are incubated at 37 C for 45 mins and read on 384 compatible fluorescence plate reader using a 328 nm Ex and 393 nm Em.

BACE-1 Cloning, Protein Expression and Purification

A predicted soluble form of human BACE1 (sBACE1, corresponding to amino acids 1-454) is generated from the full length BACE1 cDNA (full length human BACE1 cDNA in pCDNA4/mycHisA construct; University of Toronto) by PCR using the advantage-GC cDNA PCR kit (Clontech, Palo Alto, Calif.). A HindIII/PmeI fragment from pCDNA4-sBACE1 myc/His is blunt ended using Klenow and subcloned into the Stu I site of PFASTBACI(A) (Invitrogen). A sBACE1 mycHis recombinant bacmid is generated by transposition in DH10Bac cells(GIBCO/BRL). Subsequently, the sBACE1 mycHis bacmid construct is transfected into sf9 cells using CellFectin (Invitrogen, San Diego, Calif.) in order to generate recombinant baculovirus. Sf9 cells are grown in SF 900-II medium (Invitrogen) supplemented with 3% heat inactivated FBS and 0.5x penicillin/streptomycin solution (Invitrogen). Five milliliters of high titer plaque purified sBACEmyc/His virus is used to infect 1 L of logarithmically growing sf9 cells for 72 hours. Intact cells are pelleted by centrifugation at 3000xg for 15 minutes. The supernatant, containing secreted sBACE1, is collected and diluted 50% v/v with 100 mM HEPES, pH 8.0. The diluted medium is loaded onto a Q-sepharose column. The Q-sepharose column is washed with Buffer A (20 mM HEPES, pH 8.0, 50 mM NaCl).

Proteins are eluted from the Q-sepharose column with Buffer B (20 mM HEPES, pH 8.0, 500 mM NaCl). The protein peaks from the Q-sepharose column are pooled and loaded onto a Ni-NTA agarose column. The Ni-NTA column is then washed with Buffer C (20 mM HEPES, pH 8.0, 500 mM NaCl). Bound proteins are then eluted with Buffer D (Buffer C+250 mM imidazole). Peak protein fractions as determined by the Bradford Assay (Biorad, CA) are concentrated using a Centricon 30 concentrator (Millipore). sBACE1 purity is estimated to be ~90% as assessed by SDS-PAGE and Commassie Blue staining. N-terminal sequencing indicated that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin; CIS-Bio International, France), 5 µM unlabeled APPsw peptide (KTEEISEVNLDAEFRHDK; American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol are preincubated for 30 min at 30° C. Reactions are initiated by addition of substrate in a 5 µl aliquot resulting in a total volume of 25 µl. After 3 hr at 30° C. reactions are terminated by addition of an equal volume of 2x stop buffer containing 50 mM Tris-HCl pH 8.0, 0.5 M KF, 0.001% Brij-35, 20 µg/ml SA-XL665 (cross-linked allophycocyanin protein coupled to streptavidin; CIS-Bio International, France) (0.5 µg/well). Plates are shaken briefly and spun at 1200xg for 10 seconds to pellet all liquid to the bottom of the plate before the incubation. HTRF measurements are made on a Packard Discovery® HTRF plate reader using 337 nm laser light to excite the sample followed by a 50 µs delay and simultaneous measurements of both 620 nm and 665 nm emissions for 400 µs.

$IC_{50}$ determinations for inhibitors, (I), are determined by measuring the percent change of the relative fluorescence at 665 nm divided by the relative fluorescence at 620 nm, (665/620 ratio), in the presence of varying concentrations of i and a fixed concentration of enzyme and substrate. Nonlinear regression analysis of these data is performed using Graph-Pad Prism 3.0 software selecting four parameter logistic equation, that allows for a variable slope. Y=Bottom+(Top-Bottom)/(1+10^((LogEC50−X)*Hill Slope)); X is the logarithm of concentration of 1, Y is the percent change in ratio and Y starts at bottom and goes to top with a sigmoid shape.

Using the above assay, the $K_i$ values of the compounds of Examples 1 to 9 and 12 to 20 were determined. The $K_i$ values ranged from 1 to 1,000,000 nM, with some preferred compound exhibiting $K_i$ values of less than 100 nM.

Human Mature Renin Enzyme Assay:

Human Renin is cloned from a human kidney cDNA library and C-terminally epitope-tagged with the V5-6His sequence into pCDNA3.1. pCNDA3.1-Renin-V5-6His is stably expressed in HEK293 cells and purified to >80% using standard Ni-Affinity chromatography. The prodomain of the recombinant human renin-V5-6His is removed by limited proteolysis using immobilized TPCK-trypsin to give mature-human renin. Renin enzymatic activity is monitored using a commercially available fluorescence resonance energy transfer(FRET) peptide substrate, RS-1 (Molecular Probes, Eugene, Oreg.) in 50 mM Tris-HCl pH 8.0, 100 mM NaCl, 0.1% Brij-35 and 5% DMSO buffer for 40 mins at 30 degrees celsius in the presence or absence of different concentrations of test compounds. Mature human Renin is present at approximately 200 nM. Inhibitory activity is defined as the percent decrease in renin induced fluorescence at the end of the 40 min incubation compared to vehicle controls and samples lacking enzyme.

In the aspect of the invention relating to a combination of a compound of formula I with a cholinesterase inhibitor, acetyl- and/or butyrylchlolinesterase inhibitors can be used. Examples of cholinesterase inhibitors are tacrine, donepezil, rivastigmine, galantamine, pyridostigmine and neostigmine, with tacrine, donepezil, rivastigmine and galantamine being preferred.

In the aspect of the invention relating to a combination of a compound of formula I with a muscarinic antagonist, $m_1$ or $m_2$ antagonists can be used. Examples of $m_1$ antagonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Other example of pharmaceutical agents include beta secretase inhibitors; HMG-CoA reductase inhibitors, such as atorvastatin, lovastatin, simvistatin, pravastatin, fluvastatin and rosuvastatin; non-steroidal anti-inflammatory agents, such as ibuprofen, N-methyl-D-aspartate receptor antagonists, such as memantine, anti-amyloid antibodies including humanized monoclonal antibodies; vitamin E; nicotinic acetylcholine receptor agonists; CB1 receptor inverse agonists or CB1 receptor antagonists; antibiotics, e.g., docycycline; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity, and cholesterol absorption inhibitors; e.g., bile sequestants azetidinones, such as ezetimibe (ZETIA).

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

When a compound of formula I is used in combination with a cholinesterase inhibitor to treat cognitive disorders, these two active components may be co-administered simultaneously or sequentially, or a single pharmaceutical composition comprising a compound of formula I and a cholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the cholinesterase inhibitor can be determined from published material, and may range from 0.001 to 100 mg/kg body weight.

When separate pharmaceutical compositions of a compound of formula I and a cholinesterase inhibitor are to be administered, they can be provided in a kit comprising in a single package, one container comprising a compound of formula I in a pharmaceutically acceptable carrier, and a separate container comprising a cholinesterase inhibitor in a pharmaceutically acceptable carrier, with the compound of formula I and the cholinesterase inhibitor being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A compound having the Formula (IA):

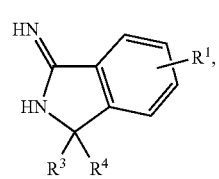

IA or a stereoisomer, tautomer, or pharmaceutically acceptable salt of said compound, stereoisomer, or tautomer, wherein:
$R^1$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{15}$;
$R^3$ is alkyl, cycloalkylalkyl, cycloalkyl, aryl, $R^{21}$-cycloalkylalkyl, $R^{21}$-cycloalkyl, $R^{21}$-aryl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;
$R^4$ is cycloalkylalkyl, cycloalkyl, aryl, $R^{21}$-alkyl, $R^{21}$-cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;
$R^{15}$ is selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, and arylheterocycloalkyl; and
each $R^{21}$ is independently H, alkyl, halo, CN, —OR$^{24}$, optionally substituted phenyl or optionally substituted heteroaryl, wherein the optional substituents on said optionally substituted phenyl or said optionally substituted heteroaryl are alkyl, halo, CN or —OR$^{24}$, where each R$^{24}$ is independently alkyl, aryl or heteroaryl and wherein when R$^3$ is methyl or ethyl, R$^4$ is not methyl or ethyl.

2. A compound of claim 1, or a stereoisomer, tautomer, or pharmaceutically acceptable salt of said compound, stereoisomer, or tautomer, wherein R$^1$ is hydrogen, lower alkyl, halogen, alkoxy, or cyano.

3. A compound of claim 1, or a stereoisomer, tautomer, or pharmaceutically acceptable salt of said compound, stereoisomer, or tautomer, wherein:
R$^3$ is alkyl:
R$^4$ is

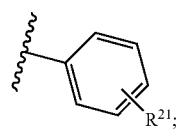

and
R$^{21}$ is optionally substituted phenyl or optionally substituted heteroaryl, wherein the optional substituents on said optionally substituted phenyl or said optionally substituted heteroaryl are alkyl, halo, CN or —OR$^{24}$, where each R$^{24}$ is independently alkyl, aryl or heteroaryl.

4. A compound of claim 1, or a stereoisomer, tautomer, or pharmaceutically acceptable salt of said compound, stereoisomer, or tautomer, wherein R$^3$ and R$^4$ are each independently

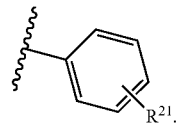

5. A compound of claim 1, or a stereoisomer, tautomer, or a pharmaceutically acceptable salt thereof, selected from the group consisting of:

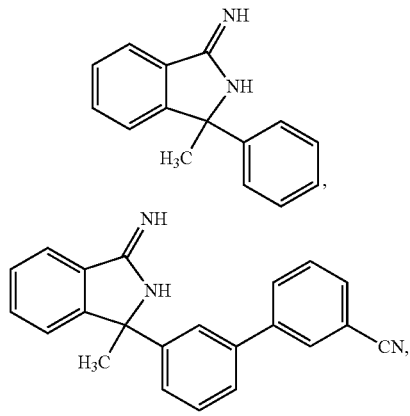

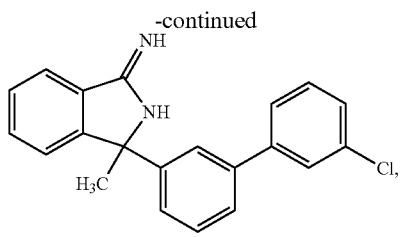

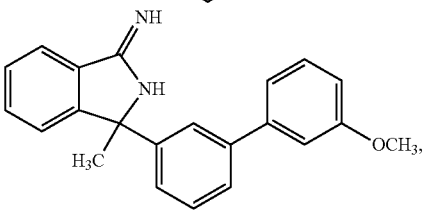

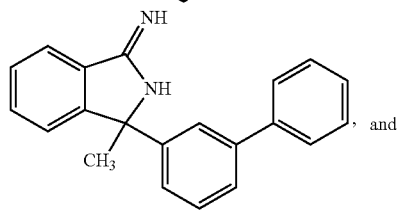

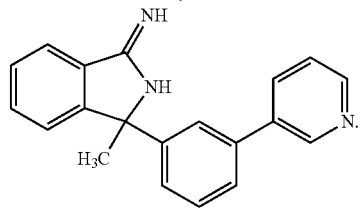

6. A compound of claim 1, wherein:
R$^3$ is alkyl, cycloalkylalkyl, cycloalkyl, aryl, R$^{21}$-cycloalkylalkyl, R$^{21}$-cycloalkyl, R$^{21}$-aryl, heteroaryl, heterocycloalkyl, heterocycloalkylalkyl, R$^{21}$-heteroaryl, R$^{21}$-heterocycloalkyl or R$^{21}$-heterocycloalkylalkyl; and R$^4$ is cycloalkylalkyl, cycloalkyl, aryl, R$^{21}$-cycloalkylalkyl, R$^{21}$-cycloalkyl, R$^{21}$-aryl, heteroaryl, heterocycloalkyl, heterocycloalkylalkyl, R$^{21}$-heteroaryl, R$^{21}$-heterocycloalkyl or R$^{21}$-heterocycloalkylalkyl.

7. The compound according to claim 1, wherein:
R$^3$ is alkyl, aryl, R$^{21}$-aryl, heteroaryl, or R$^{21}$-heteroaryl; and
R$^4$ is aryl, R$^{21}$-aryl, heteroaryl, or R$^{21}$-heteroaryl.

8. The compound according to claim 6, wherein R$^4$ is phenyl or R$^{21}$-phenyl, where said R$^{21}$ is aryl or heteroaryl wherein said aryl and said heteroaryl group is optionally substituted by halo, haloalkyl, —CN or —OR$^{24}$, where R$^{24}$ is alkyl.

9. A pharmaceutical composition comprising a compound according to any one of claim 1, 2, 3, 4, 5, 6, 7, or 8, or a stereoisomer, tautomer, or a pharmaceutically acceptable salt thereof, and a pharmaceutically effective carrier.

* * * * *